(12) United States Patent
Rieth et al.

(10) Patent No.: US 9,458,414 B2
(45) Date of Patent: Oct. 4, 2016

(54) CLEANING, SURFACTANT, AND PERSONAL CARE COMPOSITIONS

(71) Applicant: SEGETIS, INC., Golden Valley, MN (US)

(72) Inventors: Lee R. Rieth, Plymouth, MN (US); Satyanarayana Majeti, Liberty Township, OH (US); Erich J. Molitor, Midland, MI (US)

(73) Assignee: GFBIOCHEMICALS LIMITED, Valletta (MT)

( * ) Notice: Subject to any disclaimer, the term of this patent is extended or adjusted under 35 U.S.C. 154(b) by 0 days.

(21) Appl. No.: 14/429,796

(22) PCT Filed: Sep. 20, 2013

(86) PCT No.: PCT/US2013/060883
§ 371 (c)(1),
(2) Date: Mar. 20, 2015

(87) PCT Pub. No.: WO2014/047428
PCT Pub. Date: Mar. 27, 2014

(65) Prior Publication Data
US 2015/0252302 A1 Sep. 10, 2015

Related U.S. Application Data

(60) Provisional application No. 61/704,182, filed on Sep. 21, 2012.

(51) Int. Cl.
| | |
|---|---|
| *A61K 31/357* | (2006.01) |
| *C07D 317/20* | (2006.01) |
| *C11D 3/20* | (2006.01) |
| *C11D 7/26* | (2006.01) |
| *A61K 8/49* | (2006.01) |
| *A61Q 19/00* | (2006.01) |
| *A61Q 5/10* | (2006.01) |

(52) U.S. Cl.
CPC ............. *C11D 3/2096* (2013.01); *A61K 8/498* (2013.01); *A61Q 5/10* (2013.01); *A61Q 19/00* (2013.01); *C07D 317/20* (2013.01); *C11D 3/2072* (2013.01); *C11D 7/264* (2013.01); *A61K 2800/10* (2013.01)

(58) Field of Classification Search
CPC ..... C11D 3/20; C07D 317/20; A61K 31/357
USPC .......................................... 549/453; 514/467
See application file for complete search history.

(56) References Cited

U.S. PATENT DOCUMENTS

| | | | |
|---|---|---|---|
| 1,934,309 | A | 10/1927 | Hoover |
| 2,008,720 | A | 7/1935 | Lawson |
| 2,260,261 | A | 10/1941 | Morey et al. |
| 2,556,135 | A | 6/1954 | Croxall et al. |
| 2,985,536 | A | 5/1961 | Stein et al. |
| 3,201,420 | A | 8/1965 | Fuzesi et al. |
| 3,855,248 | A | 12/1974 | Lannert et al. |
| 4,460,767 | A | 7/1984 | Matsumura et al. |
| 4,465,866 | A | 8/1984 | Takaishi et al. |
| 4,737,426 | A | 4/1988 | Roth |
| 4,792,411 | A | 12/1988 | Walsh |
| 4,806,448 | A | 2/1989 | Roth |
| 5,013,543 | A | 5/1991 | Mercado et al. |
| 5,093,111 | A | 3/1992 | Baker et al. |
| 5,266,592 | A | 11/1993 | Grub et al. |
| 5,419,848 | A | 5/1995 | Van Eenam |
| 5,482,965 | A | 1/1996 | Rajadhyaksha |
| 5,516,459 | A | 5/1996 | Van Eenam |
| 5,700,522 | A | 12/1997 | Nonweiler et al. |
| 5,705,087 | A | 1/1998 | Mushrush et al. |
| 5,859,263 | A | 1/1999 | Ghorpade et al. |
| 5,917,059 | A | 6/1999 | Bruchmann et al. |
| 5,998,092 | A | 12/1999 | McCulloch et al. |
| 6,010,995 | A | 1/2000 | Van Eenam |
| 6,034,118 | A | 3/2000 | Bischofberger et al. |
| 6,036,925 | A | 3/2000 | Adams et al. |
| 6,130,195 | A | 10/2000 | Doyel et al. |
| 6,306,249 | B1 | 10/2001 | Galante et al. |

(Continued)

FOREIGN PATENT DOCUMENTS

| | | |
|---|---|---|
| CA | 1000285 | 11/1976 |
| CA | 2347255 A1 | 2/2004 |
| DE | 10036423 A1 | 3/2001 |
| EP | 0012543 A1 | 6/1980 |
| EP | 0308956 A2 | 3/1989 |
| EP | 0507190 A1 | 10/1992 |
| EP | 0913463 A1 | 5/1999 |
| FR | 1445013 | 7/1966 |
| GB | 1196202 | 6/1970 |
| GB | 1427918 | 3/1976 |

(Continued)

OTHER PUBLICATIONS

Boehm et al., "Knowledge on cyclic ketals. Part 11: Synthesis of some new derivatives and separation of their isomers", Pharmazie 36 (5), (1981), 3 pages.

Brigl, Percy, et al., "The Reaction of the Pyruvic Acid with Glycerin," Annalen der Chemie 476: p. 215-232, Received Oct. 7, 1929, (with English translation).

Briol et al., "Reaction of pyroracemic acid with glycerol", Ann. (1929), 476, 215-32, Abstract Only, 1 page.

(Continued)

*Primary Examiner* — Golam M M Shameem
(74) *Attorney, Agent, or Firm* — Cantor Colburn LLP

(57) ABSTRACT

A cleaning or personal care composition containing at least one of 1,4-pentanediol and a ketal alcohol of formula (1) wherein $R^2$ is hydrogen or C1-3 alkyl, each $R^3$, $R^4$, and $R^5$ is independently hydrogen or C1-6 alkyl, $R^6$ and $R^7$ are each independently hydrogen or C1-6 alkyl, a=0-3, and b=0-1. $R^2$ is hydrogen or C1-3 alkyl, each $R^3$, $R^4$, and $R^5$ is independently hydrogen or C1-6 alkyl, each $R^6$ and $R^7$ is independently hydrogen, C1-6 alkyl optionally substituted with at least one hydroxyl groups, a=1-6, and b=0-2.

18 Claims, 3 Drawing Sheets

(56) References Cited

U.S. PATENT DOCUMENTS

| | | | |
|---|---|---|---|
| 6,372,791 | B1 | 4/2002 | Shapiro et al. |
| 6,403,109 | B1 | 6/2002 | Stora |
| 6,423,480 | B2 | 7/2002 | Ichiki |
| 6,423,677 | B1 | 7/2002 | Van Eenam |
| 6,451,223 | B1 | 9/2002 | Jeon |
| 6,528,025 | B1 | 3/2003 | Boesch et al. |
| 6,627,181 | B1 | 9/2003 | Busch, Jr. et al. |
| 6,749,998 | B2 | 6/2004 | Schwartzkopf et al. |
| 6,806,392 | B2 | 10/2004 | Boesch et al. |
| 6,962,767 | B2 | 11/2005 | Watanabe et al. |
| 7,094,395 | B1 | 8/2006 | Qu et al. |
| 7,179,775 | B2 | 2/2007 | Foster |
| 8,575,367 | B2 * | 11/2013 | Selifonov ............ C07D 317/30 549/200 |
| 8,632,612 | B2 | 1/2014 | Yontz |
| 8,962,597 | B2 * | 2/2015 | Rieth ....................... A61K 8/25 424/400 |
| 9,156,809 | B2 * | 10/2015 | Rieth ....................... C11B 9/008 |
| 2002/0183234 | A1 | 12/2002 | Jalalian et al. |
| 2003/0007986 | A1 | 1/2003 | Stora et al. |
| 2003/0133895 | A1 | 7/2003 | China et al. |
| 2003/0167681 | A1 | 9/2003 | Delgado Puche |
| 2004/0024260 | A1 | 2/2004 | Winkler et al. |
| 2004/0120918 | A1 | 6/2004 | Lintner et al. |
| 2004/0138090 | A1 | 7/2004 | Drapier et al. |
| 2004/0147602 | A1 | 7/2004 | Smith et al. |
| 2004/0157759 | A1 | 8/2004 | Scherubel |
| 2004/0167245 | A1 | 8/2004 | Chappelow et al. |
| 2005/0106112 | A1 | 5/2005 | Boyd et al. |
| 2005/0233927 | A1 | 10/2005 | Scherubel |
| 2005/0245407 | A1 | 11/2005 | Ishihara et al. |
| 2006/0069230 | A1 | 3/2006 | Papisov |
| 2006/0134045 | A1 | 6/2006 | Cao et al. |
| 2006/0207037 | A1 | 9/2006 | Fadel et al. |
| 2006/0211855 | A1 | 9/2006 | Doring et al. |
| 2007/0111917 | A1 | 5/2007 | Lang et al. |
| 2007/0161530 | A1 | 7/2007 | Kaneda et al. |
| 2008/0096785 | A1 | 4/2008 | Egbe et al. |
| 2008/0124426 | A1 | 5/2008 | Kobler et al. |
| 2008/0188603 | A1 | 8/2008 | Porzio et al. |
| 2008/0242721 | A1 | 10/2008 | Selifonov |
| 2008/0305978 | A1 | 12/2008 | Wietfeldt et al. |
| 2009/0124531 | A1 | 5/2009 | Danziger et al. |
| 2010/0087357 | A1 | 4/2010 | Morgan, III et al. |
| 2011/0196081 | A1 | 8/2011 | Kwon et al. |
| 2011/0300083 | A1 | 12/2011 | Yontz et al. |
| 2012/0122745 | A1 | 5/2012 | Mullen et al. |

FOREIGN PATENT DOCUMENTS

| | | |
|---|---|---|
| JP | 28004327 A | 9/1953 |
| JP | 4217972 A | 8/1992 |
| JP | H07228887 A | 8/1995 |
| JP | 2006022119 A | 1/2006 |
| JP | 2006143702 A | 6/2006 |
| JP | 2008293026 A | 12/2008 |
| JP | 2009035733 A | 2/2009 |
| JP | 2009179624 A | 8/2009 |
| SU | 722912 | 3/1980 |
| WO | 9412489 A1 | 6/1994 |
| WO | 9856889 | 9/1999 |
| WO | 0193813 A2 | 12/2001 |
| WO | 2004099173 A1 | 11/2004 |
| WO | 2005095378 A2 | 10/2005 |
| WO | 2005097723 A2 | 10/2005 |
| WO | 2005097724 A1 | 10/2005 |
| WO | 2007062158 A2 | 5/2007 |
| WO | 2007145994 A2 | 12/2007 |
| WO | 2008089463 A2 | 7/2008 |
| WO | 2008098375 A1 | 8/2008 |
| WO | 2009032905 A1 | 3/2009 |
| WO | 2009048874 A1 | 4/2009 |
| WO | 2010043717 A3 | 4/2010 |
| WO | 2010096623 A1 | 8/2010 |
| WO | 2010151558 A1 | 12/2010 |
| WO | 2011047420 A1 | 4/2011 |

OTHER PUBLICATIONS

Calinaud et al., "Cyclic acetal series. XIII. Opening of 4-oxo and 4-hydroxy-3,6,8-trioxabicyclo[3.2.1]octane and 3-pxp-2,5,7-trioxabicyclo[2.2.2]octane rings by lithium aluminum hydride and methylmagnesium iodide", Carbohydrate Res. 30(1) 1973 Abst Only.

Carey, et al., "Advanced Organic Chemistry, Second Edition, Part B: Reactions and Synthesis," Plenum Press 539-552 (1983).

Cuiling et al., "Synthesis of Levulinic Ketals with Furfuryl Alcohol as Raw Material", Journal of Huagiao University (Nature Science) 23 (3), Jul. 2002, pp. 257-259, with English Translation, 8 pages.

Doolittle, Arthur K., "Application of a Mechanistic Theory of Solvent Action to Plasticizers and Platicization", Journal of Polymer Science, vol. 2, No. 2 (1947) 121-141.

Eastman Chemical Company. (May 2006). Selecting Coupling Agents for Multi-phase Models. Retrieved Aug. 13, 2009, from http://www.eastman.com/Literature Center/M/M207.pdf, 16 pages.

European Search Report for appplication No. 10781338.8 [PCT/US2010/036720] dated Feb. 20, 2014, 7 pages.

Gelas, et al., "Synthese du 4-oxo et de 4-hydroxy-3,6,8-trioxabicyclo[3.2.1]octanes," Carbohydrate Research 30(1): 21-34 (1973) (with English abstract).

Girisuta, et al., "Green Chemicals a Kinetic Study on the Conversion of Glucose to Levulinic Acid," Chemical Engineering Research and Design 84(A5) 339-349 (2006).

Haskelbhrg, L., "The preparation of glycerol esters of amino acids," Compt. rend. 190270-190272 (1930).

Hegde, et al., "The Kinetics and Thermodynamics of Bicyclic Ketal Formation: An Application to the Synthesis of the Zaragozic Acids," Tetrahedron 53(32): 11179-11190 (1997).

Hexyl CELLOSOLVE(R) Solvent, DOW Technical Data Sheet, 3 pages (2012).

Holmberg, Krister, "Surfactants with controlled half-lives", Current Opinion in Colloid & Interface Science, vol. 1, Issue 5, p. 572-579 (Oct. 1996).

Horsfall, et al., "Fungitoxicity of Dioxanes, Dioxolanes, and Methylenedioxybenzenes," The Connecticut Agricultrual Experiment Station New Haven, Bulletin 673: pp. 1-44, Jun. 1965.

International Search Report of the International Searching Authority for PCT/US2013/060883 (SGT0061PCT) mailed Dec. 13, 2013, 5 pages.

Lukes, Robert M., Preparation of Methyl Esters Containing the 1,3-Dioxane or 2,4,8,10-Tetroxaspiro[5.5]undecane Structure by Ketal Exchange, 26: 2515-2518 (1961).

Meltzer, et al., "2,2-Disubstituted 1,3-Dioxolanes and 2,2-Disubstituted 1,3-Dioxanes," JOC 25: 712-715 (1960).

Meskens, Frans A.J., "Methods for the Preparation of Acetals from Alcohols or Oxiranes and Carbonyl Compounds," Synthesis 501-522 (1981).

Nakamura et al. "Study on Ketalization Reaction of Poly(vinyl alcohol) by Ketones.IX.Kinetic Study on Acetalization and Ketalization Reaction of 1,3-Butanediol as a Model Compound for Poly(vinyl alcohol)",J.Polym.Sci A: Polym Chem35, pp. 1719-1731, 1997.

Newman et al., "Kinetic and Equilibrium Studies of Cyclic Ketal Formation and Hydrolysis", J. Am. Chem. Soc., 1958, 80 (23), pp. 6350-6355.

Olson, Edwin S., "Subtask 4.1—Conversion of Lignocellulosic Material to Chemicals and Fuels," Final Report for U.S. Dept. of Energy, National Energy Technology Laboratory, Cooperative Agreement No. DE-FC26-98FT40320 (Jun. 2001) 16 pages.

Ono, et al., "Synthesis and Properties of Soap Types of Cleavable Surfactants Bearing a 1,3-Dioxolane Ring Derived from Long-chain Epoxides and Ethyl Levulinate," J. Jpn. Oil Chem. Soc. 42(12): 965-971 (1993).

(56) References Cited

OTHER PUBLICATIONS

Otera, Junzo, "Esterification, Methods, Reactions, and Applications," Wiley-VCH Verlag GmbH & Co., 1-19 (2003).
STIC Search Report dated Jul. 5, 2013, 90 pages.
Transmittal of International Preliminary Report on Patentability and Written Opinion for PCT/US2010/036720, mailed Dec. 8, 2011, 11 pages.
Wedmid et al., "Long-Chain Stereomeric 2-Alkyl-4-methoxycarbonyl-1,3-dioxolanes in Glycerol Acetal Synthesis", J. Org. Chem. 42(22), (1977), pp. 3624-3626.
Written Opinion of the International Searching Authority for PCT/US2013/060883 (SGT0061PCT) mailed Dec. 13, 2013, 8 pages.
Yamaguchi, "Synthesis of polycyclic aromatic compounds via polyketides", Yuki Gosei Kagaku Kyokaishi, vol. 45, No. 10, (1987), pp. 969-982, with English Abstract.
Yang et al., "Investigation of homopolymerization rate of perfluoro-4,5-substituted-2-methylene-1,3-dioxolane derivatives and properties of the polymers", Journal of Flourine Science 127, (2006), pp. 277-281.
Yu, et al., "Polymer blends and composites from renewable resources," Prog. Polym. Sci. 31: 576-602 (2006).
Zhang et al., "Synthesis of Ketals of 4-Oxopentanoates," Lanzhou Daxue Xuebao, Ziran Kexueban 30(2), (1994), pp. 66-70, with English Abstract.
Zhang, Yulan; et al., "Synthesis of Ketals of 4-Oxopentanoates," Lanzhou Daxue Xuebao, Ziran Kexueban 30(2): 66-70 (1994).
IPRP, Issued Feb. 4, 2015, SGT0061PCT.

* cited by examiner

CLEANING, SURFACTANT, AND PERSONAL CARE COMPOSITIONS

This application is a National Stage filing of International Application No. PCT/US2013/060883 filed on Sep. 20, 2013, which claims the benefit of U.S. Provisional patent application Serial No. 61/704,182, filed on Sep. 21, 2012, both of which are incorporated by reference in their entirety herein.

BACKGROUND

This disclosure relates to solvents containing 1,4-pentanediol or ketals having at least one hydroxyl group and their use in a variety of compositions, including cleaning compositions, coating compositions, such as paints and water reducible coatings, stripper and removal compositions, fragrance and personal care compositions, as well as surfactant compositions.

Many formulations make use of certain solvents or co-solvents to enhance their performance resulting from the solvents' ability to either act as soil dissolution aid and/or to aid in the rapid dispersion of actives or surfactants employed for the desired behavior. Such molecules are also called "coupling solvents" or "hydrotropes." In practice, solvent selection is guided by considerations such as solubility, solubilization activity, reactivity, volatility, toxicity, environmental profile, and cost.

SUMMARY

In one aspect, the present invention is directed to a compound of the formula

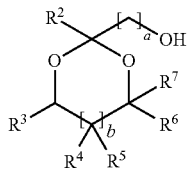

wherein
  $R^2$ is hydrogen or C1-3 alkyl,
  each $R^3$, $R^4$, and $R^5$ is independently hydrogen or C1-6 alkyl,
  $R^6$ and $R^7$ are each independently hydrogen, C1-6 alkyl optionally substituted with at least one hydroxyl groups,
  a=1-6, and
  b=0-2.

In another aspect, a cleaning or personal care composition according to this disclosure can comprise a cleaning or personal care component, and at least one of 1,4-pentanediol and a ketal alcohol of formula (1):

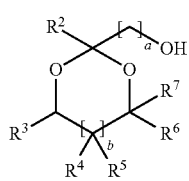

(1)

wherein
  $R^2$ is hydrogen or C1-3 alkyl,
  each $R^3$, $R^4$, and $R^5$ is independently hydrogen or C1-6 alkyl,
  $R^6$ and $R^7$ are each independently hydrogen, C1-6 alkyl optionally substituted with at least one hydroxyl group,
  a=1-6, and
  b=0-2.

A method of manufacture of the cleaning or personal care formulation comprises combining a cleaning or personal care component, and at least one of 1,4-pentanediol and a ketal alcohol of formula (1).

In another aspect, a composition according to this disclosure can comprise a surfactant, and at least one of 1,4-pentanediol and a ketal alcohol of formula (1):

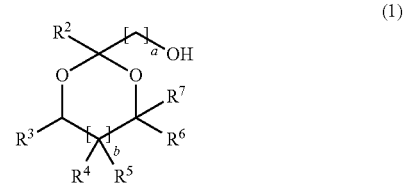

(1)

wherein
  $R^2$ is hydrogen or C1-3 alkyl,
  each $R^3$, $R^4$, and $R^5$ is independently hydrogen or C1-6 alkyl,
  $R^6$ and $R^7$ are each independently hydrogen, C1-6 alkyl optionally substituted with at least one hydroxyl group,
  a=1-6, and
  b=0-2.

In another aspect, a water-reducible coating composition according to this disclosure comprises a water-reducible polymer binder, water; and 1,4 pentanediol or a ketal alcohol of formula (1)

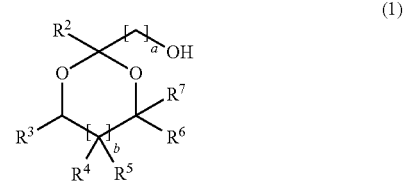

(1)

wherein
  $R^2$ is hydrogen or C1-3 alkyl,
  each $R^3$, $R^4$, and $R^5$ is independently hydrogen or C1-6 alkyl,
  $R^6$ and $R^7$ are each independently hydrogen, C1-6 alkyl optionally substituted with at least one hydroxyl groups,
  a=1-6, and
  b=0-2.

In another aspect, a latex coating composition according to the disclosure comprises a latex polymer binder, water, and 1,4 pentanediol or a ketal alcohol of formula (1)

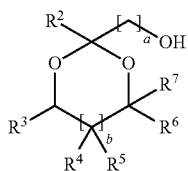

(1)

wherein
R² is hydrogen or C1-3 alkyl,
each R³, R⁴, and R⁵ is independently hydrogen or C1-6 alkyl,
R⁶ and R⁷ are each independently hydrogen, C1-6 alkyl optionally substituted with at least one hydroxyl groups,
a=1-6, and
b=0-2.

In another aspect, a dispersion according to the disclosure comprises a liquid or semi-solid continuous phase, a dispersed solid phase comprising a plurality of organic, inorganic or inorganic-organic particles, and 1,4 pentanediol or a ketal alcohol of formula (1)

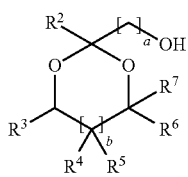

(1)

wherein
R² is hydrogen or C1-3 alkyl,
each R³, R⁴, and R⁵ is independently hydrogen or C1-6 alkyl,
R⁶ and R⁷ are each independently hydrogen, C1-6 alkyl optionally substituted with at least one hydroxyl groups,
a=1-6, and
b=0-2.

In another aspect, a fragrant formulation according to the disclosure comprises at least one fragrant composition; and 1,4 pentanediol or a ketal alcohol of formula (1)

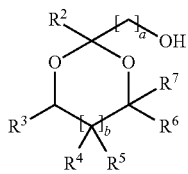

(1)

wherein
R² is hydrogen or C1-3 alkyl,
each R³, R⁴, and R⁵ is independently hydrogen or C1-6 alkyl,
R⁶ and R⁷ are each independently hydrogen, C1-6 alkyl optionally substituted with at least one hydroxyl groups,
a=1-6, and
b=0-2.

In another aspect a process to prepare a ketal alcohol of formula (1)

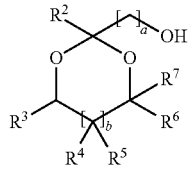

(1)

wherein
R² is hydrogen or C1-3 alkyl,
each R³, R⁴, and R⁵ is independently hydrogen or C1-6 alkyl,
R⁶ and R⁷ are each independently hydrogen, C1-6 alkyl optionally substituted with at least one hydroxyl groups,
a=1-6, and
b=0-2, comprises the steps of providing an ester ketal of formula (2).

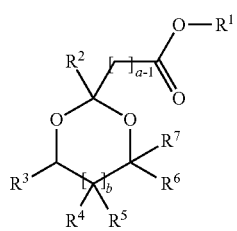

(2)

wherein R¹ is hydrogen or a C1-C5 alkyl group, and R², R³, R⁴, R⁶, and R⁷, and a and b are as defined in formula (1), and hydrogenating the ester ketal with a metal based catalyst and hydrogen gas under reaction conditions.

In another aspect, a process to purify a composition comprising a ketal alcohol of formula (1)

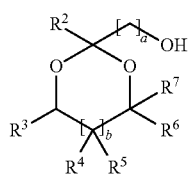

(1)

wherein
R² is hydrogen or C1-3 alkyl,
each R³, R⁴, and R⁵ is independently hydrogen or C1-6 alkyl,
R⁶ and R⁷ are each independently hydrogen, C1-6 alkyl optionally substituted with at least one hydroxyl groups,
a=1-6, and
b=0-2 comprises the steps of providing the composition comprising the ketal alcohol and performing vacuum distillation until the composition comprises greater than 90% of the ketal alcohol.

The above described and other embodiments are further described by the drawings, detailed description, and claims.

DETAILED DESCRIPTION

Figure 1:
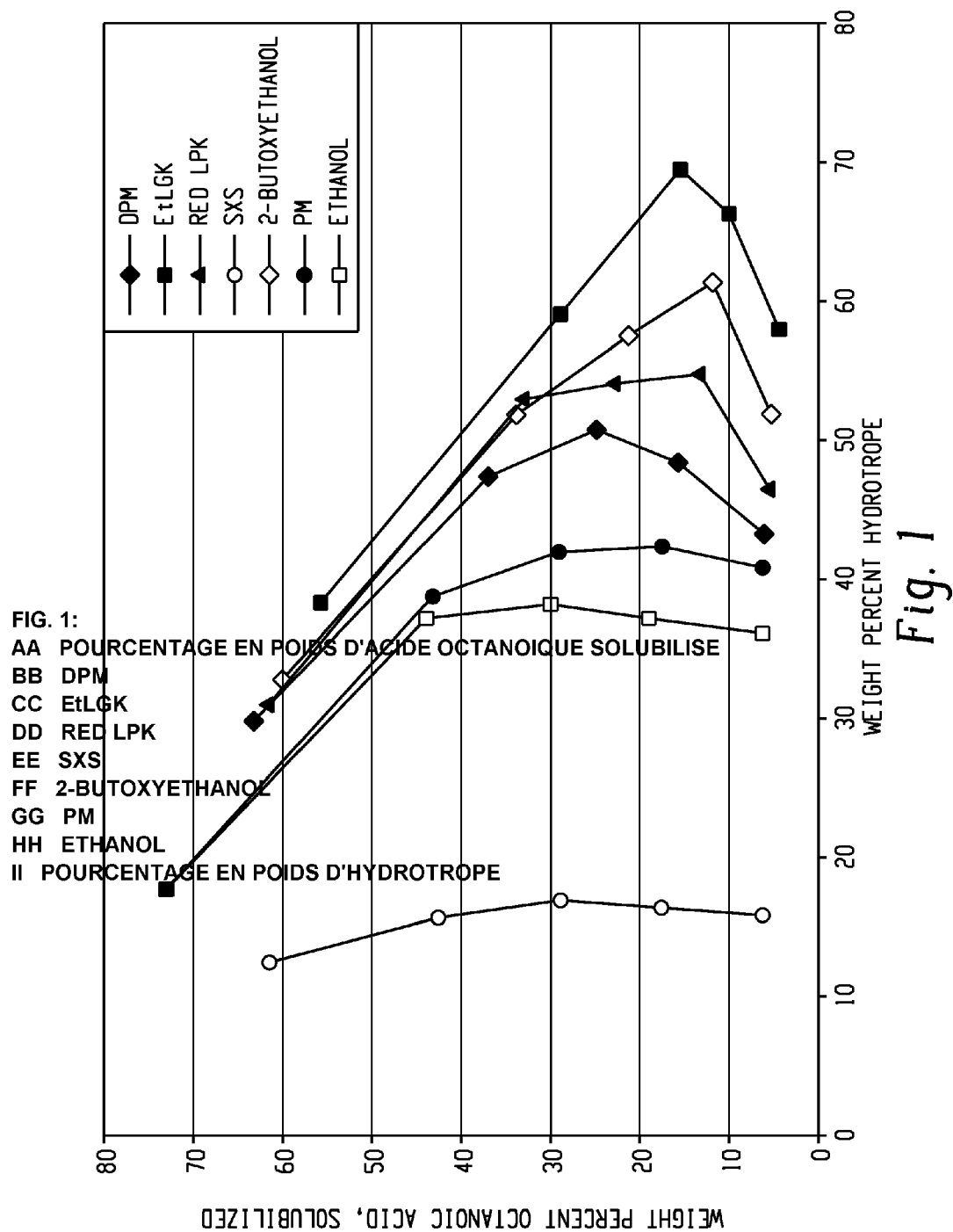
FIG. 1 illustrates the effects of various hydrotropes on the solubility of octanoic acid in water.

While a number of solvents for cleaning and personal care compositions are available and in commercial use, there remains a need in the art for new solvents that offer a favorable combination of solubility, solubilization activity, reactivity, volatility, toxicity, environmental profile, and cost.

In addition, since many cleaning and personal care formulations are maintained at basic pH, there is a need for solvents that are chemically and thermally stable under basic conditions.

Further, there is an increasing need for "bio-sourced" solvents that can be used as replacements for petroleum-sourced solvents. Few bio-sourced solvents are available that can meet the increasingly demanding technical requirements for cleaning and personal care compositions. Even where such solvents are available, the solvents can have various drawbacks. For example, d-limonene, which has been used as a replacement for chlorinated solvents in degreasing applications, has a strong odor, is combustible, and is classified as an irritant and sensitizer. Similarly, ethanol is a versatile solvent that is readily available from bio-based sources, but its high flammability limits its use in solvent applications. A further drawback of these solvents is that the chemical and physical properties of the solvents can only be adjusted to a limited extent.

There accordingly remains a need in the art for alternative solvents for cleaning and personal care compositions, in particular bio-sourced solvents that offer an advantageous combination of solubilization activity with one or more of reactivity, stability under basic conditions, volatility, toxicity, environmental profile, and cost. It would be further advantage if such solvents could be readily modified to adjust the chemical and physical properties of the solvent to meet the needs of a specific application. It would be advantageous if the bio-sourced solvents provided cleaning and personal care compositions that meet one or more customer needs such as good viscosity, low odor, high solubilization, low toxicity, and long shelf life.

The inventors hereof have discovered that 1,4-pentanediol and certain ketals containing at least one hydroxyl group offer a combination of properties that make them useful in a broad variety of cleaning and personal care compositions. In particular, 1,4-pentanediol and certain ketals containing at least one hydroxyl groups are excellent solvents for a wide range of materials, including active agents useful in cleaning and personal care formulations. Many of the ketals are at least partially miscible with water or other organic solvents, or both. In addition, 1,4-pentanediol and the ketals have low volatility. Under normal conditions of manufacture, storage, and use, they are not reactive with many of the other materials that are commonly found in personal care formulations. A further advantage is that 1,4-pentanediol and the ketals are stable under basic conditions. Moreover, certain ketals can be derived from biological feedstocks.

The ketals containing at least one hydroxyl group, which are sometimes referred to herein as "ketal alcohols" have the general formula (1):

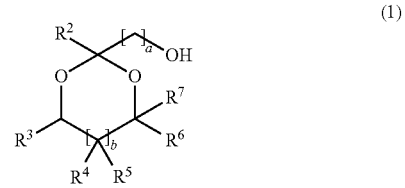

(1)

wherein
$R^2$ is hydrogen or C1-3 alkyl,
each $R^3$, $R^4$, and $R^5$ is independently hydrogen or C1-6 alkyl,
$R^6$ and $R^7$ are each independently hydrogen, C1-6 alkyl optionally substituted with at least one hydroxyl groups,
a=1-6, more specifically, 2-6, more specifically, 2-5, more specifically 2-4, more specifically, 2-3, more specifically 3-6, more specifically, 3-5, and more specifically 3, and
b=0-2.

More specifically, $R^2$ is methyl, $R^3$, $R^4$, and $R^5$ are each independently hydrogen or C1-3 alkyl, $R^6$ is hydrogen, C1-3 alkyl, or —CH$_2$OH, $R^7$ is hydrogen, a=1-4, and b=0-1.

Even more specifically $R^2$ is methyl, $R^3$ is hydrogen, $R^6$ is hydrogen, C1-3 alkyl, or —CH$_2$OH, $R^7$ is hydrogen, a=2-3, and b=0.

In a specific embodiment $R^2$ is methyl, $R^3$ is hydrogen, $R^6$ is hydrogen, methyl, ethyl, or —CH$_2$OH, $R^7$ is hydrogen, a=3, and b=0.

Still more specifically, the ketal alcohol is of formula (1a) or formula (1b), or a combination thereof.

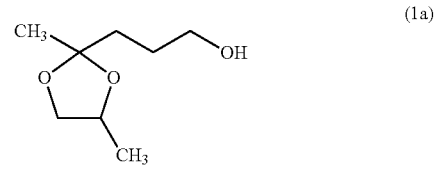

(1a)

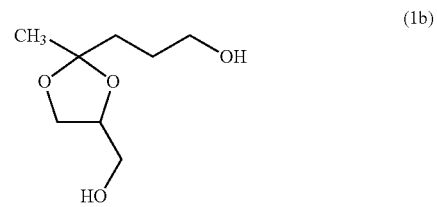

(1b)

The ketal alcohol of formula (1) can be obtained by the reduction of the corresponding ketal ester (2)

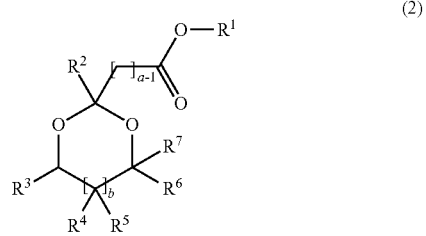

(2)

wherein $R^1$ is hydrogen or a C1-C5 alkyl group, and $R^2$, $R^3$, $R^4$, $R^6$, and $R^7$, and a and b are as defined in formula (1). Reduction can be carried out, for example, by a hydride such as LiBH$_4$ or LiAlH$_4$. Alternatively, ketal alcohol (1) can be obtained by reducing ketal ester (2) under catalytic hydrogenation conditions. Exemplary catalysts for the hydrogenation include homogeneous ruthenium catalysts, heterogenous ruthenium catalysts, heterogenous copper containing catalyst, and copper chromite catalyst. Ketal ester (2) can be obtained by the acid-catalyzed reaction of a ketoalcohol of formula (3) with a polyol of formula (4):

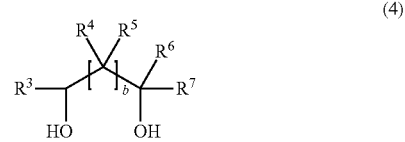

wherein R$^1$ is hydrogen or an alcohol protecting group selectively removable in the presence of a ketal group, and R$^2$, R$^3$, R$^4$, R$^6$, and R$^7$, and a and b are as defined in formula (1). Reaction conditions for ketalization are described in WO 09/032905, for example. Alternatively, the ketal alcohols of formula (1) can be obtained by the acid-catalyzed reaction of a ketoalcohol of formula (5) with a polyol of formula (6)

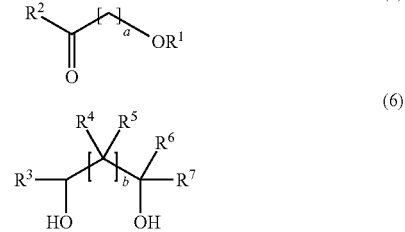

wherein R$^1$ is hydrogen or an alcohol protecting group (which is subsequently removed), and R$^2$, R$^3$, R$^4$, R$^6$, and R$^7$, and a and b are as defined in formula (1). Many of the compounds falling within the scope of formulae (2), (3), (4), (5), and (6) can be bio-sourced. The ketal alcohols thus provide an entry point for a broad variety of bio-sourced solvents. For example, levulinic acid is produced by the thermochemical treatment of various carbohydrates such as cellulose; subsequent esterification with bio-sourced alkanols and ketalization of the levulinate ester with polyhydroxy compounds such glycerol or propylene glycol produces a ketal ester, which can be hydrogenated to provide a bioderived solvent.

In a highly advantageous feature, selection of each of the specific R$^2$, R$^3$, R$^4$, R$^6$, and R$^7$ groups and a and b in the ketal alcohols of formula (1) allows the chemical and physical properties of the ketal alcohols to be adjusted to achieve the desired combination of properties, for example, solubilizing activity, and volatility. The ability to adjust each of these features using a single scaffold provides greater flexibility in designing solvents that achieve the technical requirements of cleaning and personal care compositions. Thus, in a specific embodiment each of the specific R$^2$, R$^3$, R$^4$, R$^6$, and R$^7$ groups and a and b are selected to provide a desired solubilizing activity, that is, the ability of the ketal alcohol to solubilize a solute.

The ketal alcohols (1), specifically (1a) and (1b), are further advantageous due to their low volatility, which can be especially desirable for cleaning applications such as paint and graffiti removal where rapid volatilization of the remover formulation necessitates re-application of the product. Volatility manifests itself in a number of key properties for solvents, including boiling point, vapor pressure, relative evaporation rate, flammability, odor, and volatile organic compound (VOC) content. The desired volatility profile of a solvent varies considerably by application, and there are often conflicting considerations. For instance, highly volatile process solvents require less energy to remove after use, but in many cases also require special handling due to higher flammability. Appropriate selection of each of the specific R$^2$, R$^3$, R$^4$, R$^6$, and R$^7$ groups and a and b can further provide a selected volatility.

Cleaning Compositions and Surfactant Compositions

As stated above, in some embodiments, 1,4-pentanediol and the ketal alcohols (1), such as (1a), (1b), or a combination comprising at least one of the foregoing are useful in cleaning compositions. Exemplary cleaning compositions include but are not limited to laundry detergents, dishwasher cleaning formulations, hard surface cleaners, soft surface cleaners, glass cleaner compositions, and oven cleaners. Exemplary cleaning compositions also include stripping and removal compositions such as formulations for paint stripping, graffiti removal, ink cleaning and removal, adhesive removal, mastic removal, photoresist removal, wax stripping, asphalt removal, concrete cleaning, form cleaning, mold cleaning, hand cleaning, body cleaning, sap/pitch removal, oil stain cleaning and removing, parts degreasing, and engine degreasing. The 1,4-pentanediol and ketal alcohols have excellent combination of properties for use in these applications, including solubilizing activity, low flammability, long work times, biodegradability, non-corrosiveness, and low odor. The cleaning compositions can be in the form of a solid, a gel, a liquid, an emulsion. A single composition can have more than one use, for example a single composition can be used as both a paint and ink remover, as a paint, oil, and grease remover.

In an embodiment, the cleaning compositions contain only 1,4-pentanediol, the ketal alcohol (1), specifically (1a), (1b), or a combination comprising at least one of the foregoing, and 0 to 1 wt. % water, based on the total weight of the removal compositions. Such cleaning compositions can be removal compositions, for example, a paint remover, graffiti remover, ink remover, adhesive remover, mastic remover, photoresist remover, wax remover, asphalt remover, concrete cleaner, form cleaner, sap remover, oil remover, or grease remover.

In another embodiment, the cleaning compositions comprise 1,4-pentanediol, the ketal alcohol (1), specifically (1a), (1b), or a combination comprising at least one of the foregoing; 0 to 1 wt. % water, based on the total weight of the removal composition; and one or more additional components, for example a cosolvent and/or other components such as a plurality of abrasive particles, an organic amine, antioxidant, biocide, colorant, corrosion inhibitor, defoamer, dye, enzyme, light stabilizer, odor masking agent, plasticizer, preservative, rust inhibitor, surfactant, thickener, or a combination comprising at least one of the foregoing.

In still another embodiment, the cleaning compositions comprise from 20 to 99 wt. %, of water, from 0.1 to 40 wt. % of 1,4-pentanediol, ketal alcohol (1), specifically (1a), (1b), or a combination comprising at least one of the foregoing, and from 0.1 to 20 wt. % of at least one surfactant. In yet another embodiment, the cleaning compositions comprise from 20 to 99 wt. %, of water, from 0.1 to 40 wt. % of 1,4-pentanediol, ketal alcohol (1), specifically (1a), (1b), or a combination comprising at least one of the foregoing, and from 0.1 to 45 wt. % of at least one surfactant and one or more additional components, for example a cosolvent and/or other components such as a plurality of abrasive particles, an organic amine, antioxidant, biocide, colorant, corrosion inhibitor, defoamer, dye, enzyme, light stabilizer, odor masking agent, plasticizer, preservative, rust inhibitor, surfactant, thickener, soil suspending agent, builder or chelating agent, bleach, bleach activator, bleach stabilizer, and pH control agent, hydrotrope, and fabric softening ingredient.

Exemplary cosolvents include:

aliphatic hydrocarbons, for example C6-30 straight, branched-chain, or cyclic aliphatic hydrocarbons, that are specifically liquid at ambient temperatures and have a boiling point of at least about 100° C., e.g., mineral oil (also referred to as liquid petrolatum or liquid paraffin), mineral spirits (also referred to as ligroin or petroleum spirits), and low flashpoint cuts of hydrocarbon distillates (e.g., Conosol® C-145 (primarily of C10-13 cycloparaffinic and isoparaffinic hydrocarbons), Conosol® C-170 (composed primarily of C10-15 cycloparaffinic and isoparaffinic hydrocarbons), Conosol® C-200 (a composed primarily of C12-16 cycloparaffinic and isoparaffinic hydrocarbons), and Conosol® 215 (composed primarily of C12-15 cycloparaffinic and isoparaffinic hydrocarbons), from Calumet Specialty partners);

aromatic hydrocarbons, for example naphthalene, C1-8 alkyl derivatives of benzene, and C1-8 alkyl derivatives of naphthalene, specifically toluene, xylene (o, m, or p), cumene, ethyl benzene, mesitylene, durene, sec-amylbenzene, n-butylbenzene, naphthalene, and methyl naphthalene;

terpenes, for example, turpentine, alpha-pinene, beta-pinene, and d-limonene;

organic sulfur-containing compounds such as sulfoxides, for example dimethyl sulfoxide (DMSO);

chlorinated solvents, for example chlorinated C1-6 aliphatic compounds such as allyl chloride, carbon tetrachloride, chloroform, 1,1-dichloroethane, dichloroethylether, 1,2-dichloroethylene, dichloroisopropyl ether, ethyl chloride, ethylene dichloride, isopropyl chloride, methyl chloride, perchloroethylene, propylene dichloride, 1,1,2-trichloroethane, trichloroethylene 1,2,3 trichloropropene, and methylene chloride (dichloromethane, or DCM);

alcohols, for example amyl alcohol, n-butanol, 3-butoxyethyl-2-propanol, benzyl alcohol, benzyloxyethanol, diethoxyethanol, diisobutyl carbinol, dimethyl heptanol, ethanol, 2-ethylhexanol, ethylene glycol, glycerin, 1-hexanol, isobutanol, isopropanol, methanol, methyl amyl alcohol, 2-methyl-1-butanol, 1-pentanol, 1-propanol, propylene glycol, and 2,2,4-trimethyl-1,3-pentanediol monoisobutyrate (commercially available as UCAR FILMER™ IBT from Dow Chemical Co.);

glycol ethers, for example diethylene glycol methyl ether, diethylene glycol mono-n-butyl ether (commercially available as Butyl CARBITOL from Dow), diethylene glycol monoethyl ether (commercially available as CARBITOL from Dow), diethylene glycol monohexyl ether (commercially available as Hexyl CARBITOL from Dow), diethylene glycol monomethyl ether (commercially available as Methyl CARBITOL from Dow), diethylene glycol monopropyl ether (commercially available as Propyl CARBITOL from Dow), diethylene glycol n-butyl ether acetate (commercially available as Butyl CARBITOL™ Acetate from Dow), dipropylene glycol monobutyl ether (commercially available as DOWANOL™ DPnB from Dow), dipropylene glycol monomethyl ether (commercially available as DOWANOL DPM from Dow), dipropylene glycol monopropyl ether (commercially available as DOWANOL DPnP from Dow), dipropylene glycol tert-butyl ether, ethylene glycol methyl ether acetate (commercially available as Methyl CELLOSOLVE Acetate from Dow), ethylene glycol monobutyl ether (commercially available as Butyl CELLOSOLVE from Dow), ethylene glycol monohexyl ether (commercially available as Hexyl CELLOSOLVE from Dow), ethylene glycol monopropyl ether (commercially available as Propyl CELLOSOLVE from Dow), ethylene glycol n-butyl ether acetate (commercially available as Butyl CELLOSOLVE Acetate from Dow), ethylene glycol phenyl ether (commercially available as "DOWANOL™ EPh" from Dow), heptaethylene glycol monobenzyl ether, heptaethylene glycol monophenyl ether, hexaethylene glycol monobenzyl ether, hexaethylene glycol monophenyl ether, pentaethylene glycol monobenzyl ether, pentaethylene glycol monophenyl ether, propylene glycol ethyl ether, propylene glycol methyl ether acetate (commercially available as DOWANOL™ PMA from Dow), propylene glycol monobutyl ether (commercially available as DOWANOL PnB from Dow), propylene glycol monomethyl ether (commercially available as DOWANOL PM from Dow), propylene glycol monopropyl ether (commercially available as DOWANOL PnP from Dow), propylene glycol phenyl ether (commercially available as "DOWANOL PPh" from Dow), tetraethylene glycol monobenzyl ether, tetraethylene glycol monophenyl ether, triethylene glycol methyl ether, triethylene glycol monobenzyl ether, triethylene glycol monophenyl ether, tripropylene glycol methyl ether (commercially available as DOWANOL TPM from Dow), and tripropylene glycol n-butyl ether (commercially available as DOWANOL TPnB from Dow);

water-soluble ethoxylates of propylene glycol monophenyl ether (specifically, containing an average of at least 2 oxyethylene moieties per molecule);

water-soluble or water-dispersible polymeric amines such as poly(ethylene imine);

amides such as acetamidophenol, N,N-dimethyl formamide (DMF), and acetanilide, and cyclic amides such as 1-methyl-2-pyrrolidone (NMP), N-ethyl-2-pyrrolidone, N-isopropyl-2-pyrrolidone, N-cyclohexyl-2-pyrrolidone, 2-hydroxyethyl-2-pyrrolidone, N-dimethylaminopropyl-2-pyrrolidone, vinyl-pyrrolidone, and 2-pyrrolidone;

amines such as 2-(2-aminoethoxy)ethanol, 2-acetyl-1-methylpyrrole, 2-amino-2-methyl-1-propanolalkanolamines (e.g., n-butyldiethanolamine, diethanolamine, diisopropanolamine, dimethylethanolamine, ethanolamine, isopropanolamine, methylisopropanolamine, phenyl diethanolamine, and triethanolamine), cyclic amines (e.g., N-methyl pyrrolidine, N-methylpyyrrole, morpholine, and oxazolidines), n-butylaminoethanol, diethylaminoethanol, diglycolamine, 2-methylaminoethanol, and trialkylamines (e.g. triethylamine);

ketones and cyclic ketones such as isobutyl heptyl ketone, isophorone, methyl ethyl ketone, methyl isobutyl ketone, diisobutyl ketone, diacetone alcohol, acetophenone, methyl n-amyl ketone, cyclohexanone, and cycloheptanone;

dialkyl carbonates such as dimethyl carbonate, diethyl carbonate, dipropyl carbonate, diisopropyl carbonate, and dibutyl carbonate;

cyclic carbonates such as propylene carbonate and ethylene carbonate;

monoesters such as amyl acetate, benzyl acetate, benzyl benzoate, butyl acetate, ethyl acetate, ethyl propionate, ethyl lactate, isobutyl acetate, isopropyl acetate, n-butyl propionate, n-pentyl propionate, n-propyl acetate, n-propyl propionate, butyl lactate, the C1-4 alkyl esters of C6-22 saturated or unsaturated carboxylic acids, such as the methyl ester of C6-14 unsaturated fatty acids; the glycerol ester of fatty acids, including those derived from vegetable oils such as linseed, coconut, palm, soybean, cottonseed, groundnut, sunflower, rape, sesame, olive, corn, safflower, palm kernel, castor oil, peanut, fish, lard, mustard seed, poppyseed, turpentine, and tall oil, and ethyl 3-ethoxypropionate (commercially available as UCAR™ Ester EEP from Dow Chemical Co.);

dibasic esters such as dimethyl adipate, dimethyl succinate, dimethyl glutarate, dimethyl malonate, diethyl adipate, diethyl succinate, diethyl glutarate, dibutyl succinate, dibutyl glutarate and products available under the trade designations DBE™, DBE-3, DBE-4, DBE-5, DBE-6, DBE-9, DBE-IB, and DBE-ME from Invista;

alkoxylated aromatic alcohols as described in U.S. Pat. No. 7,179,775, in particular the alkoxylated aromatic alcohols containing at least one aromatic ring per molecule and alkoxylate units of general formula —$(CR^1R^3—CR^2R^4—O)_n$—$R^5$ wherein: $R^1$, $R^2$, $R^3$, and $R^4$ are each independently hydrogen or methyl; $R^5$ is hydrogen, a C1-6 alkyl, or phenyl; and n is 2-10, wherein the alkoxylate units are attached to the aromatic ring directly or through an ether (oxygen) linkage or an oxymethylene (—$CHR^8O$—) linkage, wherein $R^8$ is hydrogen or C1-4 alkyl. A combination comprising any one or more of the foregoing cosolvents can be used.

In an embodiment, the cosolvent is NMP.

The ratio of 1,4-pentanediol/ketal alcohol to cosolvent can vary widely depending on the 1,4-pentanediol/ketal alcohol, the cosolvent, and the intended use, and can be from 1:99 to 99:1, specifically from 10:90 to 90:10, more specifically from 20:80 to 80:20, from 30:70 to 70:30, or from 40:60 to 60:40, all by volume.

It is to be understood that a single additive can have more than one function, and that characterization of an additive as having that function (e.g., as a cosolvent) does not exclude the additive from performing another function. The concentrations of the individual additives of the cleaning compositions can be varied as depending upon components of the cleaning composition, the type of material to be removed, and the rate at which material removal is to be effected. Optimal concentrations for a particular application can be readily determined by a worker skilled in the art using standard experimental methods, and the guidelines provided below.

The organic amine accelerators can include those listed above as cosolvents. Accelerators are believed to accentuate the performance of the composition by chemically attacking the organic binder of a coating and thereby weakening the adhesion and cohesion of the coating. Exemplary amine accelerators include ethanolamine, diethanolamine, ethylenediamine tetraacetic acid, morpholine, triethanolamine, triethylamine, and 2-(N,N'-diethylamino)ethanol). When used as an additive, the amine accelerator can be present in an amount from 0.1 to 20 wt. %, or from 1 to 10 wt. %, although these amounts are merely illustrative.

Exemplary organic acid accelerators include C1-22 carboxylic acids (e.g., formic acid, acetic acid, propionic acid, oleic acid, oxalic acid, and hydroxyacetic acid). When used as an additive, the organic acid accelerator can be present in an amount from 0.1 to 20 wt. %, or from 1 to 10 wt. %, although these amounts are merely illustrative.

Corrosion inhibitors can be present, particularly where the composition is provided in a metal container, or when an acid accelerator is present. Corrosion inhibitors can be, for example, a molecule that has both an oil soluble portion and a water soluble portion, such as an amphoteric surfactant containing an amine functionality in an amount from about 0.05% to about 2 wt. %, specifically about 0.25% to about 1.0%, such as the disodium N-lauryl iminodipropionate esters available as DERIPHAT® amphoteric surfactants from Cognis Corporation. Other corrosion inhibitors include amine soaps of fatty acids and fatty alkanolamides such as the $C_8$ to $C_{18}$ fatty alkanolamides, examples of which include STANDAMID® alkanolamides, available from Cognis Corporation. Such corrosion inhibitors can also be used for post-application anti-corrosion effects on surfaces that will rust or corrode because of the presence of water in the cleaning compositions, such as on metal surfaces such as iron and steel and the like.

The cleaning compositions can also contain an effective amount of odor masking agents, such as essential oils, aroma chemicals, perfumes, and the like, for example, ambergris, borneol and its esters, carvone, castoreum, civet, cinnamaldehyde, citrals, clove oil, galbanum, jasmine, limonene, linalool and its esters, pinenes (alphas, betas, etc.), rosemary oil, sandalwood, terpineols, terpinenes, and the like, benzaldehyde, benzoin, isoamyl acetate (banana); isobutyl propionate (rum); methyl anthranilate (grape); benzyl acetate (peach), dipentene, methyl butyrate (apple); ethyl butyrate (pineapple); octyl acetate (orange); n-propyl acetate (pear); ethyl phenyl acetate (honey), and the like. An effective amount of such odor masking agents will be readily determinable by those skilled in the art, and can be, for example, about 0.25% to about 2.50 wt. % the removal composition specifically about 0.4% to about 1.0%.

Exemplary plasticizers include phthalate esters, for example dibutyl phthalate, diethylhexyl phthalate, and diethyl phthalate; aliphatic diesters, for example dioctyl adipate; terephthalate esters, for example dioctyl terephthalate; citrate esters, for example acetyl triethyl citrate and acetyl tri-n-butyl citrate; ketal based plasticizers, such as those described in PCT Application WO 2010/151558, or a combination comprising at least one of the foregoing. When used, the plasticizer is present in an amount from about 0.1 to about 10 wt. %, based on the total weight of the removal composition.

A wide variety of surfactants can be utilized, depending on the application, and can be amphoteric, anionic, cationic, nonionic, or zwitterionic. A surfactant or combination of surfactants can be present in order to improve wetting of the soil or coating to be removed and to hasten penetration of the active components. In addition, a surfactant can facilitate water rinsing and water clean-up of the substrate after removal of the soil or coating. Exemplary amphoteric surfactants include amine oxide compounds having the formula RR'R"N→O wherein each R, R' and R" is independently a $C_1$-$C_{24}$ alkyl, aryl or arylalkyl group) that can optionally contain one or more P, O, S or N heteroatoms. Exemplary amphoteric surfactants also include betaine compounds of the formula RR'R"N$^+$(CH$_2$)$_n$C(O)O$^-$ wherein each R, R' and R" is independently a $C_1$-$C_{24}$ alkyl, aryl or arylalkyl group) that can optionally contain one or more P, O, S or N heteroatoms and n is about 1 to about 10. A combination comprising at least one of the foregoing can be used.

Exemplary anionic surfactants include the water-soluble salts of alkylbenzene sulfonates such as the isopropylamine salt of a $C_{10-14}$ alkyl benzene sulfonic acid, and/or a $C_{8-14}$ fatty alcohol sulfate, alkyl sulfates, alkyl polyethoxy ether sulfates, paraffin sulfonates, alpha-olefin sulfonates and sulfosuccinates, alpha-sulfocarboxylates and their esters, alkyl glyceryl ether sulfonates, fatty acid monoglyceride sulfates and sulfonates, alkyl phenol polyethoxyether sulfates, the water-soluble salts or esters of alpha-sulfonated fatty acids containing from about 6 to about 20 carbon atoms in the fatty acid group and from about 1 to about 10 carbon atoms in the ester group, and the like. When present, the anionic surfactant can be present in the composition in an amount from about 0.1 to about 15 wt. %, from about 3 to about 12 wt. %, and most specifically from about 5 to about 10 wt. %, based on the weight of the composition. A combination comprising at least one of the foregoing can be used.

In addition to, or instead of an anionic surfactant, a short-chain surfactant can be present, for example $C_3$-$C_6$ alcohols, glycols, glycol ethers such as propylene glycol n-butyl ether, pyrrolidones, glycol ether esters, and the like. A combination comprising at least one of the foregoing can be used.

Exemplary cationic surfactants include quaternary amine compounds having the formula RR'R"R'"N$^+$X where each R, R', R" and R'" is independently a $C_1$-$C_{24}$ alkyl, aryl or arylalkyl group) that can optionally contain one or more P, O, S or N heteroatoms, and X is F, Cl, Br, I or an alkyl sulfate. A combination comprising at least one of the foregoing can be used.

Exemplary nonionic surfactants include alcohol ethoxylates (e.g., $C_6$-$C_{24}$ or $C_6$-$C_{16}$ alcohol ethoxylates) having 1 to about 20 ethylene oxide groups (e.g., about 9 to about 20 ethylene oxide groups), alkylphenol ethoxylates (e.g., $C_6$-$C_{24}$ or $C_8$-$C_{10}$ alkylphenol ethoxylates) having 1 to about 100 ethylene oxide groups (e.g., about 12 to about 20 ethylene oxide groups), alkylpolyglycosides (e.g., $C_6$-$C_{24}$ or $C_6$-$C_{20}$ alkylpolyglycosides) having 1 to about 20 glycoside groups (e.g., about 9 to about 20 glycoside groups). A combination comprising at least one of the foregoing can be used.

As a general guide, the amount of surfactant can be about 0.1 to about 20%, about 0.1 to about 15% or about 2 to about 15% of the total weight of the cleaning composition.

In one embodiment, the invention includes a composition comprising a surfactant as described above and 1,4-pentanediol, the ketal alcohol of formula (1) (specifically 1(a) or 1(b)), or a combination thereof. In these embodiments, the ratio of surfactant to 1,4-pentanediol or ketal alcohol can range from 50:1 to 1:50, preferably 20:1 to 1:10. These compositions can be prepared as intermediates to be used in final formulations, such as for cleaning products.

Thickeners can be present to adjust the rheological properties of the cleaning compositions. For example, the removal of partially dried paint removal from automotive paint spray booths is generally performed by spraying a cleaning composition such as coatings remover onto the spray booth. The coatings remover must be thin enough to spray easily but must rapidly build in viscosity under low shear conditions to effectively cling to vertical surfaces. A higher viscosity formulation is generally desired if the coatings remover is to be painted on while a low viscosity formulation containing no added thickener can be used where the coated substrate is to be soaked in a tank. Thickeners can also serve to increase the effectiveness of the coatings removers by decreasing the rate of evaporation of the volatile components after application to a coated substrate. Use of a thickener in the composition enables the composition to be applied onto vertical surfaces without any attendant dripping or run-off therefrom, and also inhibits dissipation of the composition into porous substrates such as brick or concrete.

Exemplary thickeners are natural or synthetic clays including bentonite, hectorite, smectite and other silicates such as available grades of BENTOLITE™, CLAYTONE™ and GELWHITE™ bentonites, PERMON™ smectites, CLOISITE™ magnesium aluminum silicates, LAPONITE™ silicates and GARAMITE™ silicates (all available from Southern Clay Products, Inc.) and available grades of OPTIGEL™ bentonites, hectorites, smectites and other clays (all from Sued-Chemie Group); stearates of organoclay compounds such as tetraalkyl ammonium bentonite; gums and other polysaccharides such as carrageenan gum (e.g., GENUVISCO™ X-906-02 (from CP Kelco)), cassia gum, diutan gum (e.g., GEOVIS™ XT, KELCO-CRETE™ 80, KELCO-CRETE 200 and KOC617 (all from CP Kelco)), gellan gum (e.g., KELCOGEL™, KELCOGEL F and KELCOGEL LT 100 (all from CP Kelco)), guar gum, Gum Arabic, Gum Tragacanth, locust bean gum, whelan gum and Xanthan gum (e.g., KELZAN™, KELZAN AR, KELZAN ASX, KELZAN ASX T, KELZAN CC, KELZAN HP, KELZAN RD, KELZAN S, KELZAN ST, KELZAN T, KELTROL™, KELTROL T and KELTROL TF (all from CP Kelco) and VANZAN™ and VANZAN D (both from R.T. Vanderbilt Co.)); hydrocolloids such as NOVEGUM™ C865, NOVEGUM C866 and NOVEGUM G888 (all from Noveon, Inc.); alginates such as agar; cellulose ethers such as ethyl cellulose, hydroxyethyl cellulose, ethyl hydroxyethyl cellulose, methyl cellulose, hydroxypropyl cellulose, hydroxypropyl methyl cellulose, and other alkyl or hydroxyalkyl cellulose ethers, commercially available, e.g., as METHOCEL™ K15MDGSE, METHOCEL K4MDGSE, METHOCEL 311, METHOCEL F4M PRG and METHOCEL OS (all from Dow), XDS 8898.5 cellulose ether (from Dow), and KLUCEL™ H, KLUCEL M or KLUCEL G (all from Ashland, Inc.); acrylic acid homopolymers or copolymers, e.g., those which can be neutralized with a salt including associative or non-associative thickeners such as ACUSOL™ 801s, ACUSOL 810, ACUSOL 810A, ACUSOL 820, ACUSOL 823 and ACUSOL 830 acrylate polymers (all from Rohm & Haas Co.) or those which can be crosslinked (e.g., with a polyalkenyl polyether) including CARBOPOL™ 674, CARBOPOL 676, CARBOPOL ETD 2691, CARBOPOL ETD 2623, CARBOPOL EZ-3, CARBOPOL EZ-3A, CARBOPOL EZ-4 and CARBOPOL ULTREZ™ 21 (all from Noveon, Inc.); PEMULEN™ 1622 copolymer (from Noveon, Inc.); polyethylene oxides (e.g., high molecular weight polyethylene oxides) such as polyethylene glycols and methoxypolyethylene glycols; polyvinyl alcohols; polyvinyl pyrrolidone; starches; polyurethanes including RHEOLATE™ 266 (from Elementis Specialties, Inc.), and available grades of OPTIFLO™ associative thickeners (all available from Sud-Chemie Group); and methyl vinyl ether/maleic anhydride copolymers. Other possible thickeners include hydrophobe-modified ethoxy urethane (HEUR) thickeners, hydrophobe-modified alkali soluble emulsion (HASE) thickeners, hydrophobe-modified hydroxyethyl cellulose (HM-HEC) thickeners, and HEURASE combination thickeners. A combination comprising at least one of the foregoing can be used.

The thickener can be used in an amount from about 0.1 to about 30 wt. %, specifically about 2 to about 20 wt. %, and most specifically about 3 to about 10 wt. %, based on the total weight of the cleaning composition.

A detergency builder is commonly present in laundry detergents, hard surface cleaner products and dishwashing liquids, and can be present in cleaning compositions of this disclosure. Examples of such builders include N-diethyleneglycol-N,N-diacetic (DIDA) acid polyphosphates (e.g., potassium pyrophosphate), nitrilotriacetates (e.g., $Na_3NTA$), sodium ethylenediaminetetraacetate (EDTA), sodium ethylenetriaminepentaacetate, sodium citrate, sodium carbonate, sodium metasilicate and zeolites, e.g., zeolites having a cation exchange capacity (measured as $CaCO_3$) of 200 mg or greater per gram of zeolite. Enzymes such as proteases and amylases are also frequently present in cleaner compositions, especially laundry detergent products and prewash products.

The cleaning composition can contain a bleach such as sodium hypochlorite, sodium perborate, diperoxydodecanedioic acid, sodium dichloroisocyanurate, m-chloroperoxybenzoic acid and peroxide based bleaches. An advantage of this disclosure is that the ketal alcohols (1) are stable in bleach solutions, and thus can add good solvency for oily soils into a bleach-containing composition. A bleach-containing composition of the disclosure can also contain one or more bleach activators such as tetra acetyl ethylene diamine and sodium nonanoyloxybenzene sulfonate.

The cleaning composition can further contain one or more soil suspending agents such as sodium carboxymethyl cellulose; one or more bleach stabilizers such as sodium diethylenetriamine-pentamethylenephosphonate and sodium diethyl enetriaminopentaacetate; one or more hydrotropes such as sodium toluene sulfonate, sodium cumene sulfonate and potassium xylene sulfonate; one or more fabric softening ingredients such as smectite clay and tallowdimethylammonium chloride.

In a specific embodiment the cleaning composition is a liquid laundry detergent that may be for hand or machine washing, and which comprises 50 to 95 weight % water; 0.1 to 25 weight % of 1,4-pentanediol, the ketal alcohol of formula (1), or a combination thereof; 0.1 to 45 weight % of a surfactant; and a builder, a chelating agent, a chlorine bleach, a non-chlorine bleach, an abrasive, an anti-deposition agent, a brightening agent, or a combination comprising at least one of the foregoing. In liquid laundry products, the ketal alcohol of formula (1) or 1,4-pentanediol may perform any or all of several functions, such as solubilizing or emulsifying the surfactant or other ingredients and functioning as an active cleaning agent.

For example, a liquid laundry formulation may contain, as percentages of the total formulation weight: a) water: 50-95%; b) ketal alcohol of formula (1), 1,4-pentanediol, or a combination comprising at least one of the foregoing: 0.1-50%, more typically 1-25%, specifically 1-10%; c) one or more surfactant(s): 0.1-45%, specifically 1-40%, more specifically 1-35%, still more specifically 1-10%, but in some cases more specifically from 15-35%; the surfactants advantageously being (1) at least one anionic surfactant, (2) a nonionic surfactant, (3) a mixture of at least one nonionic surfactant and at least one anionic surfactant, (4) one or more of an β alkyl glycoside, an alkyl betaine or a sulfo succinate salt, or (5) a mixture of (4) with (1), (2) or (3); h) one or more builders or chelating agents, particularly a chelating agent such as EDTA or DIDA: 0-30%, specifically, if present, 0.1-30%, more specifically, if present, from 1-25% and still more specifically, if present, from 1-10%; i) one or more bleaches, including, for example, a chlorine bleach such as sodium hypochlorite or a non-chlorine bleach: 0-10%, specifically, if present 0.1-5%; o) one or more abrasives: 0-30% specifically if present 1-20% p) one or more anti-redeposition additives, such as carboxymethylcellulose salts and cellulose acetate polymeric agents, 0-5%, specifically if present 0.1 to 2%; and q) brightening agents, including optical brightening agents, fluorescent brightening agents and fluorescent whitening agents, including, for example, sulfonated triazine-stilbenes, coumarins, imidazolines, diazoles, triazoles, benzoxazolines and biphenyl stilbenes, 0-3, specifically if present 0.1 to 1.

In addition, a liquid laundry product may contain any of optional components for the cleaning compositions as described herein singly or in any combination of any two or more of them. Any or all of optional components may be omitted in any particular liquid laundry formulation.

Some exemplary liquid laundry formulations in accordance with the disclosure follow. The indicated percentages are weight percents based on the total formulation weight. The function of these ketal alcohols of formula (1) or 1,4-pentanediol in liquid laundry formulations is similar to those described before with respect to hard surface cleaners below.

Aqueous Liquid Laundry Detergent
Sodium hydroxide 0-1%
Sodium chloride about 1%
Nonionic surfactant (e.g., ethoxylated alcohol) 0-20, specifically 0.1-6%
Anionic surfactant (e.g., benzenesulfonic acid, alkylated) 1-20, specifically 1-10%
Builder(s) 0-10%
Anti-redeposition agent 0-1%
Proteolytic enzymes 0-2%
Brightener (fluorescing agent) 0-1% Buffer(s) 0-5%
Ketal alcohol or 1,4-pentanediol 0.1-25%
Water (balance of total formulation)
Aqueous Laundry Stain Remover
Proteolytic enzyme 0-<1%
Surfactant 10-20%
Chelating agent 0.5-1.5%
Ketal alcohol or 1,4-pentanediol 1-10%
Water (balance of total formulation)
Aqueous Dry-cleaning Composition
Water 60-95%
Polyacrylates 0.2-0.5%
Mixed glycol ethers 0-30%
Ketal alcohol or 1,4-pentanediol 0.1-25%
Surfactant(s) >0.1%
1,2-octanediol 0-5%

Any of the aforementioned liquid laundry formulations, can be prepared in concentrated form by reducing the amount of water, and correspondingly increasing the concentration of at least the surfactant, and advantageously the concentration of both the ketal alcohol of formula (1) or 1,4-pentanediol and the surfactant. Such a concentrated hard surface cleaner formulation may contain, by weight, up to 50% combined of water and/or volatile organic compound, and more typically contains no more than 40% thereof. Such a concentrated formulation often contains, from 5 to 70% or from 10 to 50% by weight of at least one ketal alcohol of formula (1) or 1,4-pentanediol as described herein and from 5 to 90%, 5 to 70%, or from 10 to 50% by weight of at least one surfactant.

In another specific embodiment the cleaning composition is a hard surface cleaner having a general formulation as is known in the art, and which can be formulated for industrial, institutional, office or, home use. These can be formulated as, for example, general purposes hard surface cleaners, toilet cleaners, shower/bath/tile cleaners, disinfectants, soap scum removers, mildew removers, glass/mirror cleaners, or stain removers. Many of these cleaners are formulated as dilute solutions or emulsions, and many are applied by spraying. A hard surface cleaner can include least 20 wt. %, at least 50 wt. %, or as much as 99 wt. % of water; up to 50 wt. %, 0.1 wt. % to 50 wt. %, 1 wt. % to 25 wt. %, 3 wt. % to 15 wt. %, or 1 wt. % to 10 wt. % of 1,4-pentanediol, a ketal alcohol of formula (1), (1a), (1b), or a combination thereof; and 0.01-40 wt. % of a surfactant, in particular a anionic or nonionic surfactant, each based on the total weight of the composition. The ketal alcohol(s) can perform any or all of several functions, such as (1) soil dissolution and/or removal; (2) compatibilization of ingredients, particularly sparingly water-soluble ingredients into water; (3) formation of a cosolvent mixture in which one or more other ingredients are dissolved or dispersed, (4) elimination or reduction of surfactants and/or organic solvents or others. The surfactant can include one or more materials derived from plant sources, such as one or more alkyl glycosides, an alkyl betaine, or a sulfosuccinate salt.

In specific embodiments, a hard surface cleaner formulation can comprise, as percentages of the total formulation weight: a) water: 20-99%, more typically 50-95%; b) one or more ketal alcohol of formula (1) or 1,4-pentanediol: 1-50%, more typically 1-25% or 1-10%; c) one or more surfactant(s): 0.01-20%, specifically 0.1-15%, more specifically 0.25-10%, still more specifically 1-7% and in some cases 1-5%; the surfactant(s) specifically being (1) at least one anionic surfactant, (2) at least one nonionic surfactant, (3) a mixture of at least one nonionic surfactant and at least one anionic surfactant or nonionic surfactant, (4) one or more of a an alpha, beta-alkyl glycoside, an alkyl betaine or a sulfosuccinate salt, or (4) a mixture of (4) with (1), (2) or (3).

The formulation can also comprise d) one or more propellants, which are generally low-boiling hydrocarbons such as butane, pentane, hexane and cyclohexane or chlorinated and/or fluorinated hydrocarbons that have boiling temperatures of from −10° C. to 50° C.; e) one or more sparingly water-miscible organic solvent(s): generally from 0-10%, specifically, if present, 0.1-5%. This can be, for example, one or more of the long-chain alcohols, glycol ethers, hydrocarbons, halogenated hydrocarbons, Cβ-9 alkyl aromatic compounds, olefins, terpenes, terpene oxides, terpenoids, oils, and natural oil derivatives. The formulation can also comprise f) one or more highly water-miscible organic solvents, such as a lower alcohol (e.g., ethanol and 1-propanol), acetone, glycols, and glycol ethers: 0-10%, specifically, if present, 0.1-5%; g) one or more antimicrobials, 0-5%, specifically, if present 0.1-2%, some examples of include quaternary ammonium chlorides such as C12-16 alkyl dimethyl benzyl ammonium chloride and various phenylphenol compounds; h) one or more builders or chelating agents, particularly a chelating agent such as a phosphate salt, a citrate salt, EDTA, or DIDA: 0-30%, specifically, if present, 0.05-10% and more specifically, if present, from 0.5-1%, still more specifically, if present, from 2-8% and even more specifically, if present, from 2-6%; i) one or more bleaches, including, for example, a chlorine bleach such as sodium hypochlorite or a non-chlorine bleach such as hydrogen peroxide or other peroxy compound: 0-10%, specifically, if present 0.1-5%; j) one or more pH control agent(s) (e.g., acids, bases, pH buffers): 0-2%, if present specifically 0.05 to 1%; k) one or more colorants: 0-5%, specifically if present 0.1-2%; l) one or more inorganic water-soluble salts such as sodium sulfate: 0-10%, specifically if present 0.1-5%; m) one or more viscosity thickeners, including, for example a water-soluble polymer: 0-10%, specifically if present 0.1-5%; n) one or more proteolytic enzymes, 0-5%: specifically if present 0.1-1% o) one or more abrasives; and p) one or more fragrances. Components b) and d)-p) as described above can be present in any combination of any two or more of them. Any or all of components e)-n) can be omitted in any particular hard surface cleaner formulation. Component d) is typically present in a spray cleaner formulation. It is noted earlier that in some instances, a single material can perform multiple functions in a hard cleaner formulation. Component j) is often present to provide for a pH of from 3.5 or higher, specifically from 6 to 10.

A method of preparing a cleaning composition comprises combining 1,4-pentanediol and the ketal alcohols (1), specifically (1a), (1b), or a combination of (1a) and (1b) and any cosolvent or other component to form the cleaning composition. The order of the addition is not particularly limited. The ketal alcohols and additives can be added in any suitable order to the additional component(s) present in the composition to provide the cleaning composition.

When used with cosolvents or other components, the cleaning compositions can be provided as a concentrate. The concentrates are usually diluted in water for use as a working water-based cleaning composition. In an embodiment, a two-part concentrate package can be provided which typically comprises a Part A and a Part B, where each part contains a component likely to react with the other part, for example the ketal and an amine in Part A and an inorganic base in Part B.

The cleaning compositions can alternatively be formulated in other forms useful for removal or cleaning compositions, for example gels, wipes, aerosols, and the like. The removal compositions can be formulated in gel form by the addition of an effective amount of a gelling agent such as fumed silica, organic gums, polymers, copolymers, paraffin wax, bentonite clay, and cellulose ethers such as methyl cellulose and hydroxypropyl methyl cellulose commercially available as METHOCEL® cellulose ethers, from Dow Chemical. Wipes are generally a natural or synthetic fabric piece impregnated with the gel or liquid removal composition. When used as an aerosol, the cleaning formulations are formulated under pressure with a propellant as is known in the art.

A method of cleaning, for example, removing a material such as a coating, soils and/or stains from a substrate comprises contacting the material with a composition comprising 1,4-pentanediol, ketal alcohol (1), specifically (1a), (1b) or a combination comprising at least one of the foregoing under conditions that effect the removal, for example for a time effective to dissolve and/or lift the material; and separating the dissolved and/or lifted material from the substrate. As used herein, "dissolved" includes partial dissolution of a material, often referred to as softening, such that the material can be further removed from the substrate by rinsing or mechanical action. Of course, the cleaning composition can also be at least partially removed by separating the material.

The cleaning compositions can be used to remove a wide variety of materials, generally those soluble or softenable by organic solvents. Examples include materials such as soils, stains, grease, inks for all types of substrates, including paper, wood, plastic, metal, textiles, ceramics, stone, skin, and for indoor or for outdoor use; adhesives and sealants, for example silicone, polyurethane, epoxy, polyvinyl acetate (including copolymers with ethylene), phenolic, amino resin, cyano acrylate, polyester, polyamide, rubber (styrene-butadiene and natural) or acrylic adhesives and sealants; mastics; photoresists; waxes, for example floor wax or bees wax; asphalts; saps (which as used herein includes pitches, rosins, tars, and natural resins such as tree sap); residual materials left in forms or molds, for example polymers such as alkyds, polyacetals, polyacrylates, polyacrylics, polyamides, polycarbonates, polyesters, polyethers, polyethylenes, polyimides, polystyrenes, polyurethanes, polyvinyls, silicones, natural and synthetic rubbers, and the like, and polymer additives; greases, for example silicone and petroleum-based greases; oils, including machine oil; and paints, finishes, and other coatings, for example, alkyd enamels, acrylic enamels, polyesters, polyurethanes, epoxy resin coatings, latex paints, oil-based paints, shellacs, phenolic coatings, gum varnishes, silicone coatings, polyvinyls, polyvinyl cinnamates, polyamides, polyimides, polyalkyl acrylates, polyalkyl methacrylates, drying oils, polyvinyl acrylates, and cellulosic resins.

The substrates that are treated with the cleaning compositions are reasonably resistant to the cleaning compositions, including natural and synthetic fabrics, wood, cardboard, and coated paper, especially if treated with a wax or other protective material, glass, thermoset resins, thermoplastic resins, ceramic, stone, masonry substrates, cement, or metals (e.g., aluminum alloys, zinc alloys, stainless steel, or galvanized steel). The cleaning compositions can further be used to a part of the human body, for example hands or hair, as well as animals.

Although the methods of contacting the surface with the cleaning composition can be accomplished in a number of ways, for example, in aerosol form or other spraying means such as by standard spray nozzles; brush application; dipping; coating; application in gel form such as from a squeeze bottle or brush, and the like, but immersion and spraying can be specifically mentioned. If the surface to be cleaned is readily accessible, then spraying can be used. The spraying pressure will usually be from 1.3 bars to 8.0 bars absolute pressure. The mechanical force of the impinging removal composition facilitates removal of the material. On the other hand, if the surface to be cleaned has recesses or other shapes that are not readily accessible, immersion can be used. Of course, both methods can be used in combination and/or varied in ways apparent to those skilled in the art. During or after contacting, mechanical action, such as scraping, peeling, rubbing, wiping, and the like can be employed to increase contact and/or aid in dissolution and/or lifting.

The contact time needed to produce an effective degree of dissolution and/or lifting of the material from a surface will depend on the nature and thickness of the material, the composition of the cleaning composition, including the ingredient concentrations, the temperature of the composition, and other factors. With some materials and under some conditions, contact times of a few minutes (e.g., 2-3 minutes) to an hour can be sufficient. Operating temperature when using the removal compositions can be from 0 to 180° C. or higher, specifically 15 to 90° C., or 21 to 55° C. The treatment is most conveniently carried out at ambient temperature, but lift time can be shortened as desired by heating the cleaning compositions and/or substrate. Heating can be achieved by local application of heat such as with a heat gun, or more general application of heat, such as with an electric heater, infrared heater, and the like. It is to be understood however, that those skilled in the art can determine optimal conditions for particular removal applications by minimal experimentation. Higher temperatures generally increase the rate at which the material is removed from the surface.

Separating the 1,4-pentanediol and ketal alcohol (1) and dissolved material from the substrate can include mechanical action, such as scraping, peeling, rubbing, wiping, and the like, or rinsing the substrate with additional removal composition or another solvent, including water or aqueous mixture of water with an organic solvent.

Personal Care Compositions

The 1,4-pentanediol and the ketal alcohols (1) are also useful in personal care compositions. As used herein, personal care compositions have a broad scope and include cosmetic (i.e., make-up) compositions. Exemplary personal care compositions include bath or shower products, including various hair and body cleaners; eye care products; cosmetics; a fragrance; treatment formulation, including a hair coloring formulation; a hair straightening or permanent wave formulation; a nail care formulation; an oral hygiene formulation, including toothpaste and mouthwash; a shave cream; a skin care formulation; a sun care formulation; a lip care formulation; an antiperspirant; or a foot care formulation. Personal care compositions are used interchangeably with personal care formulations. It is appreciated that some personal care compositions such as hand cleaning and body cleaning formulations also fall under the scope of cleaning compositions disclosed herein.

The 1,4-pentanediol and the ketal alcohol (1) can be used to enhance the solubility of an active agent in a personal care formulation. Depending on the native solubility of the active agent in the formulation and the type of formulation, the 1,4-pentanediol and ketal alcohol (1) can be used as a cosolvent with water, as a compatibilizer with water and an organic solvent, as a cosolvent with an organic solvent, as an emulsifier, or a combination comprising of any of one or more of the foregoing. As is known to those of skill in the art of formulating personal care products, an individual ingredient can have more than one type of function, for example 1,4-pentanediol and a given ketal alcohol (1) could function both as a cosolvent and as a compatibilizer.

When the active agent has limited water solubility, 1,4-pentanediol and ketal alcohol (1) can in some embodiments function as a cosolvent, together with water. Many ketal alcohol (1) are good solvents for active agents and also have good miscibility in water. The presence of such a ketal alcohol can allow the concentration of the active agent to be increased, often without the presence of volatile organic compounds (VOCs) such as ethanol, isopropanol, acetone, ethyl acetate, and the like in the formulation. The result in some cases can be a more concentrated low VOC formulation. The 1,4-pentanediol and ketal alcohol (1) can also perform additional functions, such as compatibilization of aqueous and organic phases, compatibilization, or solubilization of certain organic materials into an aqueous phase, emulsification of an oil phase into an aqueous phase or of an aqueous phase into an oil phase.

The 1,4-pentanediol and ketal alcohol (1) can act as an emulsifier, compatibilizer, or solubilizer for ingredients other than the active agent, or as a co-emulsifier, co-compatibilizer, or co-solubilizer for ingredients other than the active agent, in particular if the ketal alcohol (1) is highly water-soluble. Moreover, incorporation of the 1,4-pentanediol and ketal alcohol (1) can lead to a lighter, less greasy or heavy-feeling formulation, especially compared to many other naturally-derived ingredients.

In cases in which the active agent is somewhat soluble or highly soluble in an alcohol or alcohol-water mixture, the 1,4-pentanediol and ketal alcohol (1) can in some cases function as a cosolvent, either with the alcohol or with an alcohol-water mixture. The 1,4-pentanediol and ketal alcohol (1) can in some cases permit an increase in the concentration of the active agent in an alcoholic or alcohol-water phase. In other cases, it can permit the proportion of the alcohol in the cosolvent mixture to be decreased, which has the benefit of reducing VOCs in the formulation and in some cases decreasing the drying effect the formulation has on the skin. As with the aqueous systems, the 1,4-pentanediol and ketal alcohol (1) can perform additional functions, such as compatibilization, solubilization, or emulsification. In some cases, the 1,4-pentanediol and ketal alcohol can also lead to a lighter, less greasy or heavy-feeling formulation, as before.

In formulations containing active agents that are oil or oil-soluble and sparingly (if at all) soluble in water, the 1,4-pentanediol and ketal alcohol can in some cases permit the active agent to become dissolved in an aqueous phase, in some cases alone and in other cases in conjunction with one or more other cosolvents. This can in some cases allow a highly water-insoluble active agent to become incorporated into an aqueous-based solution or gel-type form. In some cases, mixtures of ketal alcohols having different solubility/solubilizing characteristics can be present in order to accomplish the dissolution of the active agent. Alternatively (or in addition), the 1,4-pentanediol and ketal alcohol (1) can aid in dissolving or compatibilizing such an active agent into an organic phase, or to help compatibilize or emulsify an organic phase containing the active agent with an aqueous phase, forming in this case an emulsified formulation that can be, for example, a cream or lotion. As before, the 1,4-pentanediol and ketal alcohol (1) in some cases can allow the level of emollient materials to be reduced or improve formulation feel characteristics.

Whether an active agent is present or not, the 1,4-pentanediol and ketal alcohol (1) can in some cases aid mutually incompatible materials to be formulated into a stable formulation form. Thus, the 1,4-pentanediol and ketal alcohol (1) is a valuable ingredient in many emulsified formulations, such as lotions and creams, which include a water-in-oil or oil-in-water emulsion. Also, the 1,4-pentanediol and ketal alcohol (1) in many cases can allow hydrophobic organic ingredients to be dissolved into an aqueous phase to produce clear formulations. In many cases, this can be achieved while reducing or eliminating other ingredients from the formulation. For example, volatile organic compounds or emulsifiers can be eliminated or used in reduced quantities. The presence of the 1,4-pentanediol and ketal alcohol (1) can improve the feel of a personal care, giving the formulated formulation a lighter, less oily feel while preserving its function and performance. In many cases, formulation viscosity is reduced, which can contribute to the lighter and less greasy feel.

Because the ketal alcohol (1) is a good solvent for a wide range of materials, it is very useful for making concentrates, which can be let down into water, an alcohol or other diluent to provide a personal care composition.

Still another benefit of the 1,4-pentanediol and ketal alcohol (1) in some formulations is that it allows the amount of water to be increased in otherwise highly hydrophobic formulations. This can provide a moisturizing function in some cases, or provide other benefits. A notable example of this is in lip care formulations, particularly lipsticks, lip glosses, and lip balms, and cuticle balms which are based on waxes and other highly hydrophobic materials. The 1,4-pentanediol and ketal alcohol (1) permits up to 3%, up to 4%, up to 5%, or up to 10 wt. % water to be included in the lip care or cuticle care formulation, which can allow the lip care or cuticle care formulation to perform a hydrating function.

In one aspect, the personal care composition contains 1,4-pentanediol and ketal alcohol (1), and one or more active agent selected from organic anti-aging agents, organic anti-acne agents, organic skin whitening agents, organic ultraviolet light absorbing agents, organic tanning agents, organic anti-alopecia agents, antifungal agents and/or anti-dandruff agents, antimicrobial agents, organic medicinals, depilatory compounds, hair dyes, or organic insect repellants. In some embodiments, the ketal alcohol (1) forms part of a cosolvent mixture with water or with another organic solvent miscible with the ketal alcohol (1) at the relative proportions thereof that are present in the formulated personal care formulation, and the active agent is dissolved in the cosolvent mixture. The active agents are present in amounts effective to achieve the desired activity, which can vary broadly, depending on the active agent and the product. Thus, an active agent can be present in the formulation in amounts as low as 0.001 wt. %, 0.01 wt. %, or 0.1 wt. %, up to 30 wt. %. The amount of water used in the formulation can also vary widely based on the active agent and the product, from anhydrous products as described above, to products have from 2 to 90%, 80%, 70%, 60%, 50%, 40%, 30%, 20%, or 10 wt. % water, based on the total weight of the formulation.

Thus, in some embodiments, the formulated personal care formulation includes a compound selected from alpha-hydroxy acids such as lactic acid, 2-hydroxydecanoic acid, 2-hydroxyoctanoic acid and glycolic acid, beta-hydroxy acids such as beta-hydroxy salicylic acid, avobenzone, coenzyme Q10, benzoate-4-methylbenzylidene, cinoxate, dioxybenzone, homosalate, menthyl anthranilate, mexoryl SX, drometrizole trisiloxane, octocrylene, octyl methoxycinnamate, ethylhexyl salicylate, oxybenzone, padimate O, p-aminobenzoic acid (PABA), phenylbenzimidazole sulfonic acid, sulisobenzone, titanium trolamine salicylate, salicylic acid, retinoic acid (including the all-trans isomer known as tretinoin), benzoyl peroxide, hydroquinon, arbutun (including plant extracts containing same), kojic acid, azelaic acid, glycyrrhetic acid, levulinic acid, 2-cyano-3,3-diphenylacrylic acid, sodium benzotriazolyl butylphenol sulfonate, ethyl-2-cyan -3,3-diphenylacrylate, 2-t-butyl-6-(5-chloro-2H-benzotriazol-2-yl)-p-cresol, 2-(2-H-benzotriazol-2-yl)-4-methylphenol, benzophenone-12, bornelone, or 2-benzotriazolyl-4-tert-octylphenol. These compounds function as anti-aging, anti-acne, skin whitening and/or UV absorbers; formulations containing them are useful as anti-aging or anti-wrinkle formulations, acne treatments, skin whiteners, and/or sunscreens.

In some embodiments, a personal care formulation includes a tanning agent such as dihydroxyacetone, erythrulose, dihydroxyacetone-ortho-ethyl-acetate, canthaxanthin, or afamelanotide. These compounds function as tanning agents, and personal care formulations containing them in sufficient quantities are effective tanning (skin darkening) formulations.

In some embodiments, the personal care formulation includes a compound selected from minoxidil and 5-alpha reductase inhibitors such as dutasteride and ketoconazole.

These compounds function as anti-alopecia (hair loss prevention) agents; accordingly, personal care formulations containing them are useful in some cases to prevent hair loss.

In some embodiments, a personal care formulation includes a compound selected from zinc pyrithione, selenium sulfide, clotrimazole, tea tree oil, or piroctone olamine. These compounds function as anti-fungal agents, and personal care formulations containing them in sufficient quantities are effective topical anti-fungal treatments (such as for Tinea pedis or Tinea cruris) and/or as anti-dandruff formulations.

In some embodiments, a personal care formulation includes a compound selected from an amphetamine, an antihistamine, methylphenidate, oxymetazoline, tetrahydrolzoline hydrochloride, or psilocybin. These compounds function as vasoconstrictors in some instances and personal care formulations containing them in sufficient quantities are effective as redness reducers (such as in eye drops and anti-redness or anti-puffing creams).

In some embodiments, a personal care formulation includes a compound selected from calcium thioglycolate, sodium thioglycolate, thioglycolic acid, ammonium thioglycolate, butyl thioglycolate, ethanolamine thioglycolate, glyceryl thioglycolate, isooctyl thioglycolate, isopropyl thioglycolate, magnesium thioglycolate, methyl thioglycolate, or potassium thioglycolate. These compounds function to modify hair fibers by breaking S—S bonds in keratin; personal care formulations containing them in sufficient quantities are used in depilatories, permanent waves, relaxers, hair straightening, and hair re-styling formulations.

In some embodiments, a personal care formulation includes a compound selected from aluminum zirconium tetrachlorohydrex gly, aluminum chlorohydrate, or aluminum chloride. These agents are anti-perspirants and personal care formulations containing these are often effective as deodorants and anti-perspirants.

In some embodiments, a personal care formulation includes a compound selected from resorcinol ("resorcin"), 1-napthol, p-aminophenol, p-phenylenediamine (and its salts), 4-amino-2-hydroxytoluene, and the like. These active agents are effective hair dyes; and personal care formulations containing these are often effective as hair colorants or hair colorant concentrates.

In some embodiments, a personal care formulation includes a compound selected from phenoxyethanol, N,N-diethyl-m-toluamide, p-menthane-3,8-diol (active agent in the essential oil of lemon eucalyptus), nepetalactone (catnip oil), citronella oil, permethrin, neem oil, or bog myrtle extract. These active agents are effective insect repellants; and personal care formulations containing these are often effective as insect repellants.

In some embodiments, the personal care formulation comprises from 0 or 0.001 to 15 wt. % water, specifically, 0 or 0.01 to 12 wt. % water, 0.1 to 10 wt. % water, 0.5 to 8 wt. % water, or 1 to 5 wt. % water, each based on the total weight of the formulation. In some embodiments, the personal care formulation is essentially anhydrous, containing no more than 3 wt. % water, no more than 2 wt. % water, more specifically no more than 1 wt. % water. In essentially anhydrous personal care formulations, the amount of water can be 0%, as low as 0.001%, or 0.01%, or 0.1 wt. %, each based on the total weight of the personal care formulation.

In another aspect, for use in a waxy formulation, e.g., a lipstick, lip gloss, lip balm formulation, or a cuticle cream that contains a wax, an emollient, and 1,4-pentanediol and ketal alcohol (1) is provided. In embodiments of particular interest, the lipstick, lip gloss, lip balm, or cuticle cream formulation contains from 0.1 to 10 wt. % water, specifically 0.5 to 5 wt. % water, each based on the total weight of the persona care formulation. These formulations are in stick or other solid form. The ketal alcohol (1) specifically is a partially or fully water-miscible ketal alcohol (1), as defined below, when the waxy formulation contains more than 0.1 wt. % water.

In another aspect, a formulated personal care formulation in the form of an emulsion is provided. The emulsion can have a continuous phase and a disperse phase, one of which is an aqueous phase, and the other of which is an oil phase. Alternatively, the emulsion can have at least two co-continuous phases, again wherein at least one of the co-continuous phase is an aqueous phase and at least one of the co-continuous phases is an oil phase. The oil phase contains at least one of (a) a paraffinic, naphthenic or aromatic mineral oil, (b) a nonionic organic compound having a melting temperature of less than 45° C., a molecular weight of at least 190 Daltons, an amido or ester group, an alkyl chain containing at least 8 carbon atoms, and a solubility in water of no greater than 1 part in 99 parts of water by weight; (c) a nonionic organosilicone compound having a melting temperature of less than 45° C. and a solubility in water of no greater than 1 part in 99 parts of water by weight; (d) a long chain alcohol; and (e) a wax. The emulsion further comprises 1,4-pentanediol and ketal alcohol (1). The 1,4-pentanediol and ketal alcohol (1) can be present in a continuous phase, a disperse phase, in both a continuous phase and a disperse phase, or at the interface between a continuous and a disperse phase.

Personal care formulations and products can take the physical form of solids (sticks, bars, powders, etc.), solutions (including solutions containing sufficient gallant or thickener to provide a gel-like consistency), ointments, dispersions (including pastes), or emulsions (including gels, liniments, lotions, creams, or the like). They can be sprayable, in particular the solutions, dispersions, and powders.

Many personal care formulations are combinations of two or more of formulation forms. For example, some personal care formulations contain an aqueous phase that contains a dissolved active agent, and further includes an oil phase which can be present, for example, to supply emollients and/or humectants, or to produce a specific formulation form (cream, lotion and the like). In such cases, it is possible to include two or more ketal alcohols within the formulation to perform different functions. Thus, for example, a fully-water-miscible ketal alcohol might be present in the aqueous phase to help dissolve the active agent, and a partially-or sparingly water-miscible ketal alcohol might be present within the oil phase to reduce its viscosity or compatibilize its components. Either of these ketal alcohols can also perform some emulsifying or compatibilizing function between the aqueous and oil phases.

In addition, a single 1,4-pentanediol or ketal alcohol (1) can perform multiple functions within a personal care formulation, such as dissolving an active agent into an aqueous or oil phase, compatibilizing or emulsifying an aqueous phase with an oil phase, etc.

The 1,4-pentanediol and ketal alcohol (1) can reside in an aqueous phase, in an alcoholic or alcohol-water phase, or in an oil phase of a personal care formulation, depending on the particular formulation and the particular ketal alcohol. In many cases, 1,4-pentanediol and an ketal alcohol (1) can become distributed between aqueous and oil phases of a personal care formulation, due to its solubility in both phases. In some cases, the 1,4-pentanediol and ketal alcohol (1) can reside at the boundary of aqueous and oil phases.

The amount of 1,4-pentanediol and ketal alcohol (1) present in a personal care formulation depends on the function of the 1,4-pentanediol and ketal alcohol (1), the other ingredients of the personal care formulation, the specific form of the personal care formulation, and like considerations. In general, the formulation comprises 0.001 to 90 wt. %, 0.01 to 80 wt. %, 0.1 to 70 wt. %, or 0.1 to 50 wt. % of the 1,4-pentanediol and/or ketal alcohol (1) based on the total weight of the formulation, although a more typical amount is from 0.5 to 25 wt. %, and in many cases from 1 to 10 wt. % the total formulation weight.

Anti-aging, anti-acne, skin whitening and sun protection formulations can contain 0.001 to 50 wt. % of the active agent, specifically from 0.01 to 40 wt. %, based on the total weight of the formulation. Anti-aging and anti-acne formulations can be formulated into aqueous and/or ethanolic solutions, or into lotions or creams. Sun protection formulations can take the form of clear, low viscosity liquids (as is typical for spray-on formulations, which are often ethanolic or ethanol-water based), or else are lotions or creams. Spray-on sun protection formulations can be aqueous and/or ethanolic solutions or dilute emulsions. Many of the anti-aging, anti-acne, skin whitening and sun protection active agents are soluble to the extent of at least 5 parts per 95 parts of the ketal alcohol (1) in the formulation. These include, for example, avobenzone, coenzyme Q10, hydroquinone, oxybenzone, and salicylic acid, all of which are soluble to the extent of at least 5 parts per 95 part of 1,4-pentanediol, ketal alcohol (1a), ketal alcohol (1b), or a combination thereof. In these cases, the presence of the 1,4-pentanediol and/or the ketal alcohol often allows the amount of ethanol to be reduced, and/or the amount of active agent to be increased at a constant ethanol content, leading to a formulation which is less drying to the skin. In some cases, the 1,4-pentanediol and ketal alcohol can be used to replace a heavy-feeling material that solubilizes the active.

An anti-aging, anti-acne, skin whitening, or sun protection formulation can contain additional UV absorbing agents, notably inorganic compounds such as titanium dioxide or zinc oxide. These materials are solid particles that typically are dispersed into a lotion or cream formulation.

Sun protection formulations such as sunscreens often contain a mixture of organic UV absorbing agents, often in order to broaden the range of wavelengths of UV light that are absorbed. Such mixture of organic UV agents can include two or more of avobenzone, octylmethoxyl cinnamate, oxybenzone, and ethylhexyl salicylate. These may, in the aggregate, constitute from 0.1 to 50% of the weight of the sunscreen formulation, and more specifically constitute from 2 to 25 wt. % thereof.

A tanning formulation can contain 1 to 25 wt. %, for example 2 to 10 wt. %, of one or more tanning agents as described before. Tanning formulations often are formulated into a lotion or a cream. Spray-on tanning formulations can be aqueous and/or ethanolic solutions.

A tanning formulation can contain organic UV active agents, as described before, as well as inorganic UV active agents such as titanium dioxide or zinc oxide. As is the case with sunscreen formulations, organic UV active agents can constitute from 0.1 to 50 wt. %, specifically 0.1 to 30 wt. % of the weight of a tanning formulation, and more specifically from 2 to 25 wt. % thereof. A mixture of organic UV additives can be present, including a mixture of two or more of avobenzone, octylmethoxyl cinnamate, oxybenzone, and ethylhexyl salicylate.

Anti-dandruff formulations can contain from 0.1 to 25 wt. %, specifically from 0.5 to 10 wt. % of one or more of an anti-fungal agent as described before. The formulation form can be an aqueous solution, aqueous gel, or dilute emulsion containing mostly aqueous phase. An anti-dandruff formulation can contain one or more surfactants, particularly one or more anionic surfactants. Sulfosuccinate, lauryl sulfate, and laureth sulfate surfactants and the various fatty acid betaines, or fatty acid amide propyl betaines are preferred types, although others, particularly other anionic surfactants, can be used. Surfactants can constitute from 0.1 to 10 wt. % an anti-dandruff formulation. The surfactants can function as cleaning agents and/or emulsifiers in the formulation. An anti-dandruff agent can contain hair conditioners and other materials as well.

Anti-alopecia formulations can contain 0.1 to 25 wt. %, for example 1 to 10 wt. % of one or more of anti-alopecia agents. Formulations of these types typically are formulated into low to medium viscosity fluids, which can contain a propellant and be sprayable, which can be clear solutions in the case of anti-alopecia formulations or opaque emulsions in the case of anti-dandruff formulations. These formulations can contain propylene glycol, ethanol, and/or water as a cosolvent mixture, although an advantage of this invention is that levels of propylene glycol and/or ethanol can in some cases be reduced due to the presence of the 1,4-pentanediol and/or the ketal alcohol (1).

Chemical treatment formulations for hair include hair straighteners, relaxers, and/permanent wave formulations can contain one or more materials which straighten hair, possibly by breaking sulfur-sulfur bonds in keratin or some other component of hair; among these are the depilatory agents described before. They can constitute up to 10 wt. % of a chemical treatment active agent for hair. Chemical treatment formulations for hair can take the form of low viscosity fluids, lotions, creams, or gels.

A hair styling formulation can contain one or more hair fixatives, which hold the hair into a re-styled position. Some of these fixatives can also function as thickeners in a hair straightening and styling formulation. The hair fixative can be 0.25 to 25 wt. %, for example 0.5 to 15 wt. % of the formulation. The hair styling formulation can take the form of an aqueous and/or ethanolic solution, a gel, or a lotion.

Anti-perspirant formulations contain one or more anti-perspirant agents such as described before. Anti-perspirant formulations can take the form of a gel, a viscous liquid (for roll-on applications), or a stick.

A stick or roll-on anti-perspirant can contain some water, which can constitute from 2 to 60% of the weight of the formulation, and at least 5%, up to 30 wt. % the anti-perspirant agent.

A topical medicinal formulation can contain one or more medicinal agents such as an amphetamine, antihistamine, methylphenidate, oxymetazoline, tetrahydrolzoline hydrochloride, psilocybin, clotrimazole, tea tree oil, piroctone olamine, chlorhexidine, octenidine, triclosan, sodium 3,5-dibromo-4-hydroxybenzenesulfonate (Dibromol), quaternary ammonium salts such as benzalkonium chloride, cetyl trimethylammonium bromide, cetylpyridinium chloride, and benzethonium chloride, and the like. These formulations can be formulated into low viscosity fluids (which can be sprayable), gels, lotions, creams, liniments, or ointments. Low viscosity fluid formulations can be aqueous and/or ethanolic; lotions and creams can be emulsions containing an aqueous continuous phase and a dispersed or co-continuous phase that contains an emollient.

Hair dye formulations can include hair dyes such as those described above. Hair bleaching formulations can contain a peroxy-type bleaching agent such as hydrogen peroxide in an effective amount, for example 0.1 to 5 wt. % of the total weight of the formulation in the case of dyes; and 1 to 20 wt. % in the case of bleaches. A bleaching formulation can in addition contain an inorganic oxidant such as a persulfate salt, in an amount of 0.1 to 5 wt. % of the formulation. Hair dye and bleaching formulations can take the form of low viscosity fluids, lotions, creams, or gels. They can also be prepared in a water-dilutable concentrate form. A hair dye or bleaching formulation can contain one or more surfactants which can function to stabilize the emulsion, or as a detergent.

Depilatory formulations can contain one or more depilatory agents such as those described before, for example in an amount of 1 to 20 wt. %, based on the weight of the formulation. Depilatory formulations can be in the form of lotions, creams, or gels.

In another aspect, a waxy solid formulation that contains a wax, an emollient, and 1,4-pentanediol and/or an ketal alcohol is provided. The waxy solid formulation can contain from 0.5 to 20 wt. %, 15 wt. %, 10 wt. %, 8 wt. %, 5 wt. %, 4 wt. %, or 3 wt. % water. These formulations can be provided in stick or other solid form. They can contain at least 20 wt. % of an oil such as castor oil, a wax (as defined below) and at least 0.5 wt. % 1,4-pentanediol and/or a ketal alcohol (1). The 1,4-pentanediol and ketal alcohol (1) can be present in an amount up to 25 wt. %, 20 wt. %, 15 wt. %, or 10 wt. % the formulation. The ketal alcohol can be a partially or fully water-miscible ketal alcohol, as defined below, when the waxy solid formulation contains more than 0.5 wt. % water. Such formulations include lip formulations such as a lipstick, lip gloss, or lip balm; cuticle creams; and the like.

Many waxy formulations, including lip care formulations include a mixture of one or more waxes with one or more oils and, in the case of lipsticks, one or more pigments. Lipsticks and lip balm formulations, as well as cuticle creams, tend to be malleable solids at 25° C., whereas lip glosses tend to be viscous liquids or pastes. These formulations are normally characterized as being anhydrous, i.e., containing up to 3 wt. % water. A lip care formulation can contain, for example, from 1 to 30 wt. % of a wax; from 30-95 wt. % of one or more other hydrophobic materials, of which castor oil is typically an important component; and from 1 to 30 wt. % of one or more pigments. In some embodiments, the lipstick or lip balm formulation contains a ketal alcohol that is partially or fully miscible with water. In these embodiments, the presence of the ketal alcohol allows for some amount of water to be incorporated into the formulations, while retaining other needed properties such as the necessary rheological characteristics (including, in the case of lipsticks in particular, the ability to retain its stick form) and formulation stability. From 0.5 to 10 wt. % or more, for example 0.5 to 5 wt. % water can be incorporated into a lipstick, lip gloss, or lip balm in this manner. The amount of the water-miscible ketal alcohol(s) can constitute from 1 to 25 wt. % of a waxy formulation such as a lipstick, lip gloss, or lip balm formulation or cuticle cream. In some embodiments, the ketal alcohol is present in a part per part by weight water, if water is present.

Similarly, the presence of a partially or fully water-miscible ketal alcohol can permit water to be incorporated into other normally anhydrous personal care formulations to the extent of up to 10% or more by weight, without significant change in formulation form or function.

In addition to the foregoing active agent-containing personal care formulations, a significant number of personal care formulations do not contain any of the foregoing active agents, but nonetheless exist in the form of emulsions. The emulsions can be water-in-oil types, oil-in-water types, or types containing co-continuous aqueous and oil phases. These formulations typically take the form of low viscosity fluids (in which the disperse phase, which is typically an oil phase, constitutes a small proportion, typically 35% or less or 10% or less by weight of the formulation), lotions, or creams. These formulations include, for example, hair conditioners, after-shave lotions, various body cleansers, various hand and skin lotions and creams and the like, which do not contain specific active agents as described above. Emulsion formulations of these types typically contain from 0.1 to 50 wt. % 1,4-pentanediol, ketal alcohol (1), or a combination thereof.

Additional ingredients that can be included in the personal care formulations of this disclosure include paraffinic, naphthenic, or aromatic mineral oil; a nonionic organic compound having a melting temperature of less than 45° C., a molecular weight of at least 190 Daltons, an amido or ester group, and an alkyl chain containing at least 8 carbon atoms, and a solubility in water of no greater than 1 part in 99 parts of water; a nonionic organosilicone compound having a melting temperature of less than 45° C., and a solubility in water of no greater than 1 part in 99 parts of water; a long chain alcohol (eight or more carbon atoms), a wax, or a combination comprising at least one of the foregoing. Additional ingredients can also include emollients such as vegetable oils and animal fats and derivatives thereof; nonionic organosilicone compounds such as dimethicone and cyclopentasiloxane; cosolvents as described herein above; natural, synthetic, or modified organic polymers; surfactants as described herein above; natural or synthetic fragrances; botanical extracts; natural or synthetic dyes; pigments or pearlizers; pH adjusters/buffers and chelating agents; inorganic particulates; non-hydrocarbon propellants; preservatives, and a combination comprising at least one of the foregoing.

Formulations containing 1,4-pentanediol and/or a ketal alcohol (1), especially a sparingly water-soluble ketal alcohol, have been found to be excellent cosmetic (make-up) removers, particularly if the formulation contains at least 5 wt. % and more specifically at least 8 wt. % the ketal alcohol. The ketal alcohol can constitute up to 75 wt. %, up to 60 wt. % or up to 50 wt. % of the weight of a cosmetic remover formulation. A cosmetic remover in can include, in addition to the ketal alcohol, water, an alcohol such as ethanol, isopropanol or 1,2- or 1,3-propane diol; one or more of components above. Such a cosmetic remover can even be free of surfactants, or contain low (less than 2 wt. %) concentrations of surfactants.

The 1,4-pentanediol and ketal alcohols are also efficient solvents for polymers that are generally present in nail polishes, such as nitrocellulose, cellulose acetate propionate, cellulose acetate butyrate, styrene/acrylates copolymers, acrylates copolymers, polyethylene terephthalate and tosylamide/formaldehyde resins and thus find benefit as solvents in nail polish removers, nail strengthening formulations, and/or nail polishes.

The personal care formulations described herein satisfy certain continuing needs in the art for formulary ingredients. The 1,4-pentanediol and ketal alcohols (1) can be used in a wide range of formulation forms and in a wide variety of specialized applications. Although these various types of formulations differ enormously, as do the conditions under which they are used, the 1,4-pentanediol and ketal alcohols (1) can be used in the formulation of many of them, which greatly simplifies the formulation process.

In addition, formulating personal care formulations must often simultaneously address formulation needs that are often competing and sometimes even contradictory. For example, many personal care formulations contain an active agent that lends a particular functional attribute to the formulation. It can be desirable to increase the concentration of the active agent in a given formulation, or to produce a formulation that contains the active agent in a specific formulation form (such as a solution, dispersion, lotion, cream, stick, gel, or the like), but the formulator is limited by the solubility of the active agent in the other ingredients in the formulation. Approaches to address solubility include the use of various types of emulsifiers, oils, cosolvents, and the like, but it is often the case that other requirements, such as the specific formulation form, are incompatible with the presence of such materials in the amounts needed for efficacy. Use of 1,4-pentanediol and/or a ketal alcohols (1) allows an increased concentration of active agent in a wide variety of specific personal care formulation forms. The 1,4-pentanediol and ketal alcohols (1) are further compatible with many other ingredients of personal care formulations.

In other cases, the presence or absence of a specific ingredient that can be an aid to solubility is important. For example it can be desirable to reduce or eliminate volatile organic compounds ("VOCs") from a personal care formulation, in favor of an aqueous-based formulation. Some ingredients, such as ethanol, can dry the skin and in some cases are to be avoided for that reason, or for other reasons, such as VOC regulations in some jurisdictions. Conversely, there are other cases in which ethanol and/or another relatively volatile material is desired, so the formulation dries rapidly when it is applied, for example. In some embodiments, use of the 1,4-pentanediol and ketal alcohols (1) results in formulations that do not contain VOCs. In an embodiment, the formulations and products described herein can be low—VOC as defined below.

Use of the 1,4-pentanediol and/or ketal alcohols (1) in personal care formulations can enhance the compatibility amongst the various ingredients of the formulations. Many personal care formulations contain both hydrophilic and hydrophobic components. These ingredients tend not to mix into each other. In order to create a formulation that does not rapidly separate into oil-rich and water-rich layers, emulsifiers, cosolvents, or thickeners can be included so that it becomes kinematically stable. These emulsifiers, cosolvents, and thickeners often play little role in the function or performance of the formulation (i.e., are not active agents), although they can affect the spreading characteristics and feel on the skin. They mainly are present to permit the various functional ingredients to coexist in a stable formulation form or to provide a desired feel or consistency to the formulation. The inclusion of certain compatibilizing ingredients (such as volatile or drying organic solvents, for example), as described above, can more specifically be omitted from some formulations. The need to include such compatibilizers can increase formulation complexity. Formulations that require compatibilization can be very sensitive to small formulational changes. Small changes to a formulation often destabilize it, requiring a new balance of ingredients.

The 1,4-pentanediol and ketal alcohols (1) can perform the function of emulsifiers, oils, cosolvents, compatibilizers, and like materials. In a further advantage, the 1,4-pentanediol and ketal alcohols (1) enhance the spreading of the formulation, and/or do not feel greasy or heavy. Use of the 1,4-pentanediol and ketal alcohols (1) can provide simplified formulations for personal care formulations that still have the needed formulation attributes and functions. In other cases, use of the 1,4-pentanediol and ketal alcohols (1) can reduce the quantities of the various formulary components, and thus can reduce costs and simplify formulating. This can allow a formulator to maintain a simplified raw material inventory and thus reduce associated costs. Use of the 1,4-pentanediol and ketal alcohols (1) can also result in personal care formulations that are more robust to formulation changes.

Fragrance Compositions

The 1,4-pentanediol and the ketal alcohols (1) are also useful in perfume and flavorant formulations (hereinafter jointly referred to as fragrant formulations). Fragrant compositions are used interchangeably with frangrant formulations.

The fragrant composition comprises at least one fragrant compound (also referred to herein as a fragrant molecule). The fragrant molecule is also referred to as an aroma compound. The fragrant molecule can be a naturally occurring molecule or a synthetic molecule (e.g., a molecule that is synthesized in a laboratory from ingredients that are not naturally occurring). Naturally occurring molecules are those that are derived directly or indirectly from living beings (e.g., animals, plants, fruit, flowers, and the like). Naturally occurring molecules include products of naturally occurring molecules and synthetic molecules. Fragrant molecules can be found in food, wine, spices, perfumes, fragrance oils, and essential oils. For example, many form biochemically during ripening of fruits and other crops. In wines, most form as byproducts of fermentation.

Naturally occurring fragrant molecules include "essential" oils derived from plants. Essential oils are concentrated, hydrophobic liquids containing volatile fragrant molecules from plants. Essential oils are also known as volatile, ethereal oils or aetherolea, or simply as the "oil of" the plant from which they were extracted, such as, for example, oil of clove. An oil is "essential" in the sense that it carries a distinctive scent, or essence, of the plant. Essential oils do not have any specific chemical properties in common, beyond conveying characteristic fragrances. Some essential oils such as lavender, peppermint, and eucalyptus, are steam distilled. Raw plant material, comprising flowers, leaves, wood, bark, roots, seeds, or peel, are put into a distillation apparatus over water. As the water is heated the steam passes through the plant material, vaporizing the volatile compounds. The vapors flow through a coil where they condense back to liquid, which is then collected in the receiving vessel.

Essential oils are derived from berries, allspice, juniper, seeds, almond, anise, celery, cumin, nutmeg oil, bark, cassia, cinnamon, sassafras, wood, camphor, cedar, rosewood, sandalwood, agarwood, rhizome, galangal, ginger, leaves, basil, bay leaf, cinnamon, common sage, eucalyptus, lemon grass, melaleuca, oregano, patchouli, peppermint, pine, rosemary, spearmint, tea tree, thyme, wintergreen, resin, frankincense, myrrh, flowers, cannabis, chamomile, clary sage, clove, scented geranium, hops, hyssop, jasmine, lavender, manuka, marjoram, rose, rosemary, basil, lemon grass, ylang-ylang, peel, bergamot, grapefruit, lemon, lime, orange, tangerine, root, valerian, mango, or the like, or a combination comprising at least one of the foregoing.

Examples of fragrant molecules are alcohols (e.g., furaneol (strawberry), 1-hexanol (herbaceous, woody), cis-3-hexen-1-ol (fresh cut grass), menthol (peppermint), or the like, or a combination comprising at least one of the foregoing alcohols); aldehydes (e.g., acetaldehyde (pungent), hexanal (green, grassy), cis-3-hexenal (green tomatoes), furfural (burnt oats), or the like, or a combination comprising at least one of the foregoing aldehydes); esters (e.g., fructone (fruity, apple-like), hexyl acetate (apple, floral, fruity), ethyl methylphenylglycidate (strawberry), methyl formate, methyl acetate, methyl butyrate, methyl butanoate, ethyl acetate, ethyl butyrate, ethyl butanoate, isoamyl acetate, pentyl butyrate, pentyl butanoate, pentyl pentanoate, benzoin (extracted from resin of styrax benzoin tree); black pepper (from the plant piper nigrum of the piperaceae family), cajuput oil (from melaleuca cajuputi), caraway, carrot seed, coriander, cypress, dill, fennel, helichyrsum, lavandin, lemon verena, bee balm (lemon balm essential oil extracted from melissa officinalis of the labiatae family), niaouli, palmarosa, petitgrain, tagetes, vetiver, or the like, or a combination comprising at least one of the foregoing esters); ketones (e.g., dihydrojasmone (fruity woody floral), oct-1-en-3-one (blood, metallic, mushroom-like), 2-acetyl-1-pyrroline (fresh bread, jasmine rice), 6-acetyl-2,3,4,5-tetrahydropyridine (fresh bread, tortillas, popcorn), or the like, or a combination comprising at least one of the foregoing ketones); lactones (γ-decalactone (intense peach flavor), γ-nonalactone (coconut odor, popular in suntan lotions), δ-octalactone (creamy note, jasmine lactone powerful fatty fruity peach and apricot) massoia lactone (powerful creamy coconut, wine lactone sweet coconut odor) sotolon (maple syrup, curry, fenugreek), or the like, or a combination comprising at least one of the foregoing lactones); thiols (ethanethiol (commonly called ethyl mercaptan), grapefruit mercaptan (grapefruit), methanethiol (commonly called methyl mercaptan), 2-methyl-2-propanethiol (commonly called tertiary-butyl mercaptan)); linear terpenes (e.g., myrcene (woody, complex), geraniol (rose, flowery) nerol (sweet rose, flowery), citral, lemonal, geranial, neral (lemon, lemon myrtle, lemongrass), citronellal (lemon, lemongrass), citronellol (lemon, lemongrass, rose, pelargonium), linalool (floral, sweet, woody, lavender), nerolidol (woody, fresh bark), or the like, or a combination comprising at least one of the foregoing linear terpenes; cyclic terpenes (e.g., limonene, camphor, terpincol, ionone, thujuon, or the like, or a combination comprising at least one of the foregoing cyclic terpenes); aromatic species (e.g., benzaldehyde, eugenol, cinnamaldehyde, ethyl maltol, vanillin, anisole, anethole, estragole, thymol, or the like or a combination comprising at least one of the foregoing aromatic species); amines (e.g., thiethylamine, trimethylamine, cadaverine, pyridine, indole, skatole, or the like, or a combination comprising at least one of the foregoing amines) or the like, or a combination comprising at least one of the foregoing fragrant molecules.

Additional examples of fragrant molecules are geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzyl carbinol, trichloromethylphenylcarbinyl acetate, p-tert-butyl-cyclohexyl acetate, isononyl acetate, vetiveryl acetate, vetiverol, alpha-n-amylcinammic aldehyde, alpha-hexylcinammic aldehyde, 2-methyl-3-(p-tert-butylphenyl)-propanol, 2-methyl-3-(p-isopropylphenyl)-propanal, 3-(p-tert-butylphenyl)-propanal, tricyclodecenyl acetate, tricyclodecenyl propionate, 4-(4-hydroxy-4-methyl-pentyl)-3-cyclohexene carbaldehyde, 4-(4-methyl-3-pentenyl)-3-cyclohexene carbaldehyde, 4-acetoxy-3-pentyletetrahydropyran, methyl-dihydrojasmonate, 2-n-heptylcyclopentanone, 3-methyl-2-pentylcyclopentanone, n-decanal, 9-decenol-1, phenoxyethyl isobutyrate, phenylacetaldehyde dimethyl acetal, phenylacetaldehyde diethyl acetal, geranonitrile, citronellonitrile, cedryl acetate, 3-isocamphycyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethylioniones, irones, cis-3-hexenol and esters thereof, indane musk, tetralin musk, isochroman musk, macrocyclic ketones, macrolactone musk, ethylene brassylate, aromatic nitro-musk.

Exemplary fragrant molecules include bergamot oil, coriander oil, dimethyl heptanol, dimethyl benzyl carbinyl acetate, geranyl acetate, citronellyl acetate, rose synthetic, geranium bourbon, hedione, iso eugenol, methyl eugenol styrallyl acetate, stemone, rose oxide laevo, aldehyde C-11 undecyclic, derivatives of 2,6-dimethyl-2-alkoxy octan-7-ol, vertivert oil, vetiverol, vetiveryl, acetate, quaiac wood oil, esters ol-anthranilic acid, benzyl salicylate, benzyl benzoate, oak moss, eugenol, p-tert-butyl cyclohexyl acetate and coumarin.

In one embodiment, an additional solvent may be used in the fragrant formulation in addition to the 1,4-pentanediol or the ketal alcohols (1). Polar solvents such as water, propylene carbonate, ethylene carbonate, butyrolactone, acetonitrile, benzonitrile, nitromethane, nitrobenzene, sulfolane, dimethylformamide, N-methylpyrrolidone, glycol ethers, methyl acetate, ethyl acetate, methanol, acetonitrile, nitromethane, ethanol, propanol, isopropanol, butanol, benzyl alcohol, butoxydiglycol, 1,2-propane diol (propylene glycol), 1,3-propane diol, ethoxydiglycol, hexylene glycol, and dipropylene glycol, triethylene glycol, hexylene glycol, diethylene glycol, ethylene glycol, propylene glycol, 1,2-butylene glycol or the like, or combinations comprising at least one of the foregoing solvents are generally desirable. Non-polar solvents such a benzene, toluene, methylene chloride, carbon tetrachloride, hexane, diethyl ether, hexane, tetrahydrofuran, or the like, or combinations comprising at least one of the foregoing non-polar solvents may also be used. Co-solvents comprising at least one polar solvent and at least one non-polar solvent may also be utilized to modify the compatibilizing capabilities of the solvent and thereby adjust the clarity and haze characteristics of the fragrant formulation. Exemplary solvents are methyl acetate, ethyl acetate, glycol ethers and water. Glycol ethers and alcohols can be used to compatibilize 1,4-pentanediol or the ketal alcohols (1) with water if desired. Exemplary solvents are water and ethyl alcohol.

In one embodiment, the fragrant formulation can optionally comprise a radical scavenger or a source of a radical scavenger. As used herein the term radical scavenger refers to a species that can react with a carbonate radical to convert the carbonate radical by a series of fast reactions to a less reactive species, i.e. a carbonate radical scavenger.

Radical scavengers can be selected from the classes of alkanolamines, amino sugars, amino acids, esters of amino acids and mixtures thereof. For example, the following compounds can be employed as radical scavengers: ethylamine, monoethanolamine, 2-methoxyethylamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, morpholine, piperidine, or the like, or a combination comprising at least one of the foregoing radical scavengers.

The fragrant formulation can optionally comprise a polymer. It is generally desirable for the polymer to be soluble in the 1,4-pentanediol or the ketal alcohols (1) and/or in the cosolvent used with the 1,4-pentanediol or the ketal alcohol (1). In one embodiment, the polymer is water-soluble. In another embodiment, the polymer is not water-soluble and exists as a dispersion in the fragrant formulation.

It is desirable for the polymer to be an organic polymer. The polymer may be a thermoplastic, a thermosetting polymer, or a combination of a thermosetting polymer with a thermoplastic polymer. In one embodiment, the polymer may be an oligomer, a homopolymer or a copolymer. The copolymer can be a block copolymer, a star block copolymer, a random copolymer, an alternating block copolymer, a dendrimer, an ionic block copolymer, a polyelectrolyte, or the like, or a combination comprising at least one of the foregoing polymer.

Examples of polymers that are water-soluble are polyvinyl alcohol, polyacrylamides, polyvinylpyrollidones, polyamides, hydroxyalkyl celluloses such as hydroxyethylcellulose and hydroxypropylcellulose, polyacrylic acid, or the like, or a combination comprising at least one of the foregoing water-soluble polymers.

Examples of polymers that are not water-soluble are polymethylmethacrylates, polyacrylates, polyesters, polyimides, polyethers, polyolefins, polyetherketones, polyether ether ketones, polyether ketone ketones, polycarbonates, polyarylene ethers, epoxies, polysulfones, polyethersulfones, polyetherimides, polynorbornylene, polysiloxanes, polyvinylchlorides, fluoropolymers, liquid crystalline polymers, ionomers, or the like, or combinations comprising at least one of the foregoing non-water-soluble polymers.

The polymers can be used as rheology modifiers, dispersants, stabilizers, promoters, or antimicrobials, and the like; in industrial product applications, such as, textiles (processing, finishing, printing, and dyeing aids, protective washable surface coatings, manufacture of synthetic leather by saturation of non-woven fabrics, and the like; manufacturing of woven fabrics, non-woven fabrics, natural and synthetic fibers and the like); water treatments (waste water, cooling water, potable water purification, and the like); chemical spill containments (acid-spill absorbent, and the like); leather and hide processing (processing aids, finishing, coating, embossing, and the like); paper and papermaking (surface coatings, such as pigmented coatings, antistatic coatings, and the like, pulp binders, surface sizings, dry and wet strength enhancers, manufacture of wet-laid felts, and the like); printing (inks, antiwicking ink-jet printer inks, thickeners for ink formulations containing cationic dyes for printing acrylic fabrics, and the like); paints (pigment and grinding additive, crosslinking agent for epoxy latex emulsions, particulate-suspending aid for clays, pigments, and the like); industrial plant effluent treatment (flocculants for phenolics in paper mill effluent, and the like); metal working (acid etch cleaners, low pH metal coatings, pickling agents in cold rolled steel processing, and the like); adhesives (clear adhesives, adhesion promoters for metal, plastic, wood, and the like, non-woven floc adhesive tie coatings, bonding, and the like); wood preservation; and industrial construction products for buildings and roads (cement plasticizers, asphalt emulsion stabilizers at low pH, acid etch for cement, consistency modifiers of concrete, mortar, putty, and the like).

The polymer has a number average molecular weight of less than or equal to about 1,000,000 grams per mole, specifically less than or equal to about 500,000 grams per mole, specifically less than or equal to about 50,000 grams per mole, and more specifically less than or equal to about 5,000 grams per mole.

Other additives may also be added to the fragrant composition to form a fragrant formulation. These additives are optional. Suitable additives are antioxidants, antiozonants, antibacterial agents, humectants, colorants, dyes, pigments, food additives, pheromones, musks, a carbonate ion source, an alkalizing agent, a pH buffer, a conditioning agent, a chelant, an auxiliary agent, solvents (e.g., a cosolvent), surfactants (as cleansing agents, emulsifying agents, foam boosters, hydrotropes, solubilizing agents, and suspending agents), nonsurfactant suspending agents, emulsifiers, skin conditioning agents (emollients, humectants, moisturizers, and the like), hair conditioning agents, hair fixatives, film-formers, skin protectants, binders, chelating agents, antimicrobial agents, antifungal agents, antidandruff agents, abrasives, adhesives, absorbents, dyes, deodorant agents, antiperspirant agents, opacifying and pearlescing agents, preservatives, propellants, spreading aids, sunscreen agents, sunless skin tanning accelerators, ultraviolet light absorbers, pH adjusting agents, botanicals, hair colorants, oxidizing agents, reducing agents, skin bleaching agents, pigments, physiologically active agents, anti-inflammatory agents, topical anesthetics, fragrance and fragrance solubilizers, a polymer, and the like, in addition to ingredients previously discussed that may not appear herein. Oral care products, for example, can contain anticaries, antitartar and/or antiplaque agents in addition to surfactants, abrasives, humectants, flavorants, or the like, or a combination comprising at least one of the foregoing additives.

In one embodiment, in one method of manufacturing the fragrant formulation, a fragrant composition, 1,4-pentanediol or the ketal alcohol (1) as described above, an optional solvent, an optional active agent, an optional surfactant, an optional thickening agent, an optional compatibilizer and desired additives are blended together in the desired quantities in a reactor. The reactor may be a batch or continuous reactor. It is desirable for the reactor to be fitted with a mechanism for agitating the fragrant formulation. The fragrant formulation may be heated if desired to evaporate some solvent or to further drive compatibilization between the fragrant composition, the 1,4-pentanediol or the ketal alcohol (1) and the optional solvent.

In another embodiment, in another method of manufacturing the fragrant formulation, the 1,4-pentanediol or the ketal alcohol (1) may be used as an extraction solvent to extract a fragrant composition such as essential oils from naturally occurring substances. The 1,4-pentanediol or the ketal alcohol (1) may be retained with the essential oil and further processed to form a desired fragrant formulation. The essential oils can be extracted via steam extraction, supercritical extraction or solvent extraction. 1,4-pentanediol or the ketal alcohol (1) can be used in conjunction with steam, supercritical solvents or normal solvents (solvents that are not in a supercritical state) to effect extraction of essential oils. 1,4-pentanediol or the ketal alcohol (1) can also be used by itself to extract essential oils.

Steam extraction is normally environmentally friendly and uses only water to effect the extraction. Water is not however, a good solvent for all essential oils. 1,4-pentanediol or the ketal alcohol (1) can be used in conjunction with water to extract additional essential oil from a naturally occurring substance than that which would be extracted by using only steam for the extraction. The use of 1,4-pentanediol or the ketal alcohol (1) in steam extraction would continue to render the process environmentally friendly, while at the same time being effective to extract additional oil from the naturally occurring substance.

Supercritical extraction is generally conducted with carbon dioxide, but can also be effected with other solvents. A blend of supercritical carbon dioxide and 1,4-pentanediol or the ketal alcohol (1) can be used to extract essential oils for the fragrant formulation. Liquid carbon dioxide (that is not in a supercritical state) blended with 1,4-pentanediol or the ketal alcohols (1) can also be used for extraction. Other supercritical fluids can also be blended with 1,4-pentanediol or the ketal alcohols (1) to extract essential oils.

Hexane extraction is generally used to extract a variety of essential oils. 1,4-pentanediol or the ketal alcohol (1) can be blended with the hexane (or other solvents) to facilitate improved extraction. Ethanol is often used to target the segregation of a target molecule from hexane after extraction. In one embodiment, while the 1,4-pentanediol or the ketal alcohol (1) is used to facilitate the extraction of an essential oil in conjunction with hexane, it can also be used to facilitate a segregation of a target molecule from the hexane. By changing the ratio of the amount of the 1,4-pentanediol or the ketal alcohol (1) in the mixture of the target molecule and hexane and/or temperature, the target molecule can be segregated after the extraction. Other solvents can be used in conjunction with the 1,4-pentanediol or the ketal alcohol (1) to facilitate segregation of the target molecule.

In yet another embodiment, the 1,4-pentanediol or the ketal alcohol (1) by itself can be used to facilitate an extraction of various essential oils from naturally occurring substances. 1,4-pentanediol or the ketal alcohol (1) ester can be blended with the naturally occurring substance and under suitable combinations of temperature and pressure can facilitate the extraction of an essential oil from the naturally occurring substance. The resulting product can then be subjected to purification processes such as filtration, decantation, distillation, and the like to obtain a purified mixture of the essential oil and the 1,4-pentanediol or the ketal alcohol (1). The mixture of the essential oil and the 1,4-pentanediol or the ketal alcohol (1) can then be blended with other suitable ingredients to produce the desired fragrant formulation. Thus the 1,4-pentanediol or the ketal alcohol (1) may be used not only to extract the essential oil but can serve as a solubilizing solvent and/or a fixative in the fragrant formulation.

The blending to form the fragrant composition or the fragrant formulation may be conducted via dry blending, melt blending, solution blending or a combination comprising at least one of the foregoing forms of blending. Dry blending encompasses blending without the use of solvents and is generally conducted to blend two or more fragrant compositions. Melt blending occurs when the temperature of blending is conducted above the melting point of some of the ingredients and wet blending is generally conducted in the presence of solvents.

The blending of the formulation involves the use of shear force, extensional force, compressive force, ultrasonic energy, electromagnetic energy, thermal energy or combinations comprising at least one of the foregoing forces or forms of energy and is conducted in processing equipment wherein the aforementioned forces are exerted by a single screw, multiple screws, intermeshing co-rotating or counter rotating screws, non-intermeshing co-rotating or counter rotating screws, reciprocating screws, screws with pins, barrels with pins, rolls, rams, helical rotors, or combinations comprising at least one of the foregoing.

Blending involving the aforementioned forces may be conducted in machines such as single or multiple screw extruders, Buss kneader, Henschel, helicones, Ross mixer, Banbury, roll mills, molding machines such as injection molding machines, vacuum forming machines, blow molding machine, kettles, kettles with distillation and/or condensation columns, or then like, or combinations comprising at least one of the foregoing machines.

The fragrant formulation may be used in a variety of articles and applications. It may be used in body lotions, shampoos, massage oils, as a chemical identifier (e.g., in non-smelling chemicals or in toxic or hazardous chemicals), to mask odor, in perfume sticks and lanterns, air fresheners, candles, paints, varnishes, furniture, insect repellents, in polymers, cleaners, detergents, cosmetics, toiletries, cosmeceuticals and beauty aids, personal hygiene and cleansing products applied to the skin, hair, scalp, and nails of humans and animals. The fragrant formulations are used in a variety of air fresheners such as for example, spray, gel (e.g., an electric air freshener or beads), a paper substrate (e.g., car air fresheners hanging from rearview mirrors) or liquid (e.g., reed diffusers or with electric air fresheners).

The term "health care products" as used herein includes pharmaceuticals, pharmacosmetics, oral care products (mouth, teeth), eye care products, ear care products and over-the-counter products and appliances, such as patches, plasters, dressings and the like, and medical devices externally applied to or into the body of humans and animals for ameliorating a health-related or medical condition, for generally maintaining hygiene or well-being, and the like. The term "body" includes the keratinous (hair, nails) and non-keratinous skin areas of the entire body (face, trunk, limbs, hands and feet), the tissues of body openings and eyes, and the term "skin" includes the scalp and mucous membranes. The term "household care products" as used herein includes products employed in a domestic household for surface cleaning, odor control or masking, or biocidal cleaning products for maintaining sanitary conditions, such as in the kitchen and bathroom, laundry products for fabric care and cleaning, air fresheners, air sanitizers, air deodorizers/odor removers, candles, and the like. These products can be used in the home, in the workplace, or in institutional settings.

The fragrant composition or fragrant formulation is generally added as a concentrate to an article to produce a desired sensory effect in the article. The ratio of the fragrant composition to the 1,4-pentanediol or the ketal alcohol (1) used in the fragrant formulation may vary from article to article depending upon the composition of the article. In addition, the amount of the fragrant composition may also vary from article to article depending upon the utility of the article.

In one embodiment, the fragrant formulation may be added to organic polymer formulations to impart to the organic polymer a particular odor or in order to mask an undesirable odor. Examples of polymers to which the fragrant formulation can be added are polyolefins, polyvinyl acetates, polystyrenes cellulose acetates, acrylonitrile butadiene styrene, polyacrylics, polycarbonates, polyamides, polyurethanes, epoxies, and polyesters.

Dispersants and Slip Agents for Particulate Solids

In another embodiment, the 1,4-pentanediol and the ketal alcohols (1) are useful in dispersions of solid particles in a continuous phase, methods of their manufacture, and their uses.

The term "miscible" and its variations ("miscibility", "compatibility", and the like) are used herein as a synonym for "soluble", i.e., a mixture of the materials by themselves form a "true" solution, in which one material is molecularly dispersed in the other, or in which one material is dispersed as droplets which have a longest dimension of less than 200 nm, such that the mixture is optically clear. In an exemplary embodiment, the longest dimension is a "radius of gyration." As used herein, a material that is "miscible" or "fully miscible" in another, without further qualification, is miscible with that other material in all proportions, i.e., in mixtures that contain the two components by themselves in all weight ratios from 99:1 to 1:99. A fully miscible ketal alcohol is soluble in another material, such as water, at all proportions from 99:1 to 1:99. A partially miscible ketal alcohol is immiscible in another material in proportions from greater than 30 parts of the ketal alcohol in 70 parts or less of the other material and miscible in other combinations. A sparingly miscible ketal alcohol is immiscible in another material or miscible in another material to the extent of less than 10 parts in 90 parts of the other material. A material is "immiscible" in another if it is not soluble by itself in that material to the extent of at least 1 part per 99 parts of the other. Unless stated otherwise, miscibility is assessed at 25° C. The foregoing ketal alcohols can be classified as fully water-miscible, partially water-miscible, or sparingly water-miscible. By "macroscopically uniform," it is meant that the formulation is uniform when viewed at a length scale of at least 10 micrometers.

The selection of 1,4-pentanediol or the ketal alcohols (1), such as (1a), (1b), or a combination comprising at least one of the foregoing for a particular formulation will depend at least in part upon the function or functions that the 1,4-pentanediol or ketal alcohol (1) is expected to perform in the formulation, as well as the other ingredients of the formulation. For example, when the ketal alcohol (1) is present to disperse hydrophobic particles into an aqueous continuous phase, a partially- or fully-water miscible ketal alcohol (1) is selected. If the particles are highly hydrophobic, a mixture of a partially- or fully-water miscible ketal alcohol (1) with a sparingly water-miscible ketal alcohol (1) can be used. In a coating formulation, the specific ketal alcohol (1) may be chosen to have a particular volatility profile so that the coating dries at a desired rate, or because of its ability to carry out additional functions (e.g., coalesced latex particles). Similarly, in cosmetic formulations, the specific ketal alcohol (1) such as (1a), (1b), or a combination comprising at least one of the foregoing may be chosen for its feel on the skin (i.e., emolliency)

When the 1,4-pentanediol or the ketal alcohols (1), such as (1a), (1b), or a combination comprising at least one of the foregoing is present to disperse particles into an alcoholic phase or an alcohol/water mixture, the 1,4-pentanediol or the ketal alcohols (1), such as (1a), (1b), or a combination comprising at least one of the foregoing is preferably miscible in the alcohol, for example to the extent of 10 parts in 90 parts of the alcohol, and can be fully miscible in the alcohol. Ketal alcohols that are fully or partially miscible in the alcohol can be present in a mixture with one or more ketal alcohols that are only sparingly soluble in the alcohol. This can allow, for example, the alcohol/miscible ketal alcohol (1) mixture to function as a cosolvent mixture in which the sparingly soluble ketal alcohol (1) is dissolved. The sparingly soluble ketal alcohol (1) can in turn compatibilize another material into the formulation. In some alcoholic systems and alcohol/water systems, the ketal alcohol (1) performs a compatibilization and/or emulsification function, such as to compatibilize or emulsify aqueous and oil phases in an emulsion. The alcohol in such an alcoholic phase or alcohol/water mixture is a lower alcohol, including C1-7 alkanols such as ethanol, 1-propanol, 2-propanol, 1-butanol, 2-butanol, t-butanol, 1-pentanol, 1-hexanol, as well as the various other isomers of pentanol and hexanol; alkylene glycols such as ethylene glycol, diethylene glycol, triethylene glycol, 1,2-propylene glycol, 1,3-propane diol, dipropylene glycol, tripropylene glycol 1,4-butane diol and 1,2-butane diol; triols such as glycerine, and the like., and is preferably ethanol, 1,2-propylene glycol, glycerol, or 1,3-propane diol.

When the 1,4-pentanediol or the ketal alcohols (1), such as (1a), (1b), or a combination comprising at least one of the foregoing is present to disperse particles into an oil phase, the 1,4-pentanediol or the ketal alcohols (1), such as (1a), (1b), or a combination comprising at least one of the foregoing can be a partially-water miscible type or a sparingly water-miscible type. It is also possible in some cases to use fully-water-miscible types in that instance.

A wide variety of particles can be used in the particulate solid phase. The particles are a crystalline or non-crystalline solid under the conditions of manufacture, storage, and use, and can be organic, inorganic, or inorganic-organic. "Inorganic-organic" as used herein means a material that has both inorganic and organic components, such as an organic material that is precipitated by interaction with an inorganic material precipitated onto an inorganic particle (as a lake pigment), or otherwise sorbed onto and/or into the particle. In some cases, the particles can be surface treated through reaction with the functional groups on the surface, e.g., by silanation, zirconation, or addition of a cyclic dimethylsiloxane. Surface treatments can change the wetting or dispersing characteristics or be used for aesthetic effect. The particles are insoluble in the ketal alcohol (1) (although it can absorb the ketal alcohol (1) or in some cases be swelled by the ketal alcohol (1)), and are insoluble in any other dispersant or the continuous phase in which they are contained. The particles can be malleable. The particles can be pigment particles, or other solids including for example natural finely divided ores, minerals, sparingly soluble or insoluble salts, particles of wax or plastic, dyes that are insoluble in the ketal alcohol (1) or continuous phase, crop protection and pest control agents, UV absorbers, optical brighteners and polymerization stabilizers.

Organic particles include biological and organic pigments such as quinacridone, alizarin crimson, gamboge, cochineal red, rose madder, Indian yellow, phthalo green, phthalo blue, pigment red 170 and the like.

Inorganic pigments are useful as the solid particulate phase. The pigments can be white, black, or otherwise colored. Mixtures of pigments can be used. Suitable inorganic pigments include, for example, cadmium yellow, cadmium red, cadmium green, cadmium orange, carbon black, ivory black, iron oxide black, chrome yellow, chrome green, cobalt violet, cobalt blue, cerulean blue, aureolin (cobalt yellow), Han purple, Egyptian blue, Paris green, verdigris, viridian, sanguine, caput mortuum, iron oxide red, red ochre, Venetian red, Prussian blue, yellow ochre, raw sienna, burnt sienna, raw umber, burnt umber, lead white, cremnitz white, Naples yellow, red lead, vermilion, titanium yellow, titanium beige, titanium oxide, titanium black, ultramarine, ultramarine green and the like.

Inorganic-organic pigments include the so-called "Lake" pigments such as the various Red Al Lake, Red Ba Lake, Red Zn Lake, Red Talc Lake, Blue Al Lake, Yellow Al Lake pigments, as well as other lake pigments.

Various other inorganic compounds, minerals, and clays are also of interest as the solid particulate phase. These include, for example, calcium carbonate, magnesium aluminum silicate, magnesium trisilicate, attapulgite, bentonite, hectorite, lithium magnesium silicate, lithium magnesium sodium silicate, montmorillonite, boron nitride, silicon nitride, titanium carbide, boron carbide, mullite, coreiderite, and the like.

Metal powders are also useful as the solid particulate phase. Examples of these include aluminum, iron, steel, silver, bronze, copper, chromium, and the like.

The particles can have a particle size as small as about 10 nanometers up to 100 micrometers, for example from 10 nanometers to 25 micrometers. A more typical particle size is from 100 nanometers to 25 micrometers.

In an embodiment, a dispersion comprises a liquid or semi-solid continuous phase, at least one organic, inorganic, or inorganic-organic particulate dispersed within the continuous phase, 1,4-pentanediol or the ketal alcohols (1), such as (1a), (1b), or a combination comprising at least one of the foregoing is present in the continuous phase and/or on the surface of the dispersed particles. Metallic pigments can be highly elongated in shape and may be as large as several hundred micrometers in length.

A wide variety of materials and formulations can be used as the liquid or semi-solid phase. Liquid phases are flowable, and can be aqueous, organic, or a combination thereof, for example a combination of water and a water-miscible alcohol or other organic solvent. Semi-solid phases can be thixotropic, that is, flowable under a force. Semi-solids include gels, malleable materials such as waxes, wax blends, or wax/oil blends, amorphous and semi-crystalline polymers, and combinations thereof. It is to be understood that the term "continuous phase" is used in contrast to the solid particulate phase. Thus, a continuous phase can itself have more than one phase, for example an oil-in-water or a water-in-oil emulsion, a latex, or a semi-crystalline polymer. When the continuous phase is an emulsion, the solid particles will generally be present in the continuous phase of the emulsion, although it is possible for the particles to be sequestered in the discontinuous phase of the emulsion.

Other adjuvants can be present in the dispersions (for example the ink dispersions described below), depending on the intended use of the dispersion. These other adjuvants include, for example, other wetting agents that enhance the particle wetting; and other dispersants and surfactants that further enhance dispersion and or dispersion stability; and combinations comprising at least of the foregoing. Anionic, cationic, amphoteric, or nonionic surface-active compounds are typically used for these purposes, for example compounds having one or more C8 or longer hydrocarbyl chains, in some instances also having aromatic ring groups. Specific, nonlimiting examples are alkyl sulfates such as lauryl sulfate, stearyl sulfate, or octadecyl sulfate, primary alkyl sulfonates such as dodecyl sulfonate, and secondary alkyl sulfonates, particularly the C13-C17 alkanesulfonate sodium salt, alkyl phosphates, alkylbenzenesulfonates such as dodecylbenzenesulfonic acid, and salts thereof. Also useful are soy lecithin and condensation products of fatty acid and turbine or hydroxyethanesulfonic acid, similarly alkoxylation products of alkylphenols, castor oil resin esters, fatty alcohols, fatty amines, fatty acids and fatty acid amides, which alkoxylation products can similarly have ionic end groups, for example in the form of sulfosuccinic monoesters or else as sulfonic, sulfuric and phosphoric esters, and also salts thereof (sulfonates, sulfates or phosphates). Alkoxylated addition compounds obtained by reaction of polyepoxides with amines or bisphenol-A or bisphenol-A derivatives with amines can also be used. Nonionic alkoxylated styrene phenol condensates can be used, for example those obtained by addition of optionally substituted styrenes onto optionally substituted phenols and reaction with ethylene oxide and/or propylene oxide, as well as ionically modified derivatives thereof, for example as sulfonic, sulfuric and phosphoric esters, and salts thereof (sulfonates, sulfates or phosphates). Other useful surface-active compounds include lignosulfonates and polycondensates of naphthalinesulfonic acid and formaldehyde, or else of alkylarylsulfonic acids, haloarylsulfonic acid, sulfonated phenols, or sulfonated naphthols with formaldehyde.

Another class of adjuvants includes organic solvents or water-soluble hydrotropic substances. Hydrotropic substances can also serve as a solvent, and can be monomeric, oligomeric, or polymeric, for example formamide, urea, tetra-methylurea, ε-caprolactam, ethylene glycol, propylene glycol, diethylene glycol, triethylene glycol, polyethylene glycol, α-methyl ω-hydroxy polyethylene glycol ether, dimethyl polyethylene glycol ether, dipropylene glycol, polypropylene glycol, dimethyl polypropylene glycol ether, copolymers of ethylene glycol and propylene glycol, butyl glycol, methylcellulose, glycerol, diglycerol, polyglycerol, N-methyl-pyrrolidone, 1,3-diethyl-2-imidazolidinone, thiodiglycol, sodium benzenesulfonate, sodium xylenesulfonate, sodium toluenesulfonate, sodium cumenesulfonate, sodium dodecylsulfonate, sodium benzoate, sodium salicylate, sodium butyl monoglycol sulfate, cellulose derivatives, gelatin derivatives, polyvinylpyrrolidone, polyvinyl alcohol, polyvinylimidazole and co- and terpolymers of vinylpyrrolidone, vinyl acetate and vinylimidazole. Polymers comprising vinyl acetate building blocks may subsequently be saponified to the vinyl alcohol.

Also useful in the dispersions are, for example thickeners, preservatives, viscosity stabilizers, grinding assistants, fillers, antisettling agents, photoprotectants, antioxidants, degassers/defilmers, foam-reducing agents, anticaking agents, and viscosity and rheology improvers. Useful viscosity regulators include polyvinyl alcohol, and cellulose derivatives, including polysaccharides, associative thickeners, such as hydrophobically modified nonionic systems (such as hydrophobe modified ethoxylate urethane), hydrophobically modified cellulosics (such as hydrophobe modified hydroxyethyl cellulose), and hydrophobe modified alkali-swellable latex, attapulgite clays, bentonite clays, organoclays, synthetic silicas like precipitate silica, fumed silica, organosilica, and synthetic organic systems such as castor oil derivatives, modified acrylic copolymers, polyethylene glycol, polymerized, and the like. Water-soluble or organic solvent-soluble natural or manufactured resins and polymers may similarly be included as filming or binding agents to enhance bonding strength and abrasion resistance. Useful pH regulators include organic bases, for example such as are amines, for example ethanolamine, diethanolamine, triethanolamine, N,N-dimethylethanolamine, diisopropylamine, aminomethylpropanol or dimethylaminomethylpropanol; or inorganic bases such as sodium hydroxide, potassium hydroxide, lithium hydroxide or ammonia; and organic or inorganic acids. The dispersions can further include fats and oils of vegetable and animal origin, for example beef tallow, palm kernel fat, coconut fat, rapeseed oil, sunflower oil, linseed oil, palm oil, soy oil, groundnut oil and whale oil, cotton seed oil, maize oil, poppy seed oil, olive oil, castor oil, colza oil, safflower oil, soybean oil, thistle oil, sunflower oil, herring oil, and sardine oil. Other oils include tall oil, which is obtained from sulfate or Kraft pulping of pine and other softwoods, and tung oil, which is obtained from seeds of certain trees. Common additives also include saturated and unsaturated higher fatty acids, for example palmitic acid, caprylic acid, capric acid, myristic acid, lauryl acid, stearic acid, oleic acid, linoleic acid, linolenic acid, caproic acid, caprylic acid, arachidic acid, behenic acid, palmitoleic acid, gadoleic acid, erucic acid and ricinoleic acid, licanic acid, eleostearic acid, as well as salts thereof.

The particles can be dispersed into the liquid continuous phase in several ways. They can be wetted with the ketal alcohol (1) and optionally one or more other adjuvants, for example a wetting agent, and then dispersed into the liquid continuous phase. The ketal alcohol (1) can instead (or in addition) be incorporated into the liquid continuous phase before dispersing the particles. Alternatively, the three components can be simultaneously combined. Other components of the compositions can be added at any step in the foregoing methods.

Thus, in an embodiment, a method of forming a dispersion comprises wetting the organic, inorganic or inorganic-inorganic particles with an ketal alcohol (1) I and then mixing the wetted particles with a liquid to form a dispersion in which the liquid forms all or part of the continuous phase and the particles form a disperse phase. In another embodiment, a method of forming a dispersion comprises mixing organic, inorganic, or inorganic-inorganic particles into a continuous liquid phase which contains an ketal alcohol (1) I. In still another embodiment, a method of forming a dispersion comprises simultaneously combining the organic, inorganic, or inorganic-inorganic particles, the ketal alcohol (1) I, and the liquid of the liquid phase.

In a specific embodiment, the solid particles (or materials for comminution into the solid particles) are predispersed, for example with 1,4-pentanediol or the ketal alcohols (1), such as (1a), (1b), or a combination comprising at least one of the foregoing and optionally other wetting agent or dispersing aid. The predispersion is subsequently, depending on the size and/or shape of the particles, finely dispersed or finely dissipated, with or without cooling, using a grinding or dispersing assembly, for example stirrers, dissolvers (sawtooth stirrers), rotor-stator mills, ball mills, stirred media mills such as sand and bead mills, high speed mixers, kneaders, roll stands or high performance bead mills. The fine dispersing or grinding of the solid particles and the ketal alcohol (1) component is carried on to the desired particle size distribution and can take place at 0 to 100° C., 10 to 70° C., or 20 to 60° C., for example. Following the fine-dispersing operation, the particles can be further diluted with a material of the continuous phase. Concentrates can be formed, for later addition to the other ingredients of the dispersion. Alternatively, the particles can be reduced to the desired particle size, and then combined with 1,4-pentanediol or the ketal alcohol (1).

In an embodiment, a dispersion, in particular a coating composition comprises a liquid continuous phase and a dispersed phase comprising particles of a solid pigment. The coating composition further contains 1,4-pentanediol or the ketal alcohols (1), such as (1a), (1b), or a combination comprising at least one of the foregoing, which can be present in the continuous phase and/or on the surface of the dispersed pigment particles. The pigment particles can be organic, organic-inorganic, or inorganic. In an embodiment, the pigment particles are inorganic.

The coating composition can be, for example, a paint, a sealant, an ink, or other composition containing dispersed pigment particles. Coating compositions of this type generally contain a continuous liquid phase that can be aqueous (including a mixture of water and a water-miscible solvent such as an alcohol), organic, or in the form of an emulsion; a binder resin; and the pigment. Other adjuvants, for example as described above can be present as is known in the art, depending on the intended purpose of the coating composition.

The coating composition can contain from 20 to 90% by weight of the liquid continuous phase; from 5 to 80% by weight of the binder resin; from 0.5 to 45% by weight, or from 0.5 to 35% by weight of one or more organic or inorganic pigments; and from 0.5 to 60% by weight of the 1,4-pentanediol or the ketal alcohol (1), or from 1 to 25% by weight or from 1 to 10% by weight, each based on the total weight of the liquid coating composition. In another embodiment, the 1,4-pentanediol or the ketal alcohols (1), such as (1a), (1b), or a combination comprising at least one of the foregoing can be present in an amount effective to function as part of the liquid continuous phase. In these embodiments, coating composition can contain from 5 to 90% by weight of the liquid continuous phase; from 5 to 70% by weight of the binder resin; from 0.5 to 25% by weight, or from 0.5 to 15% by weight of the organic or pigment particles; and from 0.5 to 89.5% by weight, from 1 to 25% by weight, or from 1 to 10% by weight of the 1,4-pentanediol or the ketal alcohols (1), such as (1a), (1b), or a combination comprising at least one of the foregoing, each based on the total weight of the coating composition.

In a specific embodiment, the coating composition is a paint composition. Paint compositions can be aqueous (e.g., a latex), organic, or in the form of an emulsion (e.g., asphalt emulsion coatings for roofs, which can contain bentonite clay in solid particulate form). Further uses are the production of wood preservation systems, varnishes, and the like.

In another embodiment, the coating composition is a liquid ink, for example for felt tip pens, graphics inks ballpoint pens, and ink jet ink. Inks can be aqueous or organic-solvent based, microemulsion inks, UV-curable inks, and inks that operate in a the hot melt process. Further uses are the production of printing colors, for example, flexographic printing inks or intaglio printing inks. In a specific embodiment, the liquid printing inks can be used in any ink-jet printers, particularly those using the bubble jet or piezo process. These liquid printing inks can be used to print paper and also natural or synthetic fiber materials, foils and plastics. Additionally, the coating compositions can be used for printing various kinds of coated or uncoated substrate materials, for example for printing paper board, cardboard, wood, and wood-based materials, metallic materials, semiconductor materials, ceramic materials, glasses, glass and ceramic fibers, inorganic materials of construction, concrete, leather, comestibles, cosmetics, skin and hair. The substrate material may be two-dimensionally planar or spatially extended, i.e., three-dimensionally configured, and may be printed or coated completely or only in parts.

The dispersions comprising a liquid or semi-solid continuous phase, a particulate phase dispersed within the continuous phase, and 1,4-pentanediol or the ketal alcohol (1) can be used as cosmetic formulations and products, for example in wet foundations, skin care products, eyeliner, mascara, or lip care product. For convenience, the liquid or semi-solid continuous phases may be referred to herein as a "carrier." The dispersed particles can be pigments or other types of particles, for example silica, mica, or an active agent such as benzoyl peroxide, or other solids in particulate form. Eye care products are products to be applied on the eye lids, around the eyes, on the eyebrows, or on the eyelashes, and can include eyeshadow, eyeliner, and mascara. Skin products are products applied on the skin (face or body), and can include lotions and creams for hand, face, or body, deodorant/anti-perspirant, and facial cosmetics like foundation, concealer, blush, bronzer, and the like. Lip care products are products applied to the lips, and can include lipstick, lipgloss, lipbalm, lip liner pencil, lip liner pencil stick, and the like. Nail products are products applied to a the nails or cuticles (or both), and can include nail polishes.

Wet foundations are typically liquids or creams. They typically contain an aqueous liquid phase and an oily phase, either of which can be continuous. These products are in most cases both dispersions and emulsions, in that they often contain a continuous liquid phase, a dispersed liquid phase, and a dispersed solid phase. The pigment can be dispersed into either phase, although it is more typically dispersed into at least the continuous phase. Water can constitute 30 to 75% of the weight of a wet foundation product. Pigments generally constitute from 2 to 25% by weight of a wet foundation. Emollients can constitute from 1 to 35% by weight of a wet foundation. A surfactant is often present in an amount from 0.1 to 15% by weight. The ketal alcohol (1) can constitute from 0.5 to 35% by weight of a wet foundation. Other ingredients can include, for example, thickeners, preservatives, cosolvents, and the like.

A fluid or gel eyeliner typically contains from 25 to 80% by weight of water and/or one or more volatile organic solvents, from 2 to 35% of a wax, film-forming polymer, and/or emollient, from 2 to 30% by weight of the pigment, and from 1 to 40%, or 25% by weight of the 1,4-pentanediol or the ketal alcohols (1), such as (1a), (1b), or a combination comprising at least one of the foregoing. These products are often both emulsions and dispersions. This type of product can also contain one or more thickeners or gelling agents, one or more surfactants or cosolvents that can function as a stabilizer for the emulsified wax, film-forming polymer, and/or emollients. They can also contain other ingredients, such as preservatives.

A mascara product can be, for example, an oil-in-water emulsion, a water-in-oil emulsion, or an anhydrous organic formulation, in each case containing dispersed pigment particles. A mascara product typically contains one or more waxes or film-forming polymers. They can also contain one or more emollients, thickeners, surfactants, or cosolvents (which can serve as stabilizer for the emulsified wax or film-forming polymer), preservatives, or other ingredients. A mascara product can contain from 1 to 25% by weight of dispersed pigment particles, from 5 to 50% by weight of a wax and/or film-forming polymer, from 25 to 75% by weight of water and/or organic solvent, and from 1 to 50%, or from 1 to 25% by weight of the 1,4-pentanediol or the ketal alcohols (1), such as (1a), (1b), or a combination comprising at least one of the foregoing.

Lip care product such as lipsticks and lip glosses are typically in stick form or in the form of a thick liquids or pastes. Many lip care products include a mixture of one or more waxes with one or more oils and, in the case of lipsticks at least, one or more pigments. It is understood that those skilled in the art can design the stick formulations to have the proper stick stability and product delivery (deposition of color on the lips, for instance) through proper selection of wax blends and other ingredients. These products are normally characterized as being anhydrous. A lip care product formulation can contain, for example, from 1 to 25%, or 20% by weight of a wax; from 30%, or from 50 to 95% by weight of one or more other hydrophobic materials, of which castor oil is often an important component especially in lipsticks; from 0.051 to 25%, or 10% by weight of one or more pigments, more typically at least 1% in the case of lipsticks, and from 1 to 50%, or from 1 to 25% by weight of the 1,4-pentanediol or the ketal alcohols (1), such as (1a), (1b), or a combination comprising at least one of the foregoing.

Cosmetic products such as those described, in which the pigment or other particles are dispersed in a carrier (the liquid or semi-solid continuous phase), can be prepared in several ways. The particles can be wetted with the ketal alcohol (1), prior to dispersing them into the carrier. Alternatively (or in addition), the ketal alcohol (1) can be blended into the carrier prior to dispersing the pigment or particles into it, or the components can be combined simultaneously.

A wide variety of carriers can be used in the cosmetic formulations and products, depending on the end use of the cosmetic and the desired characteristics. Generally, the carrier includes at least one (a) paraffinic, naphthenic or aromatic mineral oil, (b) nonionic organic compounds which has a melting temperature of less than 45° C., has a molecular weight of at least 190, contains at least one amido, or ester group and at least one alkyl chain containing at least 8 carbon atoms, and has a solubility in water of no greater than 1 part in 99 parts of water; (c) nonionic organosilicone compound which has a melting temperature of less than 45° C. and has a solubility in water of no greater than 1 part in 99 parts of water; (d) long chain alcohol, (e) wax, or (f) film-forming polymer. At least one ketal alcohol (1) is present in the carrier, or sorbed onto or into the solid pigment particles, or both. The specific ingredients and relative proportions of the foregoing ingredients will depend on the form of the specific cosmetic product. An eyeliner, for example, can take the form of a somewhat viscous fluid or gel, or can be a malleable stick product. An eyeliner generally contains (1) at least one wax or at least one film-forming polymer or (2) at least one emollient, or both (1) and (2), together with (3) at least one dispersed pigment. In stick and pencil products, the wax, film-forming polymer, and/or emollient can constitute, in the aggregate, from 25 to 80% of the total weight of the product, the pigments can constitute from 5 to 50% of the weight of the product, and the 1,4-pentanediol or the ketal alcohols (1), such as (1a), (1b), or a combination comprising at least one of the foregoing can constitute from 0.1 to 50%, 25%, or 10% of the weight of the product. Stick-type products typically contain no more than 10% by weight of water.

Components (a) include paraffinic, naphthenic, or aromatic mineral oils. These materials are often present as all or part of an oil phase in emulsion formulations such as certain lotions and creams. They often function as emollients that soften the skin upon application.

Useful component (b) materials include a wide range of vegetable oils and animal oils. Oils which have a required HLB of at least 6, or at least 7, tend to dissolve more easily in the ketal alcohol (1)s and are preferred in cases in which the ketal alcohol (1) is to reside at least partially in an oily phase, or in which the ketal alcohol (1) is to dissolve or be dissolved into the oil.

Other useful component (b) materials include, for example, C8-24 linear or branched alkyl esters of C8-24 fatty acids, di-C8-24 esters of dicarboxylic acids, C8-24 fatty acid esters of C8-24 linear or branched alkanoic acids, C8-24, especially C12-15 alkyl benzoates, poly(propylene oxide) esters of C8-24 fatty acids, di-C8-24 linear or branched alkyl esters of aromatic diacids, di-C8-24 fatty acid esters of aromatic diacids, and the like. Other useful component (b) materials include, for example, C8-24 linear or branched alkyl amides of C8-24 fatty acids, di-C8-24 amides of dicarboxylic acids, C8-24 fatty acid amides of C8-24 linear or branched alkanoic acids, poly(propylene oxide) amides of C8-24 fatty acids, di-C8-24 linear or branched alkyl amides of aromatic diacids, di-C8-24 fatty acid amides of aromatic diacids, and the like.

Examples of the component (c) materials are dimethicone and cyclopentasiloxane.

The component (d) materials are long chain (eight or more carbon atoms) alcohols such as 1-octanol, 1-decanol, 1-docecanol, cetyl alcohol, and the like.

Suitable waxes include synthetic or mineral waxes such as ceresin, montan, ozocerite, peat, paraffin, microcrystalline, polypropylene and other polymerized poly-α-olefin waxes, substituted amide, petroleum jelly, esterified or saponified waxes, and the like; and waxes of plant or animal origin including beeswax, chinese wax, lanolin, shellac wax, spermaceti, bayberry, candelilla, carnauba, castor, esparto, Japan, ouricury, rice bran or soy waxes.

Among the useful film-forming polymers (component (f)) are corn starch (modified), acrylates/octylacrylamide copolymer, polyurethane-14 and AMP-acrylates copolymer, hydrolyzed wheat protein, polyvinylpyridine (PVP), hydrolyzed wheat protein/PVP crosspolymer, vinyl acetate/crotonates/vinyl neodecanoate copolymers, potassium butyl ester of PVM/MA copolymer, polyurethane-14 & AMP-acrylates copolymer, isobutylene/ethyl maleimide/hydroxylethylmaleimide copolymer, polyvinylpyrrolidone/vinyl acetate polymers, acrylates/hydroxyesters acrylates copolymer, polyurethanes, polyvinyl methyl ester/maleate, octylacrylamide/acrylates/butylaminoethyl methacrylate copolymer, nitrocellulose, cellulose acetate propionate, cellulose acetate butyrate, styrene/acrylates copolymers, acrylates copolymers and polyethylene terepthalate and the like.

A composition can include a surfactant, which can include ionic (cationic, anionic, or zwitterionic) compounds that contain a hydrocarbon group of at least 8 carbon atoms. The hydrocarbon group preferably includes at least one alkyl group having at least 8 carbon atoms. The ionic surfactants include, for example, anionic surfactants which include one or more sulfate, sulfonate or phosphate groups, which are in the neutralized (or "salt") form; cationic surfactants which include one or more quaternary ammonium or quaternary phosphonium groups, which are in the neutralized (or "salt") form; one or more zwitterionic groups which can, depending on the pH of the product, assume either an anionic or cationic form (as with the betaines, for example), or can assume a cationic or nonionic form (as with the amine oxide surfactants, for example). The emulsifier may be generated in-situ, for example, when stearic acid is added to the oil phase, and triethanol amine is added to the water phase and the TEA-stearate salt forms when the oil and water phases are mixed.

The cosmetics can, of course, contain any of a wide range of other ingredients as needed or desired for a particular end-use application.

In another aspect, this invention is a particulate organic, inorganic, or inorganic-organic solid in which the particles are at least partially coated with 1,4-pentanediol or a ketal alcohol (1). The 1,4-pentanediol or the ketal alcohols (1), such as (1a), (1b), or a combination comprising at least one of the foregoing can, in this aspect, function as a slip agent (by lubricating the particles) and/or as a dispersing aid. The 1,4-pentanediol or the ketal alcohol (1) is present in an amount effective to perform the desired function, for example from 0.1 to 100%, from 0.1 to 50%, from 1 to 30%, or from 1 to 10% by weight of the particulate solid. It is to be understood that the term "coated" as used herein includes embodiments where the 1,4-pentanediol or the ketal alcohol (1) is at least partially absorbed into the particles.

The at least partially coated particles can be used in the dispersions described above, i.e., as the particulate phase dispersed in a liquid or semi-solid continuous phase. The at least partially coated particles can be easily dispersed into a variety of fluids due to the presence of the 1,4-pentanediol or the ketal alcohols (1), such as (1a), (1b), or a combination comprising at least one of the foregoing, which renders the surface of the particles compatible with those fluids. In other embodiments, the at least partially coated particles are used in the manufacture of dry compositions, for example in the form of a dry or nearly dry powder, an oily powder, or a paste, depending on the amount of 1,4-pentanediol or the ketal alcohols (1), such as (1a), (1b), or a combination comprising at least one of the foregoing present. As used herein "dry" compositions are distinguished from the above-described dispersions by the lack of a liquid or semi-solid continuous phase.

A variety of solids as described above can be used as the particulates in these embodiments. In an aspect, the solid particulate is a solid pigment as described above. A solid inorganic pigment can be particularly mentioned. As described above, the at least partially coated solid pigment can be easily dispersed into a variety of liquid and semi-solid, aqueous and non-aqueous systems, and thus can be easily incorporated into various products such as paints, inks and cosmetics of the type described before. The cosmetics contain the particulate solids at least partially coated with 1,4-pentanediol or the ketal alcohols (1), such as (1a), (1b), or a combination comprising at least one of the foregoing and an ingredient (a)-(f) or a combination thereof.

In other embodiments, the at least partially coated pigments are used in the manufacture of dry compositions, for example in the form of a dry or nearly dry powder, an oily powder, or a paste, depending on the amount of 1,4-pentanediol or the ketal alcohols (1), such as (1a), (1b), or a combination comprising at least one of the foregoing present. The at least partially coated pigments can be useful as, for example, a dry pigment, toner, or powder coating. The ketal alcohol (1) I can constitute from 0.1 to 100%, from 0.1 to 50%, from 1 to 30%, or from 1 to 10% by weight of the particulate pigment.

The at least partially coated pigment particles, in particular at least partially coated inorganic pigment particles, can be useful in dry cosmetic formulations and products. (Of course, other solid particulates at least partially coated with ketal alcohol (1), such as silica, can also be used). In an embodiment, a powder cosmetic comprises a solid pigment and 1,4-pentanediol or the ketal alcohols (1), such as (1a), (1b), or a combination comprising at least one of the foregoing. Such a cosmetic can be, for example, a powder color cosmetic product, a powder cream cosmetic product, a pressed powder color cosmetic product, a blush, or an eye shadow.

In another aspect, a solid pigment having at least one 1,4-pentanediol or the ketal alcohols (1), such as (1a), (1b), or a combination comprising at least one of the foregoing sorbed onto or into the solid pigment particles is described. Blushes, pressed powder eye shadows, and dry foundations are examples of such pigment compositions. Blushes, pressed powder eye shadows, and dry foundations are typically powders, which can be free-flowing or somewhat caked. In these powder products, the pigment(s) typically constitute from 50 to 95% by weight of the product. The 1,4-pentanediol or the ketal alcohols (1), such as (1a), (1b), or a combination comprising at least one of the foregoing can constitute from 0.1 to 15%, from 1 to 12%, or from 1 to 10% by weight of the product. Other filler particles can be present in amounts from 1 to 95% by weight of the product. In a powder cream, the 1,4-pentanediol or the ketal alcohols (1), such as (1a), (1b), or a combination comprising at least one of the foregoing can constitute from 0.1 to 40%, from 1 to 30%, or from 1 to 20% by weight of the product, optionally together with other filler particles, which can be present in amounts from 1 to 95% by weight of the powder cream product. The 1,4-pentanediol or the ketal alcohols (1), such as (1a), (1b), or a combination comprising at least one of the foregoing can function in these products as a slip agent that allows the particles to adhere slightly yet spread easily upon application. Emollients can be present in an amount, for example, of from 1 to 25% by weight of the product. Preservative, film-forming polymer and other optional ingredients can be present. These products typically contain no more than 1% by weight of water, and can contain water scavengers to prevent caking.

The solid particulates at least partially coated with 1,4-pentanediol or the ketal alcohols (1), such as (1a), (1b), or a combination comprising at least one of the foregoing also can be incorporated into various organic polymers, to produce, for example, pigmented polymers and/or filled or reinforced polymers. The at least partially coated solid particulates can also be used as colorants for color filters for flat panels displays, not only for additive but also for subtractive color production; coloration of macro-molecular materials of any kind, for example natural and synthetic fiber materials, for example cellulose fibers; for paper pulp coloration; laminate coloration; textile printing colors; wallpaper colors, viscose dope dyeing systems; powder coatings; sausage casings; coloration of seed, fertilizers, glass, particularly glass bottles, roof shingles, renders, concrete, wood stains, colored pencil leads, chalks, waxes, paraffins, shoe care agents, latex products, abrasives, photoresists, floor and car waxes, crayons, coatings for foods (such as wax coatings for cheeses), leather polishes, nail polishes, and as colorants for "electronic inks" ("e-inks") and "electronic paper" ("e-paper").

The solid particulates at least partially coated with 1,4-pentanediol or the ketal alcohols (1), such as (1a), (1b), or a combination comprising at least one of the foregoing are also useful as a colorant in electrophotographic toners and developers, for example in one- or two-component powder toners (also called one- or two-component developers), magnet toners, liquid toners, latex toners, polymerization toners and also specialty toners. Typical toner binders in this context are addition polymerization resins, polyaddition resins and polycondensation resins, such as styrene, styrene-acrylate, styrene-butadiene, acrylate, polyester, phenol-epoxy resins, polysulfones, polyurethanes, individually or in combination, and also polyethylene and polypropylene, which may each contain further ingredients, such as charge control agents, waxes or flow assistants, or are subsequently modified with these adjuvants.

Use of the 1,4-pentanediol or the ketal alcohols (1), such as (1a), (1b), or a combination comprising at least one of the foregoing allows excellent dispersion of solid particles in liquid and semi-solid phases. The performance of the products containing the dispersions can have enhanced performance due to the characteristics of the dispersion, e.g., the targeted viscosity, and the uniformity of the dispersion. The dispersions can be stable over time (e.g., one week, one month, six months, one year, or even longer).

Use of the 1,4-pentanediol or the ketal alcohols (1), such as (1a), (1b), or a combination comprising at least one of the foregoing can also improve the ability to form the dispersions, as well as the stability of those dispersions. These characteristics are influenced by factors such as the affinity of the particle surfaces to the dispersing medium and the density of the particles relative to the density of the dispersing medium. In general, particles become harder to disperse and harder to maintain in dispersion as their surfaces become less compatible with the dispersing medium and as the difference in density between particles and dispersing medium becomes greater. Without being bound by theory, it is believed that the 1,4-pentanediol or the ketal alcohols (1), such as (1a), (1b), or a combination comprising at least one of the foregoing described herein can function as a compatibilizer between the particles and the dispersing medium. The differing solubilities of the 1,4-pentanediol or the ketal alcohols (1), such as (1a), (1b), or a combination comprising at least one of the foregoing allows selection of the appropriate ester depending on the particular solid and dispersing medium. Formulation of various dispersions is therefore simplified, as the number of dispersants to be tested is decreased for a given formulation. In cases where a fully water-miscible ketal or a partially water-miscible is used to make the pigmented compositions or concentrates, the equipment can be quickly or easily cleaned with water, which has the advantage of being low-odor and environmentally friendly. In the case where a fully alcohol miscible ketal or a partially alcohol-miscible ketal is used, the equipment can be quickly or easily cleaned with alcohol, avoiding or minimizing the use of malodorous hydrocarbon solvents. The 1,4-pentanediol or the ketal alcohols (1), such as (1a), (1b), or a combination comprising at least one of the foregoing has the additional advantage of being bio-based, and may serve additional functions in the formulation, such as an emollient, a coalescent, or a cosolvent Latex Coating Compositions In another embodiment, the 1,4-pentanediol and the ketal alcohols (1) are useful in latex coating compositions, in particular latex paint compositions.

It has been found that the 1,4-pentanediol or the ketal alcohols (1), such as (1a), (1b), or a combination comprising at least one of the foregoing find use in latex coating compositions. Without being bound by theory, it is believed that the ketal alcohols function primarily as a coalescing solvent during the formation of coatings. However, it is to be understood that the ketal alcohols can have more than one function, including one or more of solubilization, solvent coupling, surface tension reduction, and the like.

The 1,4-pentanediol or the ketal alcohols (1), such as (1a), (1b), or a combination comprising at least one of the foregoing can be used in a variety of latex coating compositions, including paint, caulking, sealing, and ink compositions. Such compositions generally comprise latex that includes water and an emulsion of a polymeric binder effective to perform the desired function (i.e., painting, caulking, sealing, adhesion, or binding ink pigments) the 1,4-pentanediol or the ketal alcohols (1), such as (1a), (1b), or a combination comprising at least one of the foregoing, and optionally other components effective to perform the desired function of the composition. Thus, in an embodiment, a latex coating composition comprises a latex polymer binder, water, 1,4-pentanediol or the ketal alcohols (1), such as (1a), (1b), or a combination comprising at least one of the foregoing and an additive.

The polymer binder of the latex can be selected from a wide variety of polymers as known in the art of latex coating compositions, for example those described above for latex paint compositions. For instance, the latex polymer binder can be derived from monomers comprising at least one acrylic monomer such as acrylic acid, acrylic acid C1-10 alkyl esters, methacrylic acid, or methacrylic acid C1-10 alkyl esters, optionally copolymerized with one or more of styrene, hydroxyethyl acrylate, hydroxypropyl acrylate, α-methyl styrene, vinyl chloride, acrylonitrile, methacrylonitrile, ureido methacrylate, vinyl acetate, vinyl esters of branched tertiary monocarboxylic acids (e.g., vinyl esters of versatic acid commercially available under the trademark VeoVa® from Shell Chemical Company or the trademark Exxar® Neo Vinyl Esters from ExxonMobil Chemical Company), itaconic acid, crotonic acid, maleic acid, fumaric acid, and ethylene. It is also possible to include C4-8 conjugated dienes such as 1,3-butadiene, isoprene, and chloroprene. In an embodiment, the monomers include one or more of n-butyl acrylate, methyl methacrylate, styrene, and 2-ethylhexyl acrylate.

Pure acrylics can be used (comprising acrylic acid, methacrylic acid, an acrylate ester, and/or a methacrylate ester); styrene-acrylics (comprising styrene and acrylic acid, methacrylic acid, an acrylate ester, and/or a methacrylate ester); urethane-acrylics vinyl-acrylics (comprising vinyl acetate and acrylic acid, methacrylic acid, an acrylate ester, and/or a methacrylate ester); acrylated ethylene vinyl acetate copolymers (comprising ethylene, vinyl acetate and acrylic acid, methacrylic acid, an acrylate ester, and/or a methacrylate ester), and acrylamide and acrylonitrile, optionally together with monomers such as itaconic acid and ureido methacrylate.

The latex polymer binder is present in water in the form of an aqueous emulsion, and can include about 2 to about 75 weight percent (wt. %) solids, specifically about 5 to about 70 wt. % solids (i.e., the weight percentage of the dry polymer latex based on the total weight of the aqueous latex coating composition). The latex can be present in a wide variety of particle sizes, for example a mean latex particle size from about 10 to about 1,000 nanometers (nm), specifically about 50 to about 800 nm. The particle size distribution can be mono-modal or multimodal, for example bimodal. The 1,4-pentanediol or the ketal alcohols (1), such as (1a), (1b), or a combination comprising at least one of the foregoing is present in the latex coating composition in an amount effective for its purpose, i.e., coalescence of a coating, solubilization, and the like. Such amounts can be determined by one of ordinary skill in the art, and can be for example, from about 0.1 to about 30 wt. %, specifically about 0.5 to about 20 wt. %, based on the total weight of the latex coating compositions. The balance of the latex coating compositions is water and other optional additives known in the art.

In a specific embodiment, the 1,4-pentanediol or the ketal alcohols (1), such as (1a), (1b), or a combination comprising at least one of the foregoing are used in latex paint compositions, and can reduce or replace other organic solvents in the latex paint compositions. 1,4-pentanediol or the ketal alcohols (1), such as (1a), (1b), or a combination comprising at least one of the foregoing in particular can be used as a green/non-toxic coalescing solvent in latex paint compositions, and in particular paints used in architectural and light industrial applications. More efficient coalescing, specifically, lower quantities of the ketal alcohol can generally be used to obtain a particular minimum film formation temperature. In addition it has been observed that the present invention includes latex paint compositions with a less objectionable odor as compared to latex paint compositions formulated with commonly used organic solvents.

Thus, in one embodiment, a latex paint composition comprises a latex polymer binder, often two or more polymer binders, water, 1,4-pentanediol or the ketal alcohols (1), such as (1a), (1b), or a combination comprising at least one of the foregoing, and optionally a pigment.

A wide variety of latex polymer binders can be used, including those described above. Acrylics can be specifically mentioned, formed from one or more of acrylic acid, methacrylic acid, C1-10 alkyl acrylate ester, or C1-10 alkyl methacrylate ester monomers. Styrene-acrylics formed from styrene and at least one of acrylic acid, methacrylic acid, C1-10 alkyl acrylate ester, or C1-1-alkyl methacrylate ester monomers can be used. Other latexes include vinyl-acrylics formed from vinyl acetate and at least one of acrylic acid, methacrylic acid, C1-10 alkyl acrylate ester, or C1-10 alkyl methacrylate ester monomers. Acrylated ethylene-vinyl acetate copolymers can be used, formed from ethylene, vinyl acetate, and at least one of acrylic acid, C1-10 alkyl acrylate ester, or C1-10 alkyl methacrylate ester monomers. The foregoing polymers can also include other monomers such as acrylamide, acrylonitrile, itaconic acid, and ureido methacrylate.

A pigment can be present in the latex paint composition. The term "pigment" as used herein includes non-film-forming solids such as extenders and fillers, for example an inorganic pigment TiO2 (in both anastase and rutile forms), clay (aluminum silicate), CaCO3 (in both ground and precipitated forms), aluminum oxide, silicon dioxide, magnesium oxide, talc (magnesium silicate), barites (barium sulfate), zinc oxide, zinc sulfite, sodium oxide, potassium oxide, solid (high Tg) organic latex particles added to modify hardness or surface roughness or (as in the case of hollow latex particles) to replace TiO2, and a combination comprising at least one of the foregoing. Representative combinations include blends of metal oxides such as those sold under the marks Minex® (oxides of silicon, aluminum, sodium and potassium commercially available from Unimin Specialty Minerals), Celites® (aluminum oxide and silicon dioxide commercially available from Celite Company), Atomites® (commercially available from English China Clay International), and Attagels® (commercially available from Engelhard). Specifically, the pigment includes TiO2, CaCO3, or clay.

Generally, the mean particle sizes of the pigments are about 0.01 to about 50 micrometers. For example, the $TiO_2$ particles used in the aqueous coating composition typically have a mean particle size from about 0.15 to about 0.40 micrometers. The pigment can be added to the aqueous coating composition as a powder or in slurry form.

The latex paint composition can contain additional additives, as known in the art, to modify the characteristics of the latex paint composition, provided that the additives do not significantly adversely affect the desired properties of the paint. These additives can include a plasticizer, drying retarder, dispersant, surfactant or wetting agent, rheology modifier, defoamer, thickener, biocide, mildewcide, colorant, wax, perfume, pH adjuster, or co-solvent. The additives are present in the amount ordinarily used in latex paint compositions. In an embodiment, the latex paint composition consists essentially of a latex polymer binder, water, an optional pigment, and a ketal alcohol (1), specifically (1a). As used herein, the phrase "consists essentially of" encompasses the latex polymer binder, water, optional pigment, and ketal alcohol, and optionally one or more of the additives defined herein, but excluding any additive that significantly adversely affects the desired properties of the latex paint composition or the dried coating derived therefrom.

The latex polymer binder can be present in the latex paint composition in a dry weight amount from about 5 to about 80 wt. %, and more specifically about 8 to about 60 wt. % of the latex paint composition.

When present, a pigment can be used in the latex paint composition in an amount from about 5 to about 75 wt. %, specifically about 10 to about 55 wt. % of the total solids in the latex paint composition.

The 1,4-pentanediol or the ketal alcohols (1), such as (1a), (1b), or a combination comprising at least one of the foregoing can be present in the latex paint composition in an amount from about 0.1 to about 30%, more specifically about 0.5 to about 20 wt. %, more specifically about 1 to about 15 wt. %, 1 to about 10 wt. %, more specifically about 1 to about 8 wt. %, and still more specifically about 1 to about 7 wt. %, based on the total weight of the latex coating composition.

Although much of the water in the latex paint is provided by the latex emulsion and in other components of the latex paint composition, water can be added separately to the latex paint composition during formulation thereof. Typically after formulation is completed, the latex paint composition includes about 10 to about 85 wt. % and more specifically about 20 to about 80 wt. % water, i.e., the total solids content of the latex paint composition is about 15 to about 90 wt. %, more specifically, about 20 to about 80 wt. % of the total composition. The compositions are typically formulated such that the hardened (dried) coatings comprise at least 5 volume % (vol. %) dry polymer solids and 5 to 90 vol. % of non-polymeric solids in the form of pigments.

In another embodiment, a latex caulking composition comprises a latex polymer binder, water, 1,4-pentanediol or the ketal alcohols (1), such as (1a), (1b), or a combination comprising at least one of the foregoing and a caulking additive, for example fillers, such as talc and calcium carbonate, mildewcides, biocides, pigments and plasticizers. The polymer binder of the caulking composition can be selected from a wide variety of polymers as known in the art of latex coating compositions, for example those described above for latex paint compositions. Additives include fillers, such as talc and calcium carbonate, mildewcides, biocides, antifoam agents, antifreeze agents, pigments and plasticizers The amounts of the latex polymer binder and the 1,4-pentanediol or the ketal alcohols (1), such as (1a), (1b), or a combination comprising at least one of the foregoing effective to form a latex caulking composition can be determined by one of ordinary skill in the art, and can be, for example, about 5 to about 80 wt. % of the polymer binder solids, based on the weight of the latex caulking composition, and about 0.1 to about 30% of the 1,4-pentanediol or the ketal alcohols (1), such as (1a), (1b), or a combination comprising at least one of the foregoing, more specifically between about 0.1 and 10% based on the dry weight of the polymer binder.

In another embodiment, a latex sealant or adhesive composition comprises a latex polymer binder, water, 1,4-pentanediol or the ketal alcohols (1), such as (1a), (1b), or a combination comprising at least one of the foregoing and a sealant or adhesive additive, for example a pigment. The polymer binder of the sealant or adhesive can be selected from a wide variety of polymers as known in the art of latex coating compositions, for example those described above for latex paint compositions. Additives include fillers, such as talc and calcium carbonate, mildewcides, biocides, pigments, antifoam agents, antifreeze agents, tackifiers and plasticizers. The amounts of the latex polymer binder and the 1,4-pentanediol or the ketal alcohols (1), such as (1a), (1b), or a combination comprising at least one of the foregoing effective to form a latex sealing or adhesive composition can be determined by one of ordinary skill in the art, and can be, for example, about 5 to about 80 wt. % of the polymer binder solids, based on the dry weight of the caulking composition, and about 0.1 to about 30%, specifically between about 0.1 and 10% and more specifically between about 0.1 and 5% of the 1,4-pentanediol or the ketal alcohols (1), such as (1a), (1b), or a combination comprising at least one of the foregoing, based on the dry weight of the polymer binder.

In another embodiment, a latex ink composition comprises a latex polymer binder, water, 1,4-pentanediol or the ketal alcohols (1), such as (1a), (1b), or a combination comprising at least one of the foregoing a pigment and optionally an ink additive, for example a wax. The polymer binder of the latex can be selected from a wide variety of polymers as known in the art of latex ink compositions, for example those described above for latex paint compositions. Additives include waxes, dyes, antifoam agents, antifreeze agents, surfactants and plasticizers. The amounts of the latex polymer binder and the 1,4-pentanediol or the ketal alcohols (1), such as (1a), (1b), or a combination comprising at least one of the foregoing effective to form a latex ink composition can be determined by one of ordinary skill in the art, and can be, for example, about 5 to about 80 wt. % of the polymer binder solids, based on the dry weight of the caulking composition, and about 0.1 to about 30% of the 1,4-pentanediol or the ketal alcohols (1), such as (1a), (1b), or a combination comprising at least one of the foregoing, based on the dry weight of the polymer binder.

A method of preparing a latex coating composition, for example a paint composition, comprises combining the aqueous emulsion of the latex polymer binder, the 1,4-pentanediol or the ketal alcohols (1), such as (1a), (1b), or a combination comprising at least one of the foregoing and any optional additives, for example a pigment to form a latex coating composition. The ketal alcohols and additives can be added in any suitable order to the polymer latex, the additives, or combinations thereof, to provide these additives in the aqueous coating composition. In the case of latex paint compositions, the aqueous coating composition has a pH from 7 to 10.

A method of use, that is, coating a substrate with the latex coating composition is also described. The substrate can be a wide variety of materials such as paper, wood, concrete, metal, glass, ceramics, plastics, plaster, roofing substrates such as asphaltic coatings, roofing felts, foamed polyurethane insulation, polymer roof membranes, and masonry substrates such as brick, cinderblock, and cementitious layers, including exterior building cladding systems such as EIFS (Exterior Insulating Finishing Systems). The substrates include previously painted, primed, undercoated, worn, or weathered substrates. The method comprises contacting a surface of the substrate with the latex coating composition to form a coating; and drying the coating to harden the coating. The term "coating" as used herein broadly encompasses a thin film (e.g., a layer having a thickness of 0.02 to 5 millimeters, as would be formed using a paint or ink formulation) and thicker layers, for example thick bead of material (e.g., a bead having a thickness of 5 to 50 millimeters or more, as would be formed using a caulking material). The term "coating" further includes continuous as well as patterned layers. The aqueous coating composition can be applied to the materials by a variety of techniques well known in the art such as, for example, curtain coating, sponge, brush, roller, mop, air-assisted or airless spray, electrostatic spray, caulking gun, ink jet, and the like. Hardening occurs through solvent loss, either by evaporation under atmospheric conditions at room temperature or with heat to aid drying rate.

According to another embodiment, a substrate coated with a dried latex coating is provided, wherein the dried latex coating comprises the latex polymer binder in the form of a dried coating. Trace amounts of 1,4-pentanediol or the ketal alcohols (1), such as (1a), (1b), or a combination comprising at least one of the foregoing may be present. The dried latex coating is disposed on a surface of the substrate, in the form of a layer that can partially or completely cover the surface. The coating can be disposed directly on the surface, or one or more intermediate layers (e.g., a primer) can be present between the coating and the surface of the substrate. In a further embodiment, the dried latex coating can be a dried latex paint coating that comprises the latex polymer binder in the form of a layer. The dried latex paint coating further contains one or more additional additives as discussed above, for example a pigment. The dried latex coating or dried latex paint coating can be substantially free of one or more of water, another coalescing agent, or other organic solvent. In a specific embodiment, no residual 1,4-pentanediol or the ketal alcohols (1), such as (1a), (1b), or a combination comprising at least one of the foregoing is present in the dried layer; in another embodiment any residual amount of 1,4-pentanediol or the ketal alcohols (1), such as (1a), (1b), or a combination comprising at least one of the foregoing is present in the dried layer in an amount that does not adversely affect the properties of the coating, for example the hardness of the coating.

The latex coating compositions exhibit comparable or improved coalescence compared to otherwise similar compositions that do not have the 1,4-pentanediol or the ketal alcohols (1), such as (1a), (1b), or a combination comprising at least one of the foregoing.

Furthermore, the latex paint compositions can have very good overall performance, in particular one or more of Viscosity, Dry Times, Sag Resistance, Flow and Leveling, Hardness, Specular Gloss, Dry Film Adhesion, Impact Flexibility, Dilute Alkali Resistance, Water Resistance, Stain Resistance, Solvent Resistance, Hydraulic Fluid Resistance, Weatherability, and good heat storage stability.

In a specific embodiment, a latex paint composition comprises a styrene-acrylic emulsion, water, pigment, and 1,4-pentanediol or the ketal alcohols (1), such as (1a), (1b), or a combination comprising at least one of the foregoing. Styrene-acrylic emulsions are particularly suited for light industrial interior/exterior enamels as a primer.

In another specific embodiment, a latex paint composition comprises a 100% acrylic emulsion, water, pigment, and 1,4-pentanediol or the ketal alcohols (1), such as (1a), (1b), or a combination comprising at least one of the foregoing. Acrylic emulsions of this type are particularly suited for wall paints and interior/exterior architectural trim paints.

In another specific embodiment, a latex paint composition comprises a polyvinyl acetate emulsion, water, pigment, and 1,4-pentanediol or the ketal alcohols (1), such as (1a), (1b), or a combination comprising at least one of the foregoing. Polyvinyl acetate emulsions of this type are especially suited for use as interior wall paints. On primed drywall.

Water Reducible Coating Compositions

In another embodiment, the 1,4-pentanediol or the ketal alcohols (1), such as (1a), (1b), or a combination comprising at least one of the foregoing are useful in water reducible coating compositions, in particular water reducible paint compositions.

Thus, in an embodiment, a water-reducible coating composition comprises a water-reducible polymer binder, water, and 1,4-pentanediol or a ketal alcohol (1), specifically (1a) or (1b), or a combination comprising at least one of the foregoing.

The polymer binder can be selected from a wide variety of polymers known in the art of water-reducible coating compositions, specifically water-reducible paint compositions, and include, for example, acrylics that are produced using traditional polymerization techniques in a water-miscible organic solvent, polyesters, polyurethanes, alkyds, silicone-modified alkyds, epoxies, epoxy esters, and alkyds. In specific embodiment, the binder is a polyurethane, for example an aliphatic polyurethane, an alkyd, an acrylic, or combinations or hybrids thereof.

The various types of polymer binders are often made water-reducible by neutralizing residual carboxylic acid groups attached to the polymer backbone with a base, for example an organic amine, ammonium hydroxide, or other base. Exemplary acrylic binders or alkyds can have acid numbers of about 20 to about 100, for example.

The polymer binder can be thermosetting, in which case any curing agent utilized for each polymer binder will depend on the nature of the particular polymer and its curing mechanism. Thus, for the polyester and alkyd polymers having hydroxyl, carboxyl or amide functionality or any combination of such functionalities, cross-linking or curing can be effected by means of urea formaldehyde, melamine formaldehyde and methoxylated, ethoxylated or butoxylated forms thereof. Blocked isocyanate crosslinking agents are also known in the art. Catalysts can also be used to promote the curing reaction, such as peroxides. In addition to catalysts, promoters and activators for promoting the curing reaction can be used.

Some polymer binders, e.g., curable polyurethane binders, include two components: an aqueous component including an active hydrogen-containing component (i.e., a polyol or amino-functional compound) in one part and an aqueous polyisocyanate in another part. The polyol can be a soluble or water-dispersible polyol, optionally having a carboxyl group, or a hydroxy- and/or amino-functional oligourethane, and the polyisocyanate can be modified with polyoxyalkylene ether alcohol to be water-soluble or water dispersible.

Epoxy binders include derivatives of diglycidyl ether/bisphenol compounds such as bisphenol A (DGEBA), i.e., derivatives of polyether diepoxides that are obtained from the polymeric adduction of bisphenols with the diglycidyl ether of the bisphenol. The epoxies can be rendered water-soluble by reacting them with phosphoric acid and then neutralizing the resulting, acidic, ester, and glycol-comprising reaction products with a base. If the base is a fugitive base, such as ammonia or a volatile amine, the water-thinned, neutralized polymer can be converted to a water-insensitive, high performance thermoset polymer binder by evaporating the water, heating to disrupt the ammonium salt groups and drive off the ammonia (or amine), and curing. Conventional curing agents capable of reacting with acidic and/or alcoholic hydroxyl groups may be incorporated with the uncured polymer. Epoxy binders can also be made with a surfactant to aid in dispersion. In some cases, the surfactant can have reactive groups so that the surfactant is chemically incorporated into the polymer system.

The water-reducible polymer binder can be present in water completely dissolved, i.e., in the form of a solution, in the form of aggregates, or an aqueous dispersion, and can include about 5 to about 85 weight percent (wt. %) solids, specifically about 10 to about 75 wt. % solids (i.e., the weight percentage of the polymer binder based on the total weight of the water-reducible coating composition). As used herein, "solids" refers to the 100% binder in whatever form, such as a solid or liquid. The polymer binder can be present in a wide variety of particle sizes, for example a mean polymer binder particle size from about 10 to about 1,000 nanometers (nm), specifically about 50 to about 800 nm. The particle size distribution can be mono-modal or multimodal, for example bimodal.

The 1,4-pentanediol or the ketal alcohol (1), specifically (1a) or (1b), or a combination comprising at least one of the foregoing is present in the water-reducible coating composition in an amount effective for its purpose, i.e., coalescence of a film, solubilization, and the like. Such amounts can be determined by one of ordinary skill in the art, and can be for example, from about 0.1 to about 30 wt. %, or 0.5 to about 30 wt. %, specifically about 1 to about 20 wt. % or about 1 to about 10 wt. %, each based on the total weight of the water-reducible coating compositions. The balance of the water-reducible coating compositions is water, polymer binder, and other optional additives, including cosolvents known in the art.

A method of preparing a water-reducible coating composition comprises combining the polymer binder, the 1,4-pentanediol or the ketal alcohols (1), specifically (1a) and/or (1b), aqueous phase (i.e., water and any cosolvents if present), and any additives, if present, to form a water-reducible coating composition. The components can be added in any suitable order to provide the water-reducible coating composition.

In a specific embodiment, the 1,4-pentanediol or the ketal alcohols (1), specifically (1a) or (1b), or a combination comprising at least one of the foregoing are used in water-reducible paint compositions, stain composition, or clear-coat compositions, and can reduce or replace other organic solvents in the water-reducible compositions.

Thus, in an embodiment, a water-reducible paint, stain, or clear-coat composition comprises a water-reducible polymer binder composition, water, optionally a pigment, and 1,4-pentanediol or the ketal alcohols (1), specifically (1a) or (1b), or a combination comprising at least one of the foregoing. A wide variety of water-reducible polymer binders can be used, including those described above. When the polymer binder is thermosetting, the binder compositions comprise the uncured polymer and one or more of a curing agent, catalyst, initiator, or promoter, if used.

A pigment can be present in the water-reducible paint or stain composition. The pigment can be same as described herein in the context of latex coating compositions.

A dye can be present in the water-reducible paint or stain composition, in addition to or instead of a pigment. The term "dye" as used herein includes organic compounds generally soluble in the compositions, and that impart color to the compositions.

The water-reducible paint, stain, or clear-coat composition can contain additional additives, as known in the art, to modify the characteristics of the water-reducible composition, provided that the additives do not significantly adversely affect the desired properties of the paint, stain, or clear-coat, for example, viscosity, drying time, or other characteristic. These additives can include a plasticizer, drying retarder, dispersant, surfactant or wetting agent, rheology modifier, defoamer, thickener, biocide, mildewcide, colorant, wax, perfume, pH adjuster, or cosolvent. The additives are present in the amount ordinarily used in water-reducible paint, stain, or clear-coat compositions. In an embodiment, the water-reducible paint, stain, or clear-coat composition consists essentially of a water-reducible polymer binder, water, an optional pigment, an optional dye, and 1,4-pentanediol or the ketal alcohols (1), specifically (1a) and/or (1b), or a combination comprising at least one of the foregoing. As used herein, the phrase "consists essentially of" encompasses the water-reducible polymer binder, water, optional pigment, and 1,4-pentanediol or the ketal alcohols (1), and optionally one or more of the additives defined herein, but excludes any additive that significantly adversely affects the desired properties of the water-reducible composition or the dried coating derived therefrom.

The water-reducible polymer binder can be present in the water-reducible paint composition in an amount from about 2 to about 60 wt. %, and more specifically about 4 to about 40 wt. % of the water-reducible paint composition, based on the dry weight of the polymer water-reducible binder.

The water-reducible polymer binder can be present in the water-reducible stain composition in an amount from about 0.1 to about 50 wt. %, and more specifically about 0.5 30 wt. % of the water-reducible stain composition, based on the dry weight of the polymer water-reducible binder.

When present, the pigment or dye can be used in the water-reducible stain composition in an amount from about 0.1 to about 40 wt. %, specifically about 0.5 to about 30 wt. % of the total solids in the water-reducible stain composition.

When present, the dye can be used in the water-reducible paint or stain composition in an amount from about 0.001 to about 10 wt. %, specifically about 0.005 to about 5 wt. % of the total solids in the water-reducible paint or stain composition.

The 1,4-pentanediol or the ketal alcohols (1), specifically 1(a) and/or (1b), more specifically 1(b), can be present in an amount from about 0.1 to about 30 wt. %, specifically about 1 to about 10 wt. %, more specifically about 1 to about 8 wt. %, and still more specifically about 1 to about 7 wt. %, based on the dry weight of the polymer binder.

The water-reducible paint composition can include about 5 to about 85 wt. % and more specifically about 35 to about 80 wt. % water, i.e., the total solids content of the water-reducible paint composition can be about 15 to about 95 wt. %, more specifically, about 20 to about 65 wt. % of the total composition. The compositions can be formulated such that the hardened (dried) coatings comprise at least about 2 to about 98 volume % (vol. %) polymer solids and, if present, 1,4-pentanediol or the ketal alcohols (1), specifically (1a) and/or (1b), and about 2 to about 98 vol. % of non-polymeric solids in the form of pigments or a combination of a pigment and a dye, together with other additives (if present).

The water-reducible stain composition can includes about 10 to about 95 wt. % and more specifically about 25 to about 90 wt. % water, i.e., the total solids content of the water-reducible stain composition can be about 5 to about 75 wt. %, more specifically, about 10 to about 75 wt. % of the total composition. The stain compositions are typically formulated such that the hardened (dried) coatings comprise at least about 1 vol. %, for example about 5 to about 98 vol. % polymer solids, if present, 1,4-pentanediol or the ketal alcohols (1), specifically (1a) and/or (1b), and about 0.1 to about 99 vol. % of non-polymeric solids in the form of pigments and/or dyes, and other additives (if present). A wood stain coating can penetrate the wood substrate to some degree.

The water-reducible clear-coating composition can include about 10 to about 95 wt. % and more specifically about 25 to about 90 wt. % water, i.e., the total solids content of the water-reducible clear-coating composition can be about 5 to about 75 wt. %, more specifically, about 10 to about 75 wt. % of the total composition. The compositions are typically formulated such that the hardened (dried) clear-coatings comprise at least about 1 vol. % polymer solids, for example about 1 to about 100 vol. % polymer solids, if present, 1,4-pentanediol or the ketal alcohols (1), specifically (1a) and/or (1b), and 0 to about 10 vol. % of non-polymeric solids. For example, in clear-coat compositions certain additives (e.g., calcium carbonate, talc, or silica) can be used that do not impart color, but rather serve primarily to reduce formulation cost, modify gloss levels, or the like.

In an embodiment, a method of preparing a water-reducible paint, stain, or clear-coating composition comprises combining the polymer binder, 1,4-pentanediol or the ketal alcohols (1), specifically (1a) and/or (1b), or a combination comprising at least one of the foregoing, the pigment (if used), water, and any optional additives to form a water-reducible composition. The components can be added in any suitable order to provide the water-reducible composition.

In another exemplary embodiment, a method of use, that is, coating a substrate with the water-reducible paint, stain, or clear-coat composition is described. The method comprises contacting a surface of the substrate with the water-reducible paint, stain, or clear-coat composition to form a film; and drying the film to harden the film. The water-reducible composition can at least partially impregnate the substrate after contacting. The film can further optionally be cured.

The substrate can be a wide variety of materials, including but not limited to, paper, wood, concrete, metal, glass, textiles, ceramics, plastics, plaster, roofing substrates such as asphaltic coatings, roofing felts, foamed polyurethane insulation, polymer roof membranes, and masonry substrates such as brick, cinderblock, and cementitious layers, including EIFS systems (synthetic stucco made from engineered layers of polystyrene insulation with a cement-like mud called a topcoat or basecoat, and which is applied with a trowel). The substrates include previously painted, primed, undercoated, worn, or weathered substrates.

The aqueous coating composition can be applied to the materials by a variety of techniques well known in the art such as, for example, curtain coating, brush, rollers, mops, air-assisted or airless spray, electrostatic spray, and the like. Paints and clear-coats may or may not partially penetrate, i.e., partially impregnate the substrate upon coating. In an embodiment, a water-reducible paint composition does not substantially penetrate or impregnate the substrate. In another embodiment, a water-reducible clear-coat composition does not substantially penetrate or impregnate the substrate. Stains are generally designed to partially or fully impregnate the substrate upon coating. In embodiment, the substrate is fully impregnated by the water-reducible stain composition, such that the film formed conforms to the interior of the coated substrate, and may be continuous or discontinuous.

Hardening can be by drying, for example storage under atmospheric conditions at room temperature. Drying can also include solvent wicking, for example by the substrate itself (e.g., wood or paper). Heat can be used as an aid to drying. Curing can be used to further harden the film. Curing may be carried out before drying, during drying, or after drying, or any combination thereof.

According to another embodiment, a substrate coated with a dried water-reducible coating is provided, wherein the dried water-reducible coating, substrate, or combination thereof comprises the water-reducible polymer binder in the form of a film. The film can be a paint, a stain, or a clear-coat. After drying, some amount of 1,4-pentanediol or the ketal alcohols (1) can be present in the film, in the substrate (by impregnating the substrate), or both. In an embodiment, the 1,4-pentanediol or the ketal alcohols (1) can be chemically combined with the polymer binder. For example, 1,4-pentanediol or the ketal alcohols (1), specifically (1a) and/or (1b) can be present in the coating in an amount from about 1 part per million by weight (ppm) to about 15 wt. %, specifically about 0.1 to about 15 wt. %, each based on the total weight of the dried coating. For example, where the 1,4-pentanediol or the ketal alcohols (1) performs a plasticizing function, the adduct can be present in higher amounts, for example about 0.25 to about 15 wt. %, based on the total weight of the dried coating. The dried water-reducible coating can be disposed on a surface of the substrate, in the form of a film that can partially or completely cover the surface. The coating can be disposed directly on the surface, or one or more intermediate layers (e.g., a primer) can be present between the coating and the surface of the substrate. In addition, or alternatively, as described above, the coating can be partially or fully impregnated into the substrate and conform to interior surfaces of the substrate. In any of the foregoing embodiments, it is also possible to dry the coating and/or substrate sufficiently to remove 1,4-pentanediol or the ketal alcohols (1), specifically (1a) and/or (1b) to below detectable limits in the films.

The water-reducible coating compositions exhibit comparable or improved coalescence compared to otherwise similar compositions that do not have the 1,4-pentanediol or the ketal alcohols (1), specifically (1a) and/or (1b).

Furthermore, the water-reducible paint compositions can have very good overall performance, in particular one or more of viscosity, dry times, sag resistance, flow and leveling, hardness, specular gloss, dry film adhesion, impact flexibility, dilute alkali resistance, water resistance, stain resistance, solvent resistance, hydraulic fluid resistance, weatherability, and good heat storage stability.

The following non-limiting examples further illustrate various embodiments as described herein.

EXAMPLES

Example 1

Solubility Testing—Ketal Alcohol (1a)

Two-component mixtures of compound (1a) (a compound of formula (1) wherein $R^2$ and $R^3$ are methyl, $R^6$ and $R^7$ are hydrogen, a is 3, b is 0, also referred to as "reduced LPK" or "RedLPK") were prepared by mixing the materials at various proportions at room temperature in a vial by shaking. The results are shown in Table 1.

TABLE 1

| Solute | Wt % Solute | Wt % Ketal alcohol (1a) | Observation* |
|---|---|---|---|
| glycerol | 50% | 50% | soluble |
| DI water | 90% | 10% | soluble |
| DI water | 80% | 20% | soluble |
| DI water | 75% | 25% | soluble |

TABLE 1-continued

| Solute | Wt % Solute | Wt % Ketal alcohol (1a) | Observation* |
|---|---|---|---|
| DI water | 67% | 33% | soluble |
| DI water | 50% | 50% | soluble |
| toluene | 50% | 50% | soluble |
| hexane | 50% | 50% | soluble |
| soy methyl ester | 10% | 90% | soluble |
| soy methyl ester | 33% | 66% | soluble |
| soy methyl ester | 50% | 50% | soluble |
| castor oil | 10% | 90% | soluble |
| castor oil | 33% | 66% | soluble |
| castor oil | 50% | 50% | soluble |
| corn oil | 10% | 90% | soluble |
| corn oil | 33% | 66% | cloudy/separated (insoluble) |
| corn oil | 50% | 50% | cloudy/separated (insoluble) |
| mineral oil | 10% | 90% | cloudy/separated (insoluble) |
| mineral oil | 33% | 66% | cloudy/separated (insoluble) |
| mineral oil | 50% | 50% | cloudy/separated (insoluble) |

*"soluble" means the mixture that shows no presence of the original solute and stays in solution at room temperature for 24 hours.

A comparison of solubility breadth with other common coupling solvents/hydrotropes is shown in Table 2, where amount of solute is in weight percent, with the remainder being a ketal alcohol (1a), the glycerol ketal of ethyl levulinic acid (EtLGK, the compound of formula (2) wherein $R^1$ is ethyl, $R^2$ is methyl, $R^3$ is hydroxymethylene, $R^6$ and $R^7$ are hydrogen, a=3, and b=0), propylene glycol methyl ether (PM), dipropylene glycol methyl ether (DPM), or 2-butoxyethanol as indicated in Table 2.

TABLE 2

| | | Coupling Solvent/Hydrotrope | | | | |
|---|---|---|---|---|---|---|
| Solute | % Solute | (1a) | EtLGK | PM | DPM | 2-butoxyethanol |
| glycerol | 50% | S | I | S | S | I |
| DI water | 90% | S | S | S | S | S |
| DI water | 80% | S | S | S | S | S |
| DI water | 75% | S | S | S | S | S |
| DI water | 67% | S | S | S | S | S |
| DI water | 50% | S | S | S | S | S |
| toluene | 50% | S | S | S | S | S |
| hexane | 50% | S | I | S | S | S |
| corn oil | 10% | S | I | S | S | S |
| corn oil | 33% | I | I | S | S | S |
| corn oil | 50% | I | I | S | S | S |
| mineral oil | 10% | I | I | I | I | S |
| mineral oil | 33% | I | I | I | I | S |
| mineral oil | 50% | I | I | I | I | S |

S = soluble; one phase
I = insoluble; cloudy mixture, separates into two phases

The results in Table 2 show that ketal alcohol (1a) has breadth of solubility very similar to certain glycol ethers that are often used in cleaning and personal care formulations, in particular propylene glycol methyl ether (PM) and dipropylene glycol methyl ether (DPM).

Example 2

Coupling of Water and Octanoic Acid using Ketal Alcohol (1a)

Hydrotropes were added to a two-component mixture of octanoic acid and deionized (DI) water to find the amount that produced a single phase from the two separate phases of water and octanoic acid. The results are shown in Table 3.

TABLE 3

| | Amount (grams) | | | | |
|---|---|---|---|---|---|
| DI water | 0.5 | 1.5 | 5.0 | 3.5 | 4.5 |
| Octanoic Acid | 4.5 | 3.5 | 5.0 | 1.5 | 0.5 |
| Weight Ratio* | 10:90 | 30:70 | 50:50 | 70:30 | 90:10 |
| Hydrotropes | | | | | |
| DPM | 2.14 | 4.52 | 10.34 | 4.66 | 3.7 |
| EtLGK | 3.11 | 7.2 | 22.68 | 9.79 | 6.84 |
| Ketal alcohol (1a) | 2.27 | 5.63 | 11.81 | 6.07 | 4.33 |
| Sodium xylene-sulfonate (SXS) (40%) | 2.32 | 3.23 | 7.4 | 3.55 | 3.33 |
| 2-butoxyethanol | 2.47 | 5.39 | 6.74 | 7.9 | 5.43 |
| PM | 1.09 | 3.12 | 3.62 | 3.68 | 3.44 |
| ethanol | 1.12 | 2.95 | 3.14 | 2.97 | 2.87 |

*Water:Octanoic Acid

The percent hydrotrope required to compatibilize phases (and the resulting percent octanoic acid) were calculated and the results are shown in Table 4 as well as FIG. 1.

TABLE 4

| | Ratio of water:octanoic acid | | | | |
|---|---|---|---|---|---|
| Hydrotrope | 10:90 | 30:70 | 50:50 | 70:30 | 90:10 |
| | Wt % Octanoic Acid | | | | |
| DPM | 63% | 37% | 25% | 16% | 6% |
| EtLGK | 55% | 29% | 15% | 10% | 4% |
| Red LPK | 62% | 33% | 23% | 14% | 5% |
| SXS | 61% | 43% | 29% | 18% | 6% |
| 2-butoxyethanol | 60% | 34% | 21% | 12% | 5% |
| PM | 74% | 43% | 29% | 17% | 6% |
| ethanol | 74% | 44% | 31% | 19% | 6% |
| | Wt % Hydrotrope | | | | |
| DPM | 30% | 47% | 51% | 48% | 43% |
| EtLGK | 38% | 59% | 69% | 66% | 58% |
| Ketal alcohol (1a) | 31% | 53% | 54% | 55% | 46% |
| SXS | 13% | 16% | 17% | 17% | 16% |
| 2-butoxyethanol | 33% | 52% | 57% | 61% | 52% |
| Dowanol PM | 18% | 38% | 42% | 42% | 41% |
| ethanol | 18% | 37% | 39% | 37% | 36% |

Example 3

Coupling of Water and Soy Methyl Ester using Ketal Alcohol (1a)

Figure 2:
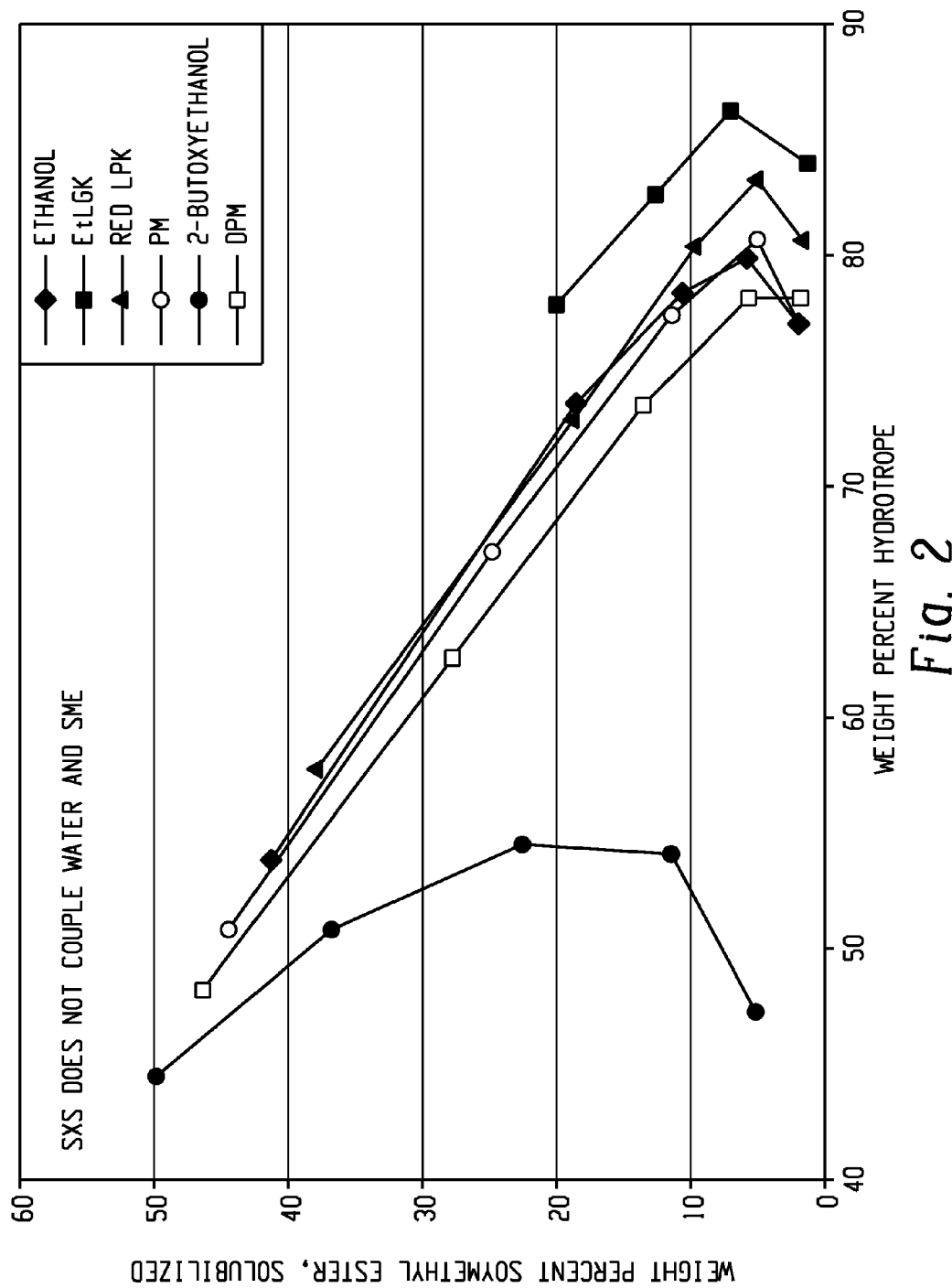
FIG. 2 illustrates the effects of various hydrotropes on the solubility of soy methyl esters in water.

Hydrotropes were added to a two-component mixture of soy methyl ester and DI water to find the amount that produced a single phase from the two separate phases of water and soy methyl ester. The percent hydrotrope required to compatibilize the phases was calculated. The results are shown in Table 5 as well as FIG. 2.

TABLE 5

| | Ratio of water:soy methyl esters | | | | |
|---|---|---|---|---|---|
| Hydrotrope | 10:90 | 30:70 | 50:50 | 70:30 | 90:10 |
| | Wt % Soy Methyl Esters | | | | |
| Ethanol | 41% | 18% | 11% | 6% | 2% |
| EtLGK | 20% | 7% | 4% | 4% | 2% |
| Ketal alcohol (1a) | 38% | 19% | 10% | 5% | 2% |
| PM | 44% | 25% | 11% | 5% | 2% |
| 2-Butoxyethanol | 50% | 37% | 23% | 11% | 5% |
| DPM | 47% | 28% | 13% | 5% | 2% |
| Sodium xylenesulfonate | nd* | nd* | nd* | nd* | nd* |

TABLE 5-continued

|  | Ratio of water:soy methyl esters | | | | |
|---|---|---|---|---|---|
| Hydrotrope | 10:90 | 30:70 | 50:50 | 70:30 | 90:10 |
|  | Wt % Hydrotrope | | | | |
| ethanol | 54% | 74% | 78% | 80% | 77% |
| EtLGK | 78% | 83% | 86% | 86% | 84% |
| Ketal alcohol (1a) | 58% | 73% | 81% | 83% | 81% |
| PM | 51% | 67% | 77% | 81% | 77% |
| 2-Butoxyethanol | 44% | 51% | 55% | 54% | 47% |
| DPM | 48% | 63% | 74% | 78% | 78% |
| Sodium xylenesulfonate | nd* | nd* | nd* | nd* | nd* |

*The sodium xylenesulfonate did not compatibilize at any measured level (up to >95%).

Example 4

Coupling of Water and Castor Oil using Ketal Alcohol (1a)

Hydrotropes were added to a two-component mixture of castor oil and DI water to find the amount that produced a single phase from the two separate phases of water and soy methyl ester. The percent hydrotrope required to compatibilize phases was calculated. The results are shown in Table 6.

TABLE 6

|  | Ratio of water to castor oil | | | | |
|---|---|---|---|---|---|
| Hydrotrope | 10:90 | 30:70 | 50:50 | 70:30 | 90:10 |
|  | Wt % Castor oil | | | | |
| Ethanol | 40% | 22% | 10% | 5% | 2% |
| EtLGK | 35% | 17% | 9% | 4% | 1% |
| Ketal alcohol (1a) | 32% | 21% | 11% | 5% | 2% |
| PM | 36% | 26% | 12% | 5% | 2% |
| 2-butoxyethanol | 50% | 34% | 20% | 9% | 4% |
| DPM | 40% | 26% | 13% | 5% | 2% |
| Sodium xylenesulfonate | nd* | nd* | nd* | nd* | nd* |
|  | Wt % Hydrotrope | | | | |
| Ethanol | 55% | 69% | 79% | 82% | 84% |
| EtLGK | 61% | 76% | 82% | 86% | 85% |
| Ketal alcohol (1a) | 64% | 71% | 79% | 82% | 84% |
| PM | 61% | 65% | 76% | 81% | 83% |
| 2-butoxyethanol | 44% | 55% | 61% | 64% | 61% |
| DPM | 56% | 65% | 74% | 79% | 81% |
| Sodium xylenesulfonate | nd* | nd* | nd* | nd* | nd* |

*The sodium xylenesulfonate did not compatibilize at any measured level (up to >95%).

Example 5

Hard Surface Cleaning Formulation—pH Testing

Formulations were prepared by combining ingredients and mixing until homogeneous. Next, pH measurements were taken over 7 days. The results are shown in Table 7.

TABLE 7

|  | Control | A | B | C |
|---|---|---|---|---|
| Item (g) | | | | |
| DI water | 84 | 79 | 79 | 79 |
| BIO-SOFT ® D-40* | 5.3 | 5.3 | 5.3 | 5.3 |

TABLE 7-continued

|  | Control | A | B | C |
|---|---|---|---|---|
| Tetrasodium EDTA, 38% | 7.7 | 7.7 | 7.7 | 7.7 |
| 2-Butoxyethanol | — | 5 | — | — |
| Ketal alcohol (1a) | — | — | 5 | — |
| EtLGK | — | — | — | 5 |
| NINOL ® 11-CM* | 3 | 3 | 3 | 3 |
| Total | 100 | 100 | 100 | 100 |
| pH | | | | |
| initial | 10.21 | 10.18 | 10.17 | 10.1 |
| Day 1 | 10.17 | 10.15 | 10.17 | 9.62 |
| Day 2 | 10.15 | 10.13 | 10.15 | 9.41 |
| Day 4 | 10.21 | 10.14 | 10.17 | 9.19 |
| Day 7 | 10.24 | 10.16 | 10.18 | 9.04 |

*available from Stepan Company

The results show that the formulation containing the ketal alcohol (1) maintained the same pH as the formulation containing 2-butoxyethanol and the control formulation, whereas the formulation containing EtLGK underwent significant pH drift downward.

Example 6

Hard Surface Cleaning Formulation—Freeze-Thaw Testing 1

Formulations as in Example 5 were prepared by combining ingredients and mixing until homogeneous. Freeze-thaw testing was performed over 3 cycles. Each cycle was putting the formulations into a 0° C. freezer for greater than 12 hours, then taking them out and allowing the samples to thaw to room temperature and then making the visual observation.

TABLE 8

| Cycle | Control | 2-Butoxyethanol | Ketal alcohol (1a) | EtLGK |
|---|---|---|---|---|
| 1 | separation | separation; easily remixed w/o re-separation | stable; no separation | stable; no separation |
| 2 | separation | separation; easily remixed w/o re-separation | gradient; easily remixed w/o re-separation | gradient; easily remixed w/o re-separation |
| 3 | separation | two phases; clear; easily remixed w/o re-separation | gradient; easily remixed w/o re-separation | gradient; easily remixed w/o re-separation |

As shown in Table 8, the formulation containing ketal alcohol (1a) performed similarly to or better than the 2-butoxyethanol.

Example 7

Hard Surface Cleaning Formulation—Heat Cloud Point Testing

Formulations as in Example 5 were prepared by combining ingredients and mixing until homogeneous. Cloud point testing was performed by heating a vial containing each formulation while mixing until the temperature was reached in which the solution was no longer clear and appeared cloudy. The results are shown in Table 9.

TABLE 9

|  | Control | Butyl Cellosolve | Ketal alcohol (1a) | EtLGK |
|---|---|---|---|---|
| Cloud point | cloudy at room temperature | 44° C. | >100° C. | >100° C. |

The formulations containing ketal alcohol (1a) and EtLGK had similar cloud points and showed no signs of cloudiness. The 2-butoxyethanol had a cloud point of 44° C. The control was cloudy at room temperature.

Example 8

Hard Surface Cleaning Formulation—Performance Testing

Formulations in Table 10 were prepared by combining ingredients and mixing until homogeneous. Test panels were made by cutting 4.5×6.5 inch panels from hardboard. The textured side of the boards was then painted with two coats of 100% acrylic white flat paint. The test grease, composed of 33% lard, 33% vegetable oil, 33% vegetable shortening, and 1% carbon black pigment (heated and stirred), was put onto the white painted masonite boards using a 1 mil drawn down bar.

In each head-to-head test, two soiled panels were loaded onto the Elcometer 1720 washability tester with sponge attachments. Two sponges were soaked with 15 g of different cleaning formulations and put into the testing carriage. The comparative test was run at 20 cycles/min for 5 cycles. The two completed panels were wrapped in clear plastic (SARAN) wrap and their color was measured in three places on the sponge track using a ColorQuest XE colorimeter in reflectance mode. The machine was standardized to the pure white tile and pure black tile and the L measurements were recorded (Table 11).

TABLE 10

| Item (g) | 32 (Control) | 32A | 32B | 32C |
|---|---|---|---|---|
| DI water | 84 | 79 | 79 | 79 |
| BIO-SOFT D-40 | 5.3 | 5.3 | 5.3 | 5.3 |
| Tetrasodium EDTA, 38% | 7.7 | 7.7 | 7.7 | 7.7 |
| 2-butoxyethanol | — | 5 | — | — |
| Ketal alcohol (1a) | — | — | 5 | — |
| EtLGK | — | — | — | 5 |
| NINOL 11-CM | 3 | 3 | 3 | 3 |
| Total | 100 | 100 | 100 | 100 |

TABLE 11

| Panel label | | Cycles | Average L value |
|---|---|---|---|
| 35A | 32A | 5 | 73.44 |
| | Control | 5 | 58.83 |
| 35B | 32B | 6 | 72.11 |
| | Control | 6 | 67.14 |
| 35C | 32Control | 5 | 58.81 |
| | 32A | 5 | 74.24 |
| 35D | 32Control | 5 | 53.82 |
| | 32B | 5 | 74.09 |
| 35E | 32Control | 5 | 55.42 |
| | 32C | 5 | 62.82 |
| 35F | 32A | 5 | 59.55 |
| | 32B | 5 | 66.92 |
| 35G | 32A | 5 | 71.56 |
| | 32C | 5 | 68.66 |

TABLE 11-continued

| Panel label | | Cycles | Average L value |
|---|---|---|---|
| 35H | 32B | 5 | 60.57 |
| | 32C | 5 | 60.02 |

The averaged results in Table 12 show that the formulas containing solvent produce higher L values than the control, indicating better cleaning performance for the formulations with solvents included. Statistically, the solvents performed equivalently.

TABLE 12

| Formulation | Average L value | Std Dev |
|---|---|---|
| Control | 56.7 | 2.2 |
| 32A | 69.7 | 5.9 |
| 32B | 67.2 | 5.5 |
| 32C | 63.8 | 3.6 |

Example 9

Cleaning Formulations

Liquid laundry detergent and hand dish wash formulations can be manufactured as follows, wherein amounts shown are weight percent.

| Liquid Laundry Detergent | Amount |
|---|---|
| Linear alkylbenzene sulfonate | 18% |
| C8-10 Propyl Dimethyl amine | 2.0% |
| C12-14 Alkyl Ethoxylate | 12% |
| C12-18 Fatty Acid | 11% |
| Citric acid | 5% |
| Diethylenetriaminepentaacetic acid | 1% |
| Monoethanol amine | 11% |
| NaOH | 1% |
| Propane diol | 11.0% |
| Ketal alcohol (1a) | 3.5% |
| Enzymes (Mix) | 0.9% |
| Terephthalate Polymer | 0.5% |
| Boric acid | 2.4% |
| Suds Suppressor | 1.0% |
| Water | Balance |

| Liquid Hand Dish Wash Detergent | Amount |
|---|---|
| C12-13 Alkylethoxy (E3.5) Carboxylate | 22% |
| C12-13 Alcoholehtoxylate (E3.5) | 1.3% |
| C12-13 Alkylsulfate | 6% |
| C12-14 Amidopropyl Dimethyl Betaine | 3% |
| C14 Amine Oxide | 3% |
| $MgCl_2$ | 0.6% |
| Methyldiethanol amine | 10% |
| Ketal alcohol (1a) | 9% |
| Water | Balance |

Example 10

Hair Dye Active Solubility Testing using Ketal Alcohol (1a)

Two component mixtures using ketal alcohol (1a) and the actives shown in Table 13 were prepared by mixing the components at various proportions in a vial at room temperature and then heating in a lab oven at 80° C. for 10 minutes and then shaking. The results are shown in Table 13. Soluble is considered to be a mixture that shows no presence of the original solute and stays in solution at room temperature for 24 hours.

TABLE 13

| Active | Weight Percentage Active | Ketal Alcohol (1a) Solubility | Observation |
|---|---|---|---|
| p-phenylene diamine | 10% | insoluble | Undissolved particles |
| p-phenylene diamine | 5% | soluble | Dark brown liquid |
| p-phenylene diamine | 1% | soluble | orange/80° C. and agitation |
| p-toluenediamine sulfate | 10, 5, 2.5, 1, 0.5, 0.1% | 0.1% not soluble | 80° C. and agitation |
| resorcinol | 10% | 10% soluble | 80° C. and agitation |
| m-aminophenol | 10, 5% | 5% soluble | 80° C. and agitation |

Comparative formulations using EtLGK and ketal alcohol (1a) are shown below in Tables 14 and 15.

TABLE 14

| Active | Weight Percentage Active | EtLGK Solubility | Observation |
|---|---|---|---|
| p-phenylene diamine | 5% | soluble | Dark brown liquid |
| p-toluenediamine sulfate | 0.1% | 0.1% not soluble | 80° C. and agitation |
| resorcinol | 10% | 10% soluble | 80° C. and agitation |
| m-aminophenol | 5% | 5% soluble | 80° C. and agitation |

TABLE 15

| Active | Weight Percentage Active | Ketal alcohol (1a) Solubility | Observation |
|---|---|---|---|
| p-phenylene diamine | 1% | insoluble | Precipitation formed |
| p-toluenediamine sulfate | 0.1% | 0.1% not soluble | Precipitation formed |
| resorcinol | 10% | 10% soluble | 80° C. and agitation |
| m-aminophenol | 5% | 5% soluble | 80° C. and agitation |

Example 11

Fragrance Formulations containing Ketal Alcohol (1a)

Fragrance oils were mixed with the ketal alcohol (1a) in a 50/50 weight ratio in a vial at room temperature and then shaken by hand. The mixtures were initially homogeneous solutions, and were still one single phase 24 hours later as shown below in Table 16.

TABLE 16

| Item | Percentage Active | Ketal Alcohol (1a) Solubility | Observation |
|---|---|---|---|
| Basil | 50% | Soluble | turned clear |
| Birch Sweet | 50% | Soluble | turned clear |
| Cedarwood | 50% | Soluble | turned clear |
| Coriander Seed | 50% | Soluble | turned clear |
| *Geranium* | 50% | Soluble | turned clear |
| Grapefruit | 50% | Soluble | turned clear |
| Lavender | 50% | Soluble | turned clear |
| Lemon | 50% | Soluble | turned clear |
| Myrrh | 50% | Soluble | turned clear |
| Patchouli | 50% | Soluble | turned clear |
| Pine needle | 50% | Soluble | turned clear |
| vetiver | 50% | Soluble | turned clear |
| ylang ylang | 50% | Soluble | turned clear |

Example 12

Perfume Formulation

A perfume formulation having components as shown in Table 17 was made at room temperature. The resulting formulation was a clear mixture of all components.

TABLE 17

|  | g |
|---|---|
| Basil | .515 |
| Birch Sweet | .56 |
| Cedarwood | .25 |
| Coriander Seed | .55 |
| *Geranium* | .535 |
| Grapefruit | .52 |
| Lavender | .505 |
| Lemon | .53 |
| Myrrh | .59 |
| Patchouli | .535 |
| Pine needle | .505 |
| vetiver | .515 |
| ylang ylang | .52 |
| Ketal Alcohol (1a) | 6.63 |
| Sub-Total | 13.26 |
| DI Water | 1.57 |
| Ethanol (95%) | 1.22 |
| Total | 16.05 |

Example 13

Vanillin Composition

Vanillin was dissolved into the ketal alcohol (1a) at room temperature using 75% ketal alcohol (1a) to 25% vanillin by weight. The resulting mixture was a homogeneous clear liquid with no signs of precipitate.

Example 14

Candle Making

The vanillin/Ketal Alcohol (1a) mixture from Example 13 was used to prepare a candle formulation as shown in Table 18. The candle was prepared by mixing the waxes in an 80° C. water bath until the mixture was liquid. The mixture was allowed to cool to 65° C. Then the ketal/fragrance mixture was added and mixed in by hand. Then the wick was inserted and the completed candle was allowed to cool to room temperature. A taper candle was made by repeatedly dipping a wick into the molten wax.

TABLE 18

| Component | g |
|---|---|
| Beeswax | 40.00 |
| Pariffin | 40.00 |
| Ketal alcohol (1a)/vanillin (75/25) | 16.00 |
| Total | 96.0 |

Example 15

Surfactants

This example was conducted to demonstrate that fabric softener liquid concentrates containing ketal alcohol (1) are pourable. Ethanol and isopropanol were used as cosolvents. In order to manufacture the fabric softener formulations shown in Table 19, a surfactant, ketal alcohol (1a), ethanol, isopropanol and water were weighed into vials in the amounts shown in the Table 19. The vials were mixed with a rotational mixer for 5 minutes and placed in a 65° C. oven for 10 minutes. The mixtures were removed from the oven and allowed to cool to room temperature on a bench-top. Observations about visual appearance at room temperature were recorded within 1 hour of cooling.

TABLE 19

| | Solute/Resin | Solute % | ketal % | Iso-propanol % | Ethanol % | DI water % | post cooling @ 25° C. observation | CaCl2 (15%) g | Post cooling/mixing @ 25° C. Observation |
|---|---|---|---|---|---|---|---|---|---|
| A | AROSURF TA 101 | 25 | 75 | — | — | — | white solid | 0.5 | white solid |
| B | AROSURF TA 101 | 25 | 60 | 15 | — | — | thin slurry-particles | 0.5 | thick slurry |
| C | AROSURF TA 101 | 25 | 25 | — | — | 50 | white solid | 0.5 | white solid |
| D | ADOGEN 442 | 25 | 25 | — | — | 50 | white solid | 0.5 | separated |
| E | REWOQUAT WE 28 US | 25 | 12.5 | 12.5 | — | 50 | thick gel | 0.1 | pourable, cloudy |
| F | AROSURF TA 101 | 25 | 12.5 | 12.5 | — | 50 | white solid | 0.5 | separated |
| G | REWOQUAT WE 28 US | 25 | 12.5 | — | 12.5 | 50 | pourable, cloudy | 0.1 | pourable, cloudy |
| H | AROSURF TA 101 | 25 | 12.5 | — | 12.5 | 50 | white solid | 0.5 | pearlescent white solid |
| I | BIOSOFT D-40 | 25 | 75 | — | — | — | separation/cloudy | 0.5 | pourable, cloudy thin solution |
| J | BIOSOFT D-40 | 25 | 60 | 15 | — | — | separation/cloudy | 0.5 | pourable, cloudy thin solution |
| K | BIOSOFT D-40 | 25 | 25 | — | — | 50 | clear | — | pourable, clear |
| L | BIOSOFT D-40 | 25 | 12.5 | 12.5 | — | 50 | clear | — | pourable, clear |
| M | BIOSOFT D-40 | 25 | 12.5 | — | 12.5 | 50 | clear | — | pourable, clear |

Ketal in Table 19 refers to ketal alcohol (1a).

Example 16

Three component mixtures of ketal alcohol (1a), deionized water, and an active (either avobenzone, oxybenzone, or salicylic acid) were prepared by mixing the components at various proportions at room temperature in a vial and shaking by hand. Likewise, three component mixtures of ketal alcohol (1a), ethanol, and one active selected from avobenzone, oxybenzone, and salicylic acid were prepared by mixing the components. The observed results are shown in Tables 20 and 21.

TABLE 20

| Example | Active | Wt. % active | Wt. % ketal | Wt. % DI water | Observations |
|---|---|---|---|---|---|
| A | Avobenzone | 10% | 90% | 0% | Clear |
| B | Avobenzone | 8.1% | 72.9% | 19.0% | Cloudy |
| C | Oxybenzone | 40% | 60% | 0% | Clear |
| D | Oxybenzone | 36.6% | 54.9% | 8.5% | Cloudy, solid |
| E | Salicylic Acid | 20% | 80% | 0% | Clear |
| F | Salicylic Acid | 8.4% | 37.9% | 53.7% | Cloudy |

Ketal in Table 20 refers to ketal alcohol (1a).

Ketal in Table 20 refers to ketal alcohol (1a).

TABLE 21

| Example | Active | Wt. % active | Wt. % ketal | Wt. % ethanol | |
|---|---|---|---|---|---|
| A | Avobenzone | 10% | 90% | 0% | Clear |
| B | Avobenzone | 2.4% | 21.8% | 75.8% | Clear |
| C | Oxybenzone | 40% | 60% | 0% | clear |
| D | Oxybenzone | 38.9% | 58.4% | 2.7% | Cloudy, solid |
| E | Salicylic Acid | 20% | 80% | 0% | clear |

TABLE 21-continued

| Example | Active | Wt. % active | Wt. % ketal | Wt. % ethanol | |
|---|---|---|---|---|---|
| F | Salicylic Acid | 4.8% | 21.7% | 73.5% | Clear |

Ketal in Table 21 refers to ketal alcohol (1a).

Example 17

Ketal Alcohol (1a) Pigment Dispersions

Ketal alcohol (1a) can be used to disperse pigments and to carry pigments into formulations such as paint formulations, color cosmetics (such as lipsticks, foundations, and the like), and other resin systems. Pigment dispersions can be performed using a cowles blade on an overhead mixer. Various pigments, such as Dupont Ti-pure R960 Titanium Dioxide, BASF Heliogen L6905F blue, Sid Richardson SR730 Carbon Black or Iron Oxide Red HR-1203 from Hoover, are dispersed using the cowles blade for various pigments. In addition, an overhead mixing disc can be used to grind the pigments using uniform sand at 500-800 micron. The pigments are loaded into the solvents and are mixed using a cowles blade until the viscosity is uniform and the mixing solution makes a donut upon mixing. After mixing for a period of time, an amount of the mixture is deposited on a Hegman grind block and a measurement of the dispersion is read. If the dispersion is acceptable, then additional solvent is then added to get the mixture to a pourable viscosity. If the dispersion is not acceptable, then the mixture is put on the disc overhead mixer and a measured amount of media sand is added. The mixture is allowed to further mix at a specified time and speed, after which the mixture is checked for dispersion quality on a Hegman grind block. An addition of a resin, such as Duramac HS-207-2012, can be added to the pigment dispersion with the sand to see if a difference in dispersion quality was observed. After the acceptable dispersion level is met, the mixture is adjusted, for letdown for the final product viscosity, using solvent and is poured through a 100 micron filter. After allowing the dispersions to set overnight, observations are made regarding the material stability. The final dispersion mixture is then further dispersed into different resin systems. First the viscosity of the dispersion with the pigment and ketal is checked for viscosity. Then, the material is mixed into a measured amount of resin and the viscosity profile is checked for that mixture. The predispersion can be used to further disperse the pigment into different resin systems.

Examples 18-27

Examples were run in a 1 gallon hastelloy C reactor. The batch conditions and GC results are shown in Table 22. The GC analysis was performed as follows.

| | |
|---|---|
| Injector | 1 µL, Split injection @ 250° C. |
| | Split ratio 40:1 |
| | Spilt flow 60 mL/min |
| Column | Rxi-5 ms, 30 m × 0.25 mm ID × 0.25 µm |
| | Carrier flow: He @ 1.5 mL/min |
| Oven | 60° C. for 3.5 min., |
| | then 20° C./min to 350° C. for 2 min. |
| | Run Time: 20 min. |
| Detector | FID @ 300° C., |
| | H2 flow: 30 mL/min |
| | Air flow: 400 mL/min |
| | He make-up flow: 25 mL/min |
| Sample prep | 0.04-0.06 g in 1.5 mL methyl t-butyl ether |

Example 18

To the reactor was loaded 1,3-dioxolane-2-propanoic acid, 2,4-dimethyl-, butyl ester, CAS 162336-72-3, (1400 g) and 70 g (5 wt %) barium promoted copper-chromite catalyst from Strem (Catalog #29-0410) which was crushed with a mortar and pestle and sieved to less than 125 micrometer size. Agitation was set at 1800 rpm. The reaction was run at 240° C. and 3500-3800 psig hydrogen for 300 minutes.

Example 19

To the reactor was loaded 1,3-dioxolane-2-propanoic acid, 2,4-dimethyl-, butyl ester, CAS 162336-72-3, (1400 g) and 70 g (5 wt %) barium promoted copper-chromite catalyst from Strem (Catalog #29-0410) which was crushed with a mortar and pestle and sieved to less than 125 micrometer size. Agitation was set at 2800 rpm. The reaction was run at 220° C. and 3700-4000 psig hydrogen for 420 minutes.

Example 20

To the reactor was loaded 1,3-dioxolane-2-propanoic acid, 2,4-dimethyl-, butyl ester, CAS 162336-72-3, (1400 g) and 70 g (5 wt %) barium promoted copper-chromite catalyst from Strem (Catalog #29-0410) which was crushed with a mortar and pestle and sieved to less than 125 micrometer size. Agitation was set at 2800 rpm. The mixture was dried at 120° C. and 30 torr vacuum for 30 minutes to remove water. The reaction was run at 240° C. and 3600-4000 psig hydrogen for 65 minutes.

Example 21

This is a repeat of example 20 with 90 minutes reaction time.

Example 22

This is a repeat of example 20 with 80 minutes reaction time.

Example 23

The product from example 22 was removed from the reactor while leaving the used catalyst in the reactor. To the reactor was loaded 1,3-dioxolane-2-propanoic acid, 2,4-dimethyl-, butyl ester, CAS 162336-72-3, (1400 g). The temperature, agitation, and pressure were the same as in example 20, but the reaction time was held to 28 minutes.

Example 24

The product from example 23 was removed from the reactor while leaving the used catalyst in the reactor. The reaction of example 23 was carried out with 33 minutes reaction time. This is the third batch with the same catalyst load.

Example 25

The product from example 24 was removed from the reactor while leaving the used catalyst in the reactor. The reaction of example 23 was carried out except the reaction was run at 220° C. and the reaction time was 38 minutes. This is the fourth batch with the same catalyst load.

Example 26

The product from example 25 was removed from the reactor while leaving the used catalyst in the reactor. The reaction of example 23 was carried out with 48 minutes reaction time. This is the fifth batch with the same catalyst load.

Example 27

The product from example 26 was removed from the reactor while leaving the used catalyst in the reactor. The reaction of example 23 was carried out with 58 minutes reaction time. This is the sixth batch with the same catalyst load.

Example 29

Purification of Ketal Alcohol By Distillation

The product from example 28 (1395.6 g) was placed in a 3 L round bottom flask and rotary evaporated at 7.5 torr and 65° C. to remove low boiling components including methyl THF and 1-butanol and yield 1002.3 g of liquid. A portion of the liquid (698.1 g) was loaded to a 1 L flask equipped with distillation column and reflux splitter. The material was distilled by fractional distillation. Fraction 1 (130.15 g) was

TABLE 22

| | Batch | | | | | | | | | |
|---|---|---|---|---|---|---|---|---|---|---|
| | 1 | 2 | 3 | 4 | 5 | 6 | 7 | 8 | 9 | 10 |
| Reaction Time (min) | 300 | 420 | 65 | 90 | 80 | 28 | 33 | 38 | 48 | 58 |
| Temp ° C. | 240 | 220 | 240 | 240 | 240 | 240 | 240 | 220 | 220 | 220 |
| Agitation (rpm) | 1800 | 2800 | 2800 | 2800 | 2800 | 2800 | 2800 | 2800 | 2800 | 2800 |
| Pressure (psig) | 3500-3800 | 3700-4000 | 3600-4000 | 3600-4000 | 3600-4000 | 3600-4000 | 3600-4000 | 3600-4000 | 3600-4000 | 3600-4000 |
| | Yield by Assay | | | | | | | | | |
| Selectivity | 26.95% | 46.64% | 64.18% | 54.39% | 60.61% | 82.27% | 81.26% | 87.63% | 86.68% | 85.06% |
| Conversion (%) | 99.6 | 66.1 | 86.3 | 97.2 | 91.3 | 96.4 | 98.0 | 92.6 | 96.6 | 98.2 |
| Yield % | 18.82 | 24.28 | 44.71 | 43.37 | 45.54 | 72.66 | 72.45 | 77.95 | 76.72 | 77.18 |
| | GC Area % | | | | | | | | | |
| Butanol | 37.4 | 24.8 | 32.1 | 35.8 | 33.5 | 35.1 | 35.7 | 33.7 | 35.1 | 35.6 |
| Methyl THF | 21.9 | 9.6 | 8.9 | 13.4 | 10.0 | 5.5 | 6.3 | 3.6 | 4.3 | 5.3 |
| Propylene glycol | 11.9 | 6.3 | 5.8 | 8.5 | 6.4 | 3.8 | 4.2 | 2.6 | 3.1 | 3.6 |
| 1-pentanol | 2.0 | 0.8 | 1.0 | 1.4 | 1.1 | 0.5 | 0.6 | 0.3 | 0.4 | 0.4 |
| 1,4-pentanediol | 1.9 | 1.4 | 0.7 | 0.9 | 0.7 | 0.3 | 0.3 | 0.2 | 0.2 | 0.2 |
| Ketal alcohol product | 13.6 | 16.4 | 31.1 | 28.8 | 30.9 | 47.0 | 46.9 | 49.1 | 50.4 | 49.9 |
| ether diol | 11.0 | 7.0 | 6.7 | 8.5 | 7.1 | 3.2 | 3.1 | 1.9 | 2.2 | 2.4 |
| Starting Material | 0.4 | 33.9 | 13.7 | 2.8 | 8.7 | 3.6 | 2.0 | 7.4 | 3.4 | 1.8 |

Example 28

Figure 3:
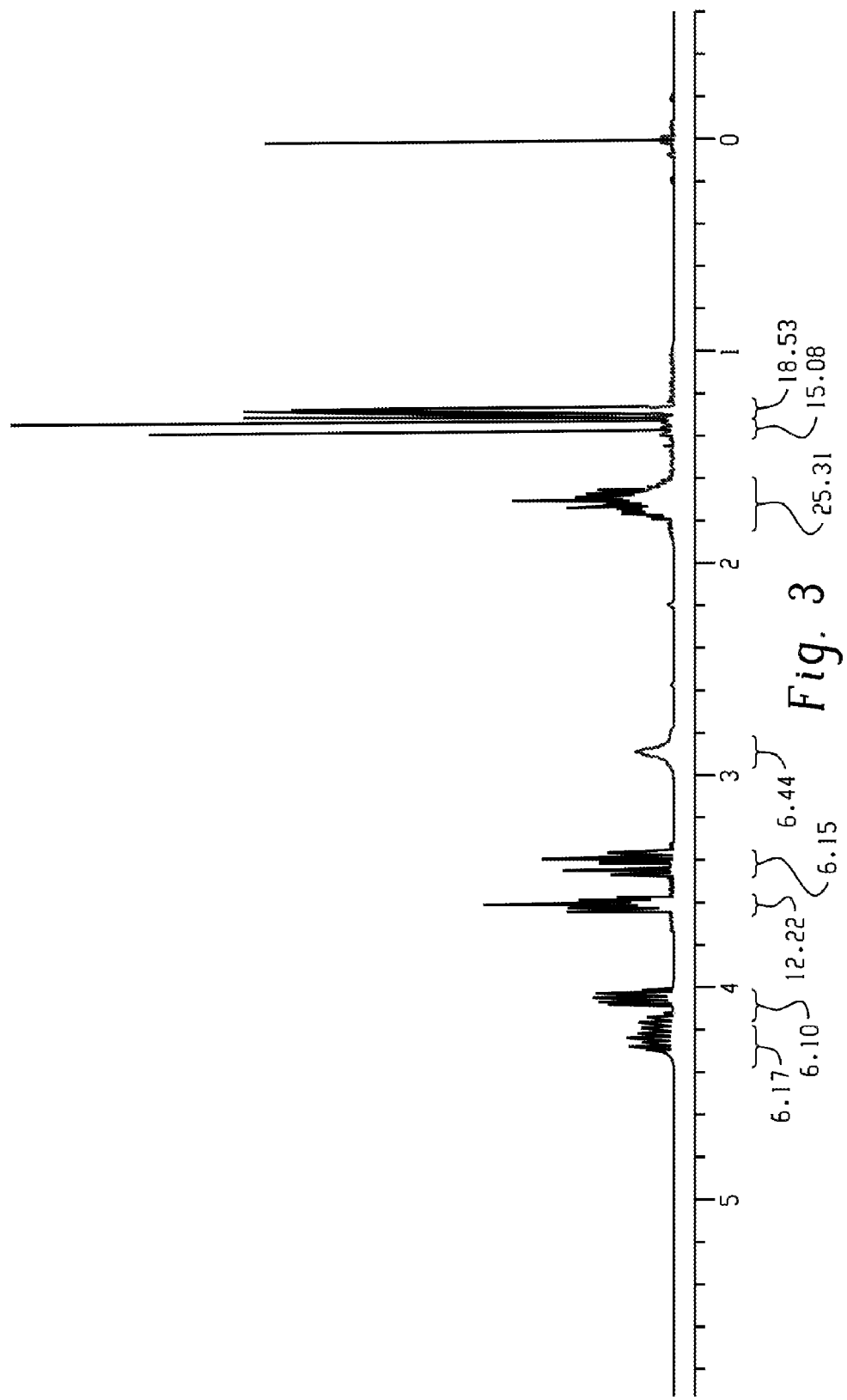
FIG. 3 is an $^1$H-NMR result for the product obtained in Example 20.

In a 5 L three-neck round bottom flask, 1,3-dioxolane-2-propanoic acid, 2,4-dimethyl-, ethyl ester, (264 grams, 1.31 moles) and methanol (79 mL) were dissolved into anhydrous diethyl ether (2.5 L). The flask was fitted with a mechanical stirrer, and placed into a heating mantle. While in the hood, lithium borohydride (43 grams, 1.97 moles) was added slowly. After addition of the lithium borohydride, the flask was fitted with two condensers, and heated at reflux for 2.5 hours. After heating, the reaction mixture was placed in an ice bath and with stirring the reaction mixture was neutralized with 1M HCl. Additional water was added until all solids were dissolved. The ethereal layer was removed and the aqueous layer was extracted with dichloromethane (2×500 ml). The combined organic layers were dried over anhydrous sodium sulfate, and the solvents removed by rotary evaporator to yield pure product (181 gram, 86%). GC-MS and $^1$H-NMR data were obtained as shown in FIG. 3 to confirm the structure of the product and establish purity.

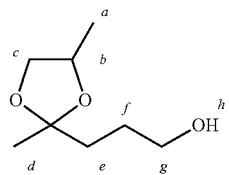

collected with reflux splitting off, 72 torr vacuum, and overhead temperature of 58 to 136° C. Fraction 2 (16.7 g) was collected at a 1:1 split ratio, 55 torr vacuum, and 114-143° C. overhead temperature. Product (460.8 g) of >98% purity was then collected at a 1:1 split ratio, 55 ton vacuum, and 144° C. overhead temperature.

Example 30

Hauthane HD-4675 (from Hauthaway) is a hard, co-solvent free, aliphatic, polyester polyurethane dispersion at 38% solids (±1%).

Samples A and B are prepared by mixing components shown in Table 23. Films are drawn onto cold roll steel panels with a drawdown bar with a thickness of 5-mil. The panels are left on the bench to dry at room temperature. "Dry to touch time" is the elapsed time from drawdown until depressing a finger lightly on the coating no longer leaves a fingerprint or smudge.

TABLE 23

| Sample | Solvent | Wt. % Solvent | Wt. % Hauthane HD-4675 |
|---|---|---|---|
| A | None | 0 | 100 |
| B | Ketal alcohol (1a) | 5 | 95 |

Example 31

Hauthane HD-4669 (from Hauthaway) is a hard, co-solvent free, aliphatic, aqueous polyurethane dispersion at 40% solids (±1%).

Hauthane HD-4669 (95 wt. %) was mixed by hand with ketal alcohol (1a) (5 wt. %). A film was drawn onto cold roll steel panels with a drawdown bar with a thickness of 5-mil. The panel was cured in an oven at 130° C. for 20 minutes. After the oven cure, the composition forms a film.

Examples 32-34

EPON 828 (Momentive) is an undiluted, bifunctional bisphenol A/epichlorohydrin liquid epoxy resin.

Example 32: EPON 828 (50 wt. %) and water (50 wt. %) were mixed by hand at room temperature. EPON 828 remained insoluble in the water.

Example 33: EPON 828 (50 wt. %) and ketal alcohol (1a) (50 wt. %) were mixed by hand at room temperature and formed a homogeneous mixture with no visible signs of incompatibility.

Example 34: EPON 828 (25 wt. %), ketal alcohol (1a) (25 wt. %), and water (50 wt. %) mixed by hand at room temperature. EPON 828 is easily dispersible with agitation. The resin separates, so further stabilization is needed.

Example 35

Beckopox EP122W (Cytec) is a water-emulsifiable Bisphenol A/Bisphenol F epoxy delivered as 100% resin. Beckopox EH623W (Cytec) is a waterborne polyamine adduct hardener, delivered at 80% non-volatiles.

Beckopox EP122W (2.85 g), epoxy hardener 623 (2.85 g), 0.3 g of ketal alcohol (1a), and 3 g of water are mixed by hand. The film is drawn down on cold roll steel panels at 3 mil wet thickness and cured in the oven for 20 minutes at 130° C.

Example 36

Duramac WR216-3610 (Momentive) is a water-dispersible alkyd resin delivered at 98% non-volatile content. It is a viscous, amber-colored liquid at room temperature.

A composition using Duramac WR216-3610 as-received without neutralization is prepared. The components and their relative amounts are shown in Table 24.

TABLE 24

| Solvent | Wt. % Solvent | Wt. % Duramac WR216-3610 | Wt. % Water |
|---|---|---|---|
| Ketal alcohol (1a) | 2.5 | 47.5 | 50 |

Example 37

Triethylamine (TEA) is added in an amount to stoichiometrically neutralize 100% of the acids on the alkyd resin. The ingredients of each sample in Table 25 are weighed into a vial and agitated by hand at room temperature (approximately 22° C.).

TABLE 25

| Sample | Solvent | Solvent (g) | Duramac WR216-3610 (g) | DI water (g) | TEA (g) |
|---|---|---|---|---|---|
| A | None | 0 | 5 | 5 | 0.765 |
| B | Ketal alcohol (1a) | 0.75 | 4.25 | 5 | 0.65 |

Example 38

The samples in Table 26 are prepared according to the procedure in example 37 except triethylamine sufficient to neutralize 50% of the acids on the alkyd resin was added. Sample A forms an opaque, tan mixture with a viscosity too high to pour.

TABLE 26

| Sample | Solvent | Solvent (g) | Duramac WR216-3610 (g) | DI water (g) | TEA (g) |
|---|---|---|---|---|---|
| A | Ketal alcohol (1a) | 0.25 | 4.75 | 5 | 0.363 |
| B | Ketal alcohol (1a) | 0.125 | 2.375 | 7.5 | 0.1817 |

Example 39

Heat-Cured Alkyd Coatings

Compositions were prepared according to Table 27 but scaled to fit in a 250 mL pot. The ingredients of the pigment grind are added in the order given and mixed with an overhead mixer for 5 minutes to get a donut formation. The ingredients of the letdown are added individually in the order given to the pigment grind and mixed for 5 minutes. Drawdowns of the compositions are made on cold roll steel panels with a drawdown bar of 2 mil thickness. The compositions are cured for 20 minutes at 175° C.

TABLE 27

| Ingredient | A (weight in g) | B (weight in g) |
|---|---|---|
| Duramac WR74-7451 | 144.6 | 144.6 |
| Triethylamine | 7.5 | 7.5 |
| Cymel 300 | 25.6 | 25.6 |
| Eastman EB | 19.5 | 19.5 |
| Red-LPK | 0 | 19.5 |
| BYK 302 | 2.8 | 2.8 |
| TiPure R-960 | 198.3 | 198.3 |
| DI water | 75 | 75 |
| Letdown | | |
| | 101.9 | 101.9 |
| Triethylamine | 9.2 | 9.2 |
| DI water | 360 | 360 |
| DI water | 6.8 | 6.8 |

1. Cymel 300 (Cytec Industries) is a high solid (98% non-volatile) methylated melamine resin with approximately 76% monomer content.
2. BYK302 (BYK) is solvent-free polyether modified polydimethylsiloxane surface additive.
3. Eastman EB (Eastman) is ethylene glycol monobutyl ether.
4. Ti-Pure R-960 (DuPont) is a rutile titanium dioxide pigment.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The endpoints of all ranges directed to the same component or property are inclusive of the endpoint and independently combinable.

Unless otherwise defined, all terms (including technical and scientific terms) used herein have the same meaning as commonly understood by one of ordinary skill in the art to which this invention belongs. The term "paint" includes any protective exterior coatings that are also known as, for example, lacquer, electropaint, shellac, top coat, base coat, color coat, and the like. The term "remover" includes compositions that clean, spot clean, and strip, and "removal" includes cleaning, spot cleaning, and stripping. The compounds made by the above-described methods have, in embodiments, one or more isomers. Where an isomer can exist, it should be understood that the invention embodies methods that form any isomer thereof, including any stereoisomer, any conformational isomer, and any cis, trans isomer; isolated isomers thereof; and mixtures thereof.

Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group. Alkyl groups can be straight-chained or branched. Throughout the specification, reference is made to various bivalent groups. Such groups are the same as the monovalent groups that are similarly named, and are typically indicated with an "ene" suffix. For example, a C1 to C6 alkylene group is a bivalent linking group having the same structure as a C1 to C6 alkyl group.

All cited patents, patent applications, and other references are incorporated herein by reference in their entirety.

The various embodiments described above are provided by way of illustration only and should not be construed to limit the claims attached hereto. The present compositions can comprise, consist of, or consist essentially of, any of the disclosed or recited elements. Thus, the invention illustratively disclosed herein can be suitably practiced in the absence of any element that is not specifically disclosed herein. Various modifications and changes will be recognized that can be made without following the example embodiments and applications illustrated and described herein, and without departing from the true spirit and scope of the following claims.

What is claimed is:

1. A cleaning or personal care composition comprising
a cleaning or personal care component; and
a ketal alcohol of formula (1)

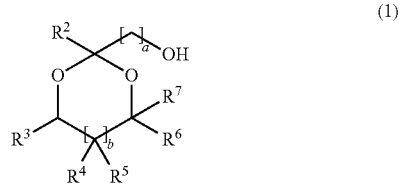

(1)

wherein
$R^2$ is hydrogen or C1-3 alkyl,
each $R^3$, $R^4$, and $R^5$ is independently hydrogen or C1-6 alkyl,
$R^6$ and $R^7$ are each independently hydrogen, C1-6 alkyl optionally substituted with at least one hydroxyl groups,
a=1-6, and
b=0-2.

2. The composition of claim 1, wherein $R^2$ is methyl, $R^3$, $R^4$, and $R^5$ are each independently hydrogen or C1-3 alkyl, $R^6$ is hydrogen, C1-3 alkyl, or —CH$_2$OH, $R^7$ is hydrogen, a=1-4, and b=0-1.

3. The composition of claim 1, wherein $R^2$ is methyl, $R^3$ is hydrogen, $R^6$ is hydrogen, C1-3 alkyl, or —CH$_2$OH, $R^7$ is hydrogen, a=2-3, and b=0.

4. The composition of claim 1, wherein $R^2$ is methyl, $R^3$ is hydrogen, $R^6$ is hydrogen, methyl, ethyl, or —CH$_2$OH, $R^7$ is hydrogen, a=3, and b=0.

5. The composition of claim 1, wherein the ketal alcohol is of formula (1a)
formula (1b)

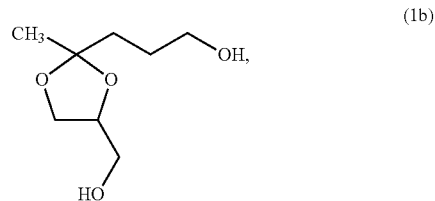

(1b)

or a combination comprising at least one of the foregoing.

6. The composition of claim 1, wherein the composition is a cleaning composition, and the cleaning component is a cosolvent, a plurality of abrasive particles, an organic amine, an antioxidant, a biocide, a colorant, a corrosion inhibitor, a defoamer, a dye, an enzyme, a light stabilizer, an odor masking agent, a plasticizer, a preservative, a rust inhibitor, a surfactant, a thickener, a soil suspending agent, a builder, a chelating agent, a bleach, a bleach activator, a bleach stabilizer, a pH control agent, a hydrotrope, a fabric softener, or a combination comprising at least one of the foregoing.

7. The composition of claim 6, comprising 0-1 weight percent water, based on the total weight of the composition.

8. The composition of claim 6, comprising
20 to 99 weight % of water,
0.1 to 40 weight % of the ketal alcohol of formula (1), and
0.1 to 20 weight % of the surfactant.

9. The composition of claim 6, wherein the composition is a laundry detergent, hard surface cleaner, soft surface cleaner, dishwasher cleaner, glass cleaner, oven cleaner, concrete cleaner, form cleaner, mold cleaner, paint remover, graffiti remover, ink remover, sealant remover, adhesive remover, mastic remover, photoresist remover, wax remover, asphalt remover, sap remover, oil remover, grease remover, or a combination comprising at least one of the foregoing.

10. The composition of claim 9, wherein the composition is a liquid laundry detergent comprising, based on the total weight of the liquid laundry detergent,
50 to 95 weight % water;
0.1 to 25 weight % of the ketal alcohol of formula (1); and
0.1 to 45 weight % of at least one surfactant; and
a builder, a chelating agent, a chlorine bleach, a non-chlorine bleach, an abrasive, an anti-deposition agent, a brightening agent, or a combination comprising at least one of the foregoing.

11. The composition of claim 9, wherein the composition is a concentrated liquid laundry formulation comprising, based on the total weight of the formulation,
less than 50 weight % of water;
5 to 70 weight % of a ketal alcohol of formula (1);
5 to 90 weight % of a surfactant; and a builder, a chelating agent, a chlorine bleach, a non-chlorine bleach, an abrasive, an anti-deposition agent, a brightening agent, or a combination comprising at least one of the foregoing.

12. The composition of claim 9, wherein the composition is an aqueous hard surface cleaner comprising, based on the total weight of the cleaner,
20-99 weight % of water;
1-50 weight % wt. % of a ketal alcohol of formula (1); and
0.01-40 weight % of an anionic surfactant, a nonionic surfactant, or a combination comprising at least one of the foregoing surfactants.

13. The composition of claim 1, wherein the composition is a personal care composition, and the personal care component is an active agent, a cosmetic colorant, a surfactant, or a combination comprising at least one of the foregoing.

14. The composition of claim 13, wherein the active agent is an anti-aging agent, anti-acne agent, skin whitener, ultraviolet light absorber, tanning agent, anti-alopecia agent, antifungal agent, anti-dandruff agent, anti-perspirant, antimicrobial, organic medicinal, depilatory compound, hair dye, insect repellant, or a combination comprising at least one of the foregoing.

15. The composition of claim 13, wherein the composition is a shampoo, a body cleaner, an eye care product, a cosmetic, a fragrance, a hair coloring formulation, a hair straightening or permanent wave formulation, a nail care formulation, a toothpaste, a mouthwash, a shave cream, a skin care formulation, a sun care formulation, a lip care formulation, an antiperspirant, or a foot care formulation.

16. The composition of claim 13, comprising 0.001 to 40 wt. % the personal care component, based on the total weight of the cosmetic composition.

17. The composition of claim 13, comprising
0.001 to 30 wt. % the active agent, and
2 to 60 wt. % water, each based on the total weight of the personal care composition.

18. The composition of claim 13, wherein the personal care composition is in the form of an emulsion, and wherein the composition comprises
i) a continuous phase and a disperse phase wherein the continuous phase or the disperse phase is an aqueous phase and the other is an oil phase; or at least two co-continuous phases wherein at least one of the co-continuous phases is an aqueous phase and at least one of the co-continuous phases is an oil phase; and wherein any of the foregoing oil phases comprises at least one of
(a) a paraffinic, naphthenic, or aromatic mineral oil,
(b) a nonionic organic compound having a melting temperature of less than 45° C., a molecular weight of at least 190 Daltons, an amido or ester group, and an alkyl chain containing at least 8 carbon atoms, and a solubility in water of no greater than 1 part in 99 parts of water,
(c) a nonionic organosilicone compound having a melting temperature of less than 45° C., and a solubility in water of no greater than 1 part in 99 parts of water,
(d) a long chain alcohol, and
(e) a wax.

* * * * *